US006489323B1

(12) United States Patent
Hansen, Jr. et al.

(10) Patent No.: US 6,489,323 B1
(45) Date of Patent: Dec. 3, 2002

(54) HETEROBICYCLIC AND TRICYCLIC NITRIC OXIDE SYNTHASE INHIBITORS

(75) Inventors: Donald W. Hansen, Jr., St. Louis; R. Keith Webber, St. Charles, both of MO (US); E. Ann Hallinan, Evanston, IL (US); Mihaly V. Toth, St. Louis, MO (US); Barnett S. Pitzele; Alok K. Awasthi, both of Skokie, IL (US); Alan E. Moormann, St. Charles, MO (US); Suzanne Metz, Chesterfield, MO (US); Jeffery S. Snyder, Manchester, MO (US); William M. Moore, St. Charles, MO (US); Jeffrey A. Scholten, Chesterfield, MO (US)

(73) Assignee: G.D. Searle & Co., Skokie, IL (US)

( * ) Notice: Subject to any disclaimer, the term of this patent is extended or adjusted under 35 U.S.C. 154(b) by 0 days.

(21) Appl. No.: 09/329,583

(22) Filed: Jun. 10, 1999

Related U.S. Application Data
(60) Provisional application No. 60/135,865, filed on May 25, 1999, and provisional application No. 60/088,823, filed on Jun. 10, 1998.

(51) Int. Cl.$^7$ .................... C07D 498/04; A61K 31/55
(52) U.S. Cl. .................... 514/211.1; 540/578
(58) Field of Search .................... 540/578; 514/211.1

(56) References Cited

U.S. PATENT DOCUMENTS

| | | | |
|---|---|---|---|
| 2,049,582 A | 8/1936 | Ziegler | 564/225 |
| 3,109,848 A | 11/1963 | Bortnick et al. | 548/512 |
| 3,121,093 A | 2/1964 | Bortnick et al. | 548/411 |
| 3,132,151 A | 5/1964 | Bortnick et al. | 548/550 |
| 3,501,487 A | 3/1970 | Poos | 546/279.1 |
| 3,563,994 A | 2/1971 | Wollweber et al. | 546/223 |
| 3,694,432 A | 9/1972 | Hershenson | 428/186 |
| 3,725,435 A | 4/1973 | Poos | 548/526 |
| 3,816,457 A | 6/1974 | Grisar et al. | 540/480 |
| 4,046,909 A | 9/1977 | Rasmussen et al. | 514/426 |
| 4,061,746 A | 12/1977 | Blohm et al. | 514/183 |
| 4,126,613 A | 11/1978 | Grisar et al. | 540/605 |
| 4,126,621 A | 11/1978 | Grisar et al. | 540/546 |
| 4,153,235 A | 5/1979 | Grisar et al. | 540/482 |
| 4,443,468 A | 4/1984 | Maillard et al. | 514/422 |
| 4,523,020 A | 6/1985 | Moormann et al. | 545/353.1 |
| 4,525,476 A | 6/1985 | Butler et al. | 514/326 |
| 4,533,739 A | 8/1985 | Pitzele et al. | 548/555 |
| 4,556,674 A | 12/1985 | Maillard et al. | 514/426 |
| 4,579,951 A | 4/1986 | Pitzele et al. | 546/223 |
| 4,699,918 A | 10/1987 | Maillard et al. | 209/397 |
| 4,855,444 A | 8/1989 | Wambach | 514/397 |
| 4,962,204 A | 10/1990 | Wambach | 548/408 |
| 5,015,633 A | 5/1991 | Sudilovsky | 514/91 |
| 5,028,627 A | 7/1991 | Kilbourn et al. | 514/565 |
| 5,051,444 A | 9/1991 | Tamoto et al. | 548/408 |
| 5,059,712 A | 10/1991 | Griffith | 562/560 |
| 5,081,148 A | 1/1992 | Braquet et al. | 514/162 |
| 5,132,453 A | 7/1992 | Griffith | 562/560 |
| 5,196,439 A | 3/1993 | Sugimoto et al. | 514/318 |
| 5,216,025 A | 6/1993 | Gross et al. | 514/565 |
| 5,246,971 A | 9/1993 | Williamson et al. | 514/634 |
| 5,266,594 A | 11/1993 | Dawson et al. | 514/560 |
| 5,273,875 A | 12/1993 | Griffith | 435/1.1 |
| 5,621,004 A | 4/1997 | Dunn et al. | 514/551 |
| 5,629,322 A | 5/1997 | Guthikonda et al. | 514/33 |

FOREIGN PATENT DOCUMENTS

| | | |
|---|---|---|
| CZ | 191584 | 10/1978 |
| EP | 0370320 | 5/1990 |
| EP | 0446699 | 9/1991 |
| EP | 0462948 | 12/1991 |
| EP | 0676196 | 10/1995 |
| EP | 0713704 | 5/1996 |
| EP | 0713876 | 5/1996 |
| EP | 0717040 | 6/1996 |
| GB | 1180876 | 2/1970 |
| GB | 1367598 | 9/1974 |
| GB | 2240041 | 7/1991 |
| WO | 91/04023 | 4/1991 |
| WO | 91/04024 | 4/1991 |
| WO | 93/13055 | 7/1993 |
| WO | 93/16721 | 9/1993 |
| WO | 93/24126 | 12/1993 |
| WO | 94/12163 | 6/1994 |
| WO | 94/12165 | 6/1994 |
| WO | 94/14780 | 7/1994 |
| WO | 94/16729 | 8/1994 |
| WO | 95/05363 | 2/1995 |
| WO | 95/11231 | 4/1995 |
| WO | 95/31987 | 11/1995 |
| WO | 95/32203 | 11/1995 |
| WO | WO95/11231 | 5/1996 |
| WO | 96/14842 | 5/1996 |
| WO | 96/14844 | 5/1996 |
| WO | 96/18616 | 6/1996 |
| WO | WO96/33175 | 10/1996 |
| WO | WO96/35677 | 11/1996 |
| WO | 97/16430 | 5/1997 |

OTHER PUBLICATIONS

"Steadman's Medical Dictionary", 1995, Williams & Wilkins, Montvale, NJ., p. 1211.

(List continued on next page.)

*Primary Examiner*—Mukund J. Shah
*Assistant Examiner*—Thomas C McKenzie
(74) *Attorney, Agent, or Firm*—Philip B. Polster, II

(57) ABSTRACT

The current invention relates to compounds of Formula I

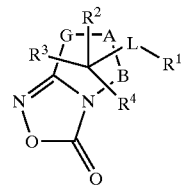

I pharmaceutical compositions and methods of use as nitric oxide synthase inhibitors, wherein the substituents are defined in the application.

17 Claims, No Drawings

OTHER PUBLICATIONS

Bennett, J.C. and Plum, F , eds., "Cecil Textbook of Medicine 20th Ed." 1996, W.B. Saunders Company, Philadelphia, p. LVX.

Berkow, R. Ed.–in–Chief, "The Merck Manual of Diagnosis and Therapy, 16th Ed.", 1992, Merck & co., Rahway, NJ, p2801.

Hawley, Gessner, "The Condensed Chemical Dictonary", 1977, Van Nostrand, New York, p. 16.

Fletcher, J.H. et al, "Nomenclature of Organic Compounds", American Chemical Society, Washington, D.C., 1974, p. 147.

Grant, R.L. et al, "Grant and Hackh's Chemical Dictionary", McGraw–Hill, New York, 1987, p. 14.

Ulrich, H. et al, J. Org. Chem., 43, 1978, 1544–1546.

Annual Reports in Medicinal Chemistry, vol. 31, James Bristol, ed., Academic Press, San Diego, 1996, p 221–230.

Gutteridge, "Acylation of 2–Amino–5, 5–dimethyl–Δ–pyrroline 1–Oxide", J. Chem. Soc., (C), pp. 3121–3125, 1971.

Langlois et al., "Derivatives of Imidazole, 1,3,4–triazole and tetrazole", J. Heterocycl. Chem., vol. 19, No. 1, pp. 193–200, 1982 (English Summary, p. 200).

Langlois et al., "Synthesis and Antidepressant Properties of 2–Amino–4–phenyl–1–pyrroline Derivatives", Eur. J. Med. Chem., vol. 13, No. 2, pp. 161–169, 1978 (English Summary, p. 169).

Klötzer et al. "Acylderivatives of 2–Amino–1–pyrrolines", Monatshefte für Chemie, vol. 102, No. 2, pp. 627–634, 1971 (English Summary, p. 627).

Klötzer et al. "Synthesis of Substituted 2–amino–1–pyrrolines, I." Monatshefte für Chemie, vol. 101, No. 5, pp. 1263–1270, 1970 (English Summary, p. 1263).

Nakane et al., "Novel Potent and Selective Inhibitors of Inducible Nitric Oxide Synthase", Molecular Pharmacology, vol. 47, pp. 831–834, 1995.

Dunbar et al., "Design, Synthesis, and Neurochemical Evaluation of 2–Amino–5–(alkoxycarbonyl)–3,4,5,6–tetrahydopyridines and 2–Amino–5–(alkoxycarbonyl)–1,4,5,6–tetrahydropyrimidines as $M_1$ Muscarinic Receptor Agonists", J. Med. Chem., vol. 37, No. 17, pp. 2774–2782, 1994.

Klötzer et al. "Synthesis of Substituted 2–Aminopyrrolines, II." Monatshefte für Chemie, vol. 101, No. 6, pp. 1841–1850, 1970 (English Summary, p. 1841).

Berge et al., "Pharmaceutical Salts", J. Pharm. Sci., vol. 66, No. 1, pp. 1–19, 1977.

Moncada et al., "Nitric Oxide: Physiology, Pathophysiology, and Pharmacology", Pharmacological Reviews, Vo. 43, No. 2, pp. 109–142, 1991.

Moncada et al, "Biosynthesis of Nitric Oxide from L–Arginine", Biochemical Pharm., vol. 38, No. 11 pp. 1709–1715, 1989.

Mazurek et al., "Theoretical Studies of Tautomerism of Clonidine Vacuum and in Water Medium", Theochem, 82(1–2), 23–8, 1991.

Bertolinin et al., "Nitric Oxide Synthase Inhibitors: Recent Advances", Cardiovascular & Renal Patent Update, Ashley Publications Ltd., pp. 1339–1345, 1994.

Culvenor, C.C.J. et al, Aust. J. Chem., 24 (1971) 371–375.

Caujolle, R. et al, Eur. J. Med. Chem. Chim. Ther., 28(1) (1993) 29–35.

Kato et al, Chem. Pharm. Bull., 20(1972) 901.

Anderson, Wayne K. et al, Synth. Commun., 19(13–14) (1989) 2237–2242.

Olomucki et al, Biochim. Biophys. Acta, 263 (1972) 213–216.

Otake, N. et al, Tetrahedron Lett., 19 (1965) 1411–1419.

Patent: Kerin Seiyaku Kabushiki Kaisya, JP, A, 17189, 1968; Referati vnyi Zhurnal. Khimiya., 1 (1970) N469P.

Umezawa et al, J. Antibiot., 26 (1973) 625, 637.

Bycroft et al., J. Antibiot., 22 (1969) 133–134.

Bycroft et al., J. Chem. Soc.(C), (1971) 3040–3046.

Marconi et al, J. Antibiot., 23 (1970) 120–124.

Kretow et al, J. Gen. Chem. USSR, 32 (1962) 464.

Dorn et al, Chem. Ber., 103(1970) 2505–2511.

Andrewes et al, Proc. R. Soc. London B, 133 (1946) 20, 53 (Beilstein Registry ID Only).

Schubert, H. W. et al, Arch. Pharm. Ber. Dtsch. Pharm. Ges., 301(10) (1968) 750–762.

Rodricks et al, J. Org. Chem., 36 (1971) 46–48.

Stefanye et al, J. Amer. Chem. Soc., 77 (1955) 761–762.

Goodman et al, J. Org. Chem., 23 (1958) 1954–1956.

Goodman et al, J. Org. Chem., 23 (1958) 1251–1255.

Perrin et al., "Absence of Stereoelectronic Control in Hydrolysis of Cyclic Amidines", J. Am. Chem. Soc., vol. 108, No. 19, pp. 5997–6003, 1986.

Huber et al., "Saturated Heterocycles, Part 88. Synthesis of a New Ring System: Dipyrido–[1.2–α:4,3–d] pyrimidin–11–one Derivatives", J. Chem. Soc. Perkin Trans. 1, pp. 909–912, 1987.

Kökösi et al., "Nitrogen Bridgehead Compounds. Part 19(1). Synthesis of Polymethylenepyrimidin–4–ones", J. Heterocyclic Chem., vol. 19, pp. 909–912, 1982.

Brown et al., Hydropyrimidines, Part II, pp. 4041–4045, 1962.

Adcock et al., 2–Amino–2–imidazolines 2–Amino–2–oxazolines, Part II, pp. 474–479, 1965.

Stefanye et al., "Cyclic Guanidines from Nitrimino Compounds", J. Am. Chem. Soc., vol. 77, No. 3 pp. 761–762, 1955.

Klayman et al., "2–Amino–2–thiazoline. VII. Unequivocal Structure Assignment of the Products of the Reaction of 2–Amino–2–thiazoline and Its Analogs with Carbethoxy Isothiocyanate", J. Org. Chem., vol. 39, No. 13, pp. 1819–1823, 1974.

Moriconi et al., "Synthesis and Reactions of Cyclic Amidines", J. Org. Chem., vol. 33, No. 5, pp. 2109–2111, 1968.

Wagenaar et al., "Methodology for the Preparation of N–Guanidino–Modified Arginines and Related Derivatives", J. Org. Chem., vol. 58, No. 1, pp. 4331–4338, 1993.

HETEROBICYCLIC AND TRICYCLIC NITRIC OXIDE SYNTHASE INHIBITORS

This application claims priority to U.S. provisional patent application No. 60/088,823, filed Jun. 10, 1998 and U.S. provisional patent application No. 60/135,865 filed May 25, 1999.

BACKGROUND OF THE INVENTION

1. Field of the Invention

The present invention relates to heteroatom containing monocyclic and bicyclic compounds, pharmaceutical compositions containing these novel compounds, and to their use in therapy, in particular their use as nitric oxide synthase inhibitors.

2. Discussion of the Prior Art

It has been known since the early 1980's that the vascular relaxation caused by acetylcholine is dependent on the presence of the vascular endothelium and this activity was ascribed to a labile humoral factor termed endothelium-derived relaxing factor (EDRF). The activity of nitric oxide (NO) as a vasodilator has been known for well over 100 years. In addition, NO is the active component of amylnitrite, glyceryltrinitrate and other nitrovasodilators. The recent identification of EDRF as NO has coincided with the discovery of a biochemical pathway by which NO is synthesized from the amino acid L-arginine by the enzyme NO synthase.

Nitric oxide is the endogenous stimulator of the soluble guanylate cyclase. In addition to endothelium-dependent relaxation, NO is involved in a number of biological actions including cytotoxicity of phagocytic cells and cell-to-cell communication in the central nervous system (see Moncada et al., Biochemical Pharmacology, 38, 1709–1715, 1989; Moncada et al., Pharmacological Reviews, 43, 109–142, 1991). Excess NO production appears to be involved in a number of pathological conditions, particularly conditions which involve systemic hypotension such as toxic shock, septic shock and therapy with certain cytokines (Kerwin et al., J. Medicinal Chemistry, 38, 4343–4362, 1995).

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, Ca++/calmodulin dependent enzyme, located in the endothelium, that releases NO in response to receptor or physical stimulation.

(ii) a constitutive, Ca++/calmodulin dependent enzyme, located in the brain, that releases NO in response to receptor or physical stimulation.

(iii) a Ca++ independent enzyme which is induced after activation of vascular smooth muscle, macrophages, endothelial cells, and a number of other cells by endotoxin and cytokines. Once expressed this inducible NO synthase generates NO continuously for long periods.

The NO released by the two constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase (Knowles and Moncada, Biochem J., 298, 249–258, 1994 Billiar et al., Annals of Surgery, 221, 339–349, 1995; Davies et al., 1995).

There is also a growing body of evidence that NO may be involved in the degeneration of cartilage which takes place in certain conditions such as arthritis and it is also known that NO synthesis is increased in rheumatoid arthritis and in osteoarthritis (McInnes et al., J. Exp. Med, 184, 1519–1524, 1996; Sakurai et al., J. Clin. Investig., 96, 2357–2363, 1995). Accordingly, conditions in which there is an advantage in inhibiting NO production from L-arginine include autoimmune and/or inflammatory conditions affecting the joints, for example arthritis, and also inflammatory bowel disease, cardiovascular ischemia, diabetes, diabetic retinopathy, nephropathy, cardiomyopathy, congestive heart failure, myocarditis, atherosclerosis, migraine, reflux esophagitis, diarrhea, irritable bowel syndrome, cystic fibrosis, emphysema, asthma, chronic obstructive pulmonary disease, bronchiectasis, herniated vertebral discs, obesity, psoriasis, rosacea, contact dermatitis, hyperalgesia (allodynia), cerebral ischemia [both focal ischemia, thrombotic stroke and global ischemia (secondary to cardiac arrest)], anxiety multiple sclerosis and other central nervous system disorders mediated by NO, for example Parkinson's disease and Alzheimer's disease, rhinitis, cancer therapy, and other disorders mediated by NO including opiate tolerance in patients needing protracted opiate analgesics, and benzodiazepine tolerance in patients taking benzodiazepines, and other addictive behavior, for example, nicotine and eating disorders (Kerwin et al., J. Medicinal Chemistry, 38, 4343–4362, 1995; Knowles and Moncada, Biochem J., 298, 249–258, 1994; Davies et al., 1995; Pfeilschifter et al., Cell Biology International, 20, 51–58, 1996).

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy (E. Kelly et al., J. Partent. Ent. Nutri., 19, 234–238, 1995; S. Moncada and E. Higgs, FASEB J., 9, 1319–1330, 1995; R. G. Kilbourn et al, Crit. Care Med., 23, 1018–1024, 1995).

More recently, NO has been identified as being a neurotransmitter in pain pathways of the spinal cord. The administration of NO synthase inhibitors in patients with cronic pain syndromes, and more specifically cronic tension-type headaches, has been shown to reduce the level of pain. (The Lancet, 353:256–257, 287–289)

Some of the NO synthase inhibitors proposed for therapeutic use so far, and in particular L-NMMA, are non-selective; they inhibit both the constitutive and the inducible NO synthases. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

WO 96/35677, WO 96/33175, WO 96/15120, WO 95/11014, WO 95/11231 WO 95/25717, WO 95/24382, WO94/12165, WO94/14780, WO93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In accordance with the present invention novel heterocyclic bicyclic derivatives are provided. These novel inhibitor compounds are represented by the following formula

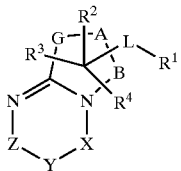

and salts, pharmaceutically acceptable esters, and prodrugs thereof, wherein:

$R^1$ is selected from the group consisting of hydrogen, lower alkyl, lower alkenyl, lower alkynyl, $OR^5$, $SR^5$, $S(O)R^5$, $S(O)_2R^5$, $C(O)R^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, acylamino, carboxy, carboxyalkyl, $P(R^5)_3$, $C(O)$ $R^5$, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, amidino, and guanidino, wherein all said substituents may be optionally substituted with one or more selected from the group consisting of halogen, lower alkyl, lower alkenyl, lower alkynyl, cycloalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, $C(O)R^6$, carboalkoxyalkyl, cyano, nitro, amidino, and guanidino, wherein $R^5$ and $R^6$ of $SO_2NR^5R^6$ and $NR^5SO_2R^6$ may be taken together to form a N-containing heterocycle, optionally substituted by one or more selected from the group consisting of lower alkyl, lower alkenyl, lower alkynyl, cycloalkyl, heterocyclyl, aromatic hydrocarbon, hydroxy, lower alkoxy, aryloxy, thiol, lower thioalkoxy, halogen, cyano, nitro, amino, alkylamino, dialkylamino, aminoalkyl, dialkylaminoalkyl, arylamino, aminoaryl, alkylaminoaryl, acylamino, carboxy, and carboxyalkyl;

$R^1$ may be

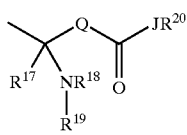

wherein J is selected from the group consisting of O, S and NR;

R is selected from the group consisting of hydrogen, lower alkyl, lower alkenyl, lower alkynyl, cycloalkyl, cycloalkenyl, heterocycle, aromatic hydrocarbon, alkylaryl, alkylheterocycle, all of which may be optionally substituted by one or more of alkyl, hydroxy, alkoxy, halogen, haloalkyl, cyano, amino, and nitro;

NR and $R^{20}$ may optionally form a heterocycle;

$R^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, lower thioalkoxy, halogen, cyano, nitro, amino, alkylamino, dialkylamino, aminoalkyl, dialkylaminoalkyl, arylamino, aminoaryl, alkylaminoaryl, acylamino, carboxy, carboxyalkyl, $C(O)R^6$, carboalkoxyalkyl, $CONR^5R^6$, $S(O)R^5$, $S(O)_2R^5$, $SO_2NR^5R^6$, $NR^5SO_2R^6$, $PO(OR^5)(OR^6)$, amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, lower thioalkoxy, halogen, cyano, nitro, $C(O)R^6$, carboalkoxyalkyl, $S(O)R^8$, $S(O)_2R^8$, $S(O)R^{10}$, $S(O)_2R^{10}$, $SO_2NR^8R^9$, $NR^8SO_2$, $PO(OR^8)(OR^9)$, amidino, and $R^{17}$ is selected from the group consisting of hydrogen, lower alkyl, hydroxyalkyl, alkoxyalkyl, haloalkyl, cycloalkyl, heterocycle, aromatic hydrocarbon, alkylaryl, and alkylheterocycle, all except hydrogen may be optionally substituted by one or more of alkyl, hydroxy, alkoxy, thiol, alkylthiol, halogen, haloalkyl, carboxyl, cyano, amino, and nitro;

$R^{18}$ is selected from the group consisting of hydrogen, hydroxyl, $R^{12}$, $S(O)R^{11}$, $SO_2R^{11}$, $CH_2OC(O)$—$R^{11}$, and $C(O)$—$R^{11}$ wherein $C(O)$—$R^{11}$;

$R^{18}$ and $R^{20}$ may be taken together to form a 5- or 6-membered heterocyclic ring containing two or more heteroatoms which may be optionally substituted by one or more of $R^{16}$;

$R^2$ and L may be taken together to form a 3 to 9 membered alicyclic or heterocyclic ring which may be optionally substituted by one or more of $R^{16}$;

$R^2$ and $R^{17}$ may be taken together to form a 4 to 9 membered alicyclic or heterocyclic ring which may be optionally substituted by one or more of $R^{16}$;

$R^2$ and $R^{18}$ may be taken together to form a 6 to 9 membered heterocyclic ring which may be optionally substituted by one or more of $R^{16}$;

L and $R^{17}$ may be taken together to form a 3 to 9 membered alicyclic or heterocyclic ring which may be optionally substituted by one or more of $R^{16}$;

L and $R^{18}$ may be taken together to form a 4 to 9 membered alicyclic or heterocyclic ring which may be optionally substituted by one or more of $R^{16}$;

$R^{17}$ and $R^{18}$ and may be taken together to form a 4 to 9 membered heterocyclic ring which may be optionally substituted by one or more of $R^{16}$;

$R^{17}$ and Q may be taken together to form a 3 to 9 membered alicyclic or heterocyclic ring which may be optionally substituted by one or more of $R^{16}$;

$R^{18}$ and Q may be taken together to form a 4 to 9 membered heterocyclic ring which may be optionally by one or more of $R^{16}$;

$R^{17}$ and $R^{20}$ and may be taken together to form a 5 to 9 membered heterocyclic ring which may be optionally substituted by one or more of $R^{16}$;

$R^{19}$ is hydrogen, $R^{11}$, or $C(O)$—$R^{11}$;

$R^{11}$ is selected from the group consisting of hydrogen, hydroxyl, alkenyl, alkynyl, heterocyclyl, aromatic hydrocarbon, cycloalkyl, dihydropyridyl, alkyl, alkylthiol, alkoxy, amino, and cycloalkoxy, which may be optionally substituted with one or more of amino, carboxyl, carboxamide, thioalkyl, aromatic hydrocarbon, alkyl, alkylaryl, hydroxy, alkoxy, halogen, trifluoromethyl, nitro, cyano, amino, heterocyclyl, alkylheterocycle, and alkylthiol, which may be optionally substituted with one or more of hydroxy, amino, guanidino, iminoalkyl;

$R^{12}$ is selected from the group consisting of hydrogen, alkyl, alkenyl, alkynyl, cycloalkyl, heterocycle, and aromatic hydrocarbon, all may be optionally substituted by one or more alkyl, hydroxy, alkoxy, halogen, trifluoromethyl, nitro, cyano, or amino groups;

$R^{20}$ is selected from the group consisting of hydrogen, lower alkyl, lower alkenyl, lower alkynyl, cycloalkyl, cycloalkenyl, aromatic hydrocarbon, heterocycle, alkylaryl, and alkylheterocycle, which may be optionally substituted by one or more of halogen, haloalkyl, cyano, nitro, —$CO_2R$, and —$COR$;

$R^{20}$ may also be selected from the group consisting of alkylhydroxy, alkylpolyhydroxy, alkyl(poly)oxyacyl, $CH_2C(=O)OR^{12}$, $CH_2C(=O)NHR^{12}$, $CH_2OC(=O)R^{12}$, and $CH_2OC(=O)VR^{12}$, wherein the $CH_2$ may be optionally substituted by one or more of lower alkyl, cycloalkyl, heterocycle, aromatic hydrocarbon, amidino, guanidino, $CO_2H$, amino, hydroxy, thiol, halogen, haloalkyl, cyano, and nitro;

V is selected from the group consisting of O, S, $CH_2$, $CHR^{12}$, $C(R^{12})_2$, NH, and $NR^{12}$;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, lower thioalkoxy, amino, alkylamino, dialkylamino, aminoalkyl, dialkylaminoalkyl, arylamino, aminoaryl, alkylaminoaryl, acylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, lower thioalkoxy, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

G is selected from the group consisting of $NR^5$, O, S, SO, $SO_2$, $(CH_2)_p$, and CH=CH, wherein p is 0 to 6;

A is selected from the group consisting of $NR^5$, O, S, SO, $SO_2$, $(CH_2)_q$, and CH=CH, q is 0 to 6;

B is selected from the group consisting of $NR^5$, O, S, SO, $SO_2$, $(CH_2)_v$, and CH=CH, v is 0 to 6;

$R^1$ and $R^2$ may optionally be taken together to form an alicyclic hydrocarbon, heterocyclyl or aromatic hydrocarbon and said optionally formed ring may be optionally substituted with one or more selected from the group consisting of lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, acylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, arnidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, lower thioalkoxy, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^6)$, amidino, and guanidino.

L and Q are independently selected from the group consisting of lower alkylene, lower alkenylene, lower alkynylene, heterocyclyl, cycloalkyl, aromatic hydrocarbon, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 8;

m is 0 to 7;

n is 0 to 5;

M is selected from the group consisting of cycloalkyl, heterocyclyl, aromatic hydrocarbon, O, S, SO, $SO_2$, $SO_2NR^5$, $NR^5SO_2$, $NR^5$, $POOR^5$, $PON(R^5)_2$, $POOR^5NR^5$, $NR^5POOR^5$, C(O), C(O)O, Se, SeO, $SeO_2$, $C(O)NR^{13}$, and $SiE_2$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

E is lower alkyl or aryl;

L and $R^2$ may be taken together to form a lower alkylidene;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxyl;

X is selected from the group consisting of O, S, C(=O), C(=S), C=C($R^{11}$)2, S(=O), $SO_2$, and C($R^{11}$)$_2$;

Y is a bond, or is selected from the group consisting of O, S, C(=O), C(=S), C=C($R^{11}$)$_2$, S(=O), $SO_2$, and C($R^{11}$)$_2$;

Z is selected from the group consisting of O, S, C(=O), C(=S), C=C($R^{11}$)$_2$, S(=O), $SO_2$, and C($R^{11}$)$_2$.

More preferred embodiments of the invention are shown in the Claims.

In another broad aspect, the present invention is directed to inhibiting nitric oxide synthesis in a subject in need of such inhibition or treatment by administering a compound of Formulas I and II which preferentially inhibits the inducible isoform of nitric oxide synthase over the constitutive isoform of nitric oxide synthase, in a nitric oxide synthesis inhibiting amount to such subject.

The invention further relates to a pharmaceutical composition comprising a compound from Formulas I and II.

Conditions in which there is an advantage in inhibiting NO production from L-arginine in disorders mediated by nitric oxide include amongst others, disorders involving systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, for example arthritis or inflammatory bowel disease, cardiovascular ischemia, diabetes, congestive heart failure, myocarditis, artherosclerosis, migraine, reflux esophagitis, diarrhea, irritable bowel syndrome, cystic fibrosis, emphysema, hyperalgesia (allodynia) cerebral ischemia (both focal ischemia, thrombotic stroke and global ischemia, secondary to cardiac arrest) and other CNS disorder mediated by NO, including opiate tolerance in patients needing protracted opiate analgesics, benzodiazepine tolerance in patients taking benzodiazepines, and other addictive behaviors for example nicotine and eating disorder.

The present invention includes compounds of Formulas I and II in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulfuric, citric, tartaric, phosphoric, lactic, acetic, succinic, fumaric, maleic, methanesulfonic, ethanesulfonic, p-toluenesulfonic, benzenesulfonic and the like. (See, for example, S. M. Berge et al., Pharmaceutical Salts, *J. Pharm. Sci.*, 1977, 66, 1–19.) Salts of the compounds of Formula I can be made by reacting the appropriate compound in the form of the free base with the appropriate acid.

While it may be possible for the compounds of Formulas I and II to be administered as the raw chemical, it is preferable to present them as a pharmaceutical formulation. According to a further aspect, the present invention provides a pharmaceutical formulation comprising a compound of Formulas I and II or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, inhalation, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of Formulas I and II or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Formulations for inhalation administration where the active ingredient is inhaled into the lungs either as a mist or co-administered with an inert carrier agent.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of Formulas I and II are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

The term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" or "cycloalkyl" means a aliphatic radical in a ring with 3 to about 10 carbon atoms, and preferably from 3 to about 6 carbon atoms.

Examples of suitable alicyclic radicals include cyclopropyl, cyclobutyl, cyclopentyl, cyclohexyl, cyclohexenyl and the like.

The term "aromatic hydrocarbon" means and unsaturated cyclic or plycyclic radical with 4 to about 16 carbon atoms, preferably 6 to about 12 carbon atoms, more preferably 6 to about 10 carbon atoms. Examples of suitable aromatic hydrocarbon radicals include phenyl, naphthyl, thienyl, furanyl, pyridinyl, (is)oxazoyl and the like.and the like.

The term "DCM" means dichloromethane.

The term "DEAD" means diethyl azodicarboxylate.

The term "DIBAL-H" means diisobutylaluminum hydride.

The term "DMAP" means dimethylaminopyridine.

The term "DMSO" means dimethylsulfoxide.

The term "EDC" means 1-(3-dimethylaminopropyl)-3-ethylcarbodiimide hydrochloride.

The term "heterocyclyl" means a saturated or unsaturated cyclic hydrocarbon radical including aromatic systems with 4 to about 10 carbon atoms, preferably about 5 to about 6; wherein 1 to about 4 carbon atoms are replaced by nitrogen, oxygen, sulfur, or carbonyl. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, isoxazolyl, thiazolyl, imidazolyl, indolyl, thienyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolinyl, isothiazolyl, oxadiazolyl, triazolyl, thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, triazinyl, 1,3,5-trithianyl, benzo(b)thiophenyl, benzimidazolyl, quinolinyl, and the like.

The term "HOBT" means N-hydroxybenzotriazole.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "lower thioalkoxy", alone or in combination, means an alkyl thioether radical wherein the term alkyl is as defined above and most preferably containing 1 to about 4 carbon atoms. Examples of suitable alkyl thioether radicals include thiomethoxy, thioethoxy, thio-n-propoxy, thio-i-propoxy, thio-n-butoxy, thio-iso-butoxy, thio-sec-butoxy, thio-tert-butoxy and the like.

The term "alkoxycarbonyl" as used herein means an alkoxy group, as defined above, having a carbonyl (C=O) group attached.

The term "halogen" means fluorine, chlorine, bromine or iodine.

The term "MCPBA' means m-chloroperbenzoic acid.

The term "NMM" means N-methylmorpholine.

The term "NMMO" means 4-methylmorpholine N-oxide.

The term "prodrug" refers to a compound that is made more active in vivo.

The term "sulfinyl" means SO.

The term "sulfonyl" means $SO_2$.

The term "TEA" means triethylamine.

The term "$TMSN_3$" means azidotrimethylsilane.

As used herein, reference to "treatment" of a patient is intended to include prophylaxis.

All references, patents or applications, U.S. or foreign, cited in the application are hereby incorporated by reference as if written herein.

Compounds of the present invention can exist in geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Without further elaboration, it is believed that one skilled in the art can, using the preceding description, utilize the present invention to its fullest extent. Therefore, the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous $Na_2SO_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2 N in MeOH, or 6 N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56_C or 78_C. $^1$H NMR spectra were obtained from either General Electric QE-300 or Varian VXR 400 MHz spectrometer with tetramethylsilane as an internal standard. $^{13}$C NMR were obtained from a Varian spectrometer at 125.8 MHz with tetramethylsilane as an internal standard.

SCHEMES

Disclosed are twenty two general synthetic processes useful in the preparation of the compounds of the present invention.

Scheme 1

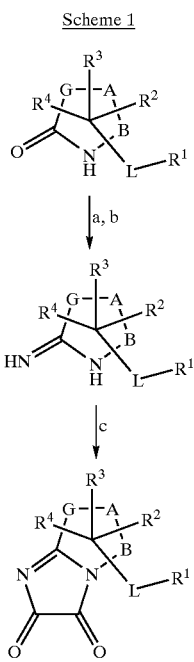

a) $Me_3O^+BF_4^-$. b) $NH_4Cl$. c) oxalyl chloride/pyridine.

Scheme 2

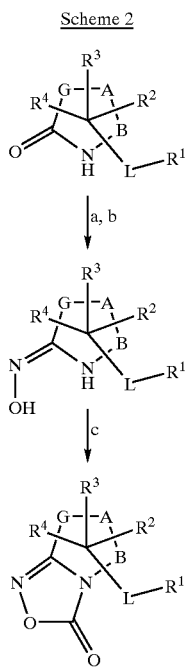

a) $Me_3O^+BF_4^-$. b) $NH_2OH.HCl$. c) carbonyl diimidazole (CDI)

Scheme 3

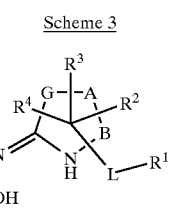

a) thiocarbonyl diimidazole (TCDI). b) DBU.

Scheme 4

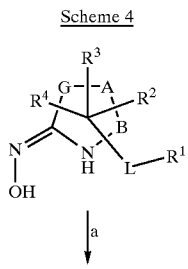

a

-continued
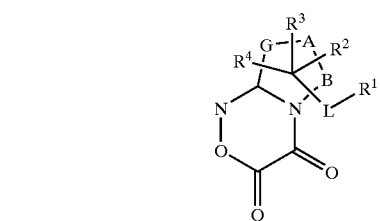
a) oxalyl chloride/pyridine.
Scheme 5
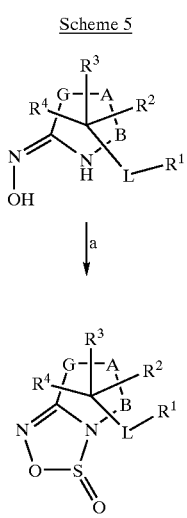
a) thionyl chloride/pyridine.
Scheme 6
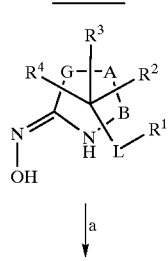
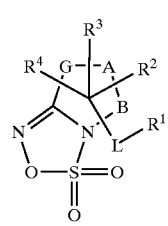
a) sulfuryl chloride/pyridine.
Scheme 7
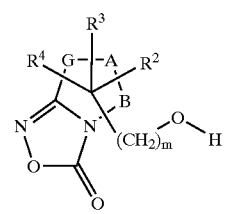
↓a
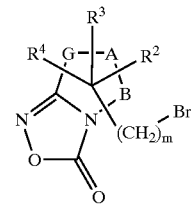
↓b, c
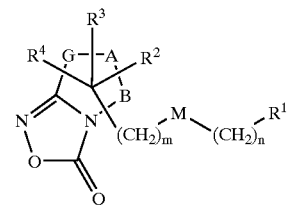
a) CBr$_4$, P(Ph)$_3$
b) H—M—(CH$_2$)$_n$—R$^1$, base [where M = O or S]
c) H$_2$O$_2$ [where M = S].
Scheme 8
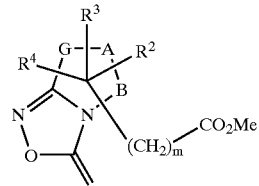
↓a, b
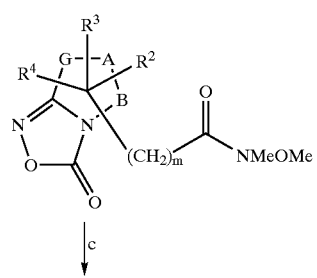
↓c

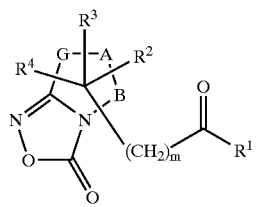
a) KOH, THF. b) NHMeOMe.HCl, WSCD, HOBT, TEA, in DMF or other carboxylic acid activating groups. c) Allyl-MgBr or other nucleophiles.
Scheme 9
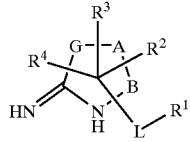
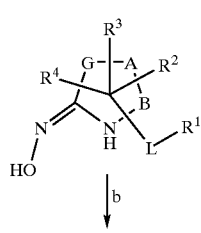
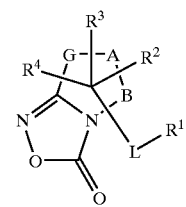
a) potassium t-butoxide/hydroxylamine hydrochloride/ethanol b) CDI.
Scheme 10
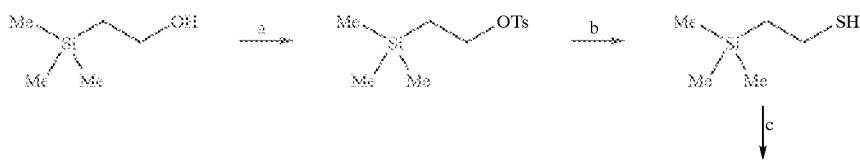
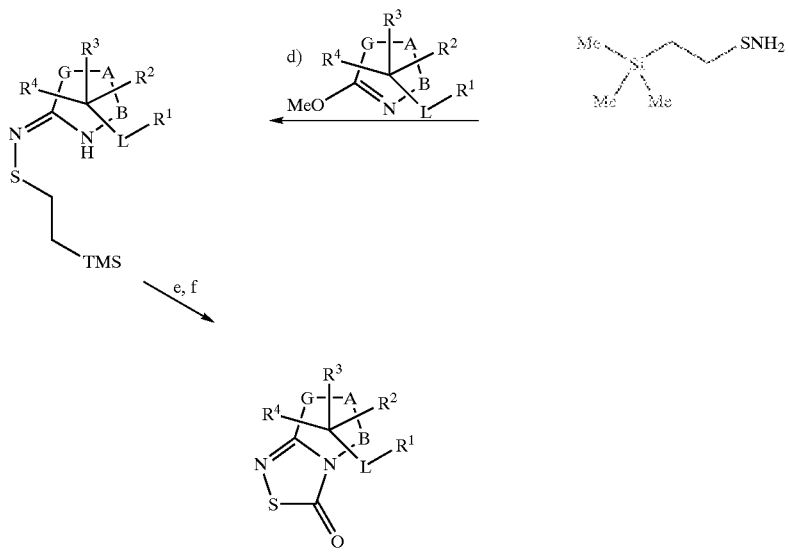
a) Tosyl chloride/pyridine;
b) NaSH;
c) $NH_2Cl$;
d) iminoether product from Example 31;
e) anh $Bu_4N^+F^-$;
f) CDI Scheme 11

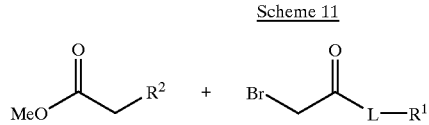

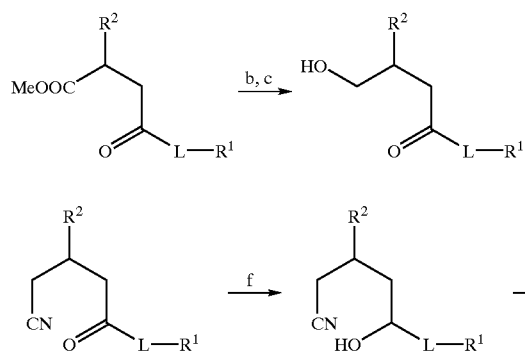

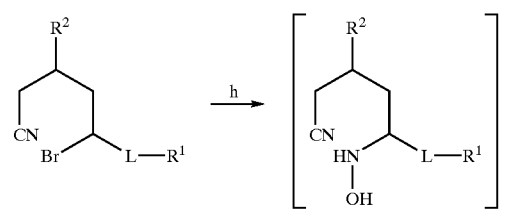

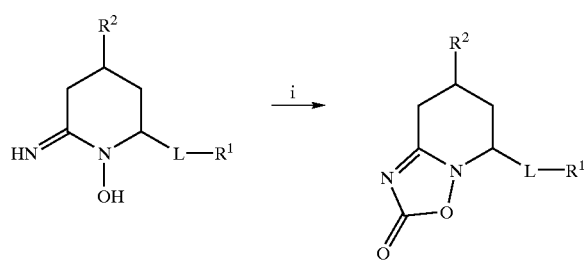

a) Lithium diisopropylamide/THF;
b) LiOH/MeOH;
c) $BH_3$/THF;
d) MsCl/pyridine;
e) KCN/DMSO [TOXIC DANGER];
f) Al(i-Pro$^-$)$_3$;
g) $CBr_4$/Triphenylphosphine;
h) $H_2$NOH HCl;
i) CDI.

Scheme 12

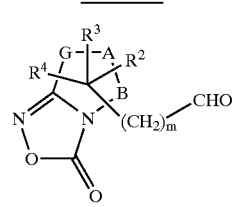

↓a

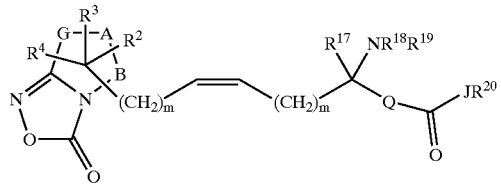

↓b

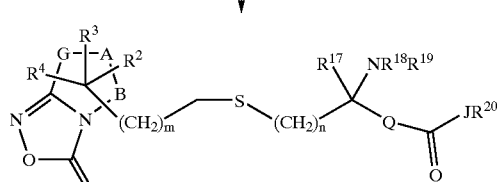

a) Br$^-$P$^+$Ph$_3$CH$_2$(CH$_2$)$_n$C(NR$^{18}$R$^{19}$)R$^{17}$QC(O)JR$^{20}$, base  b) hydrogenation Scheme 13

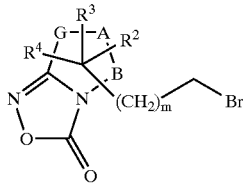

↓a

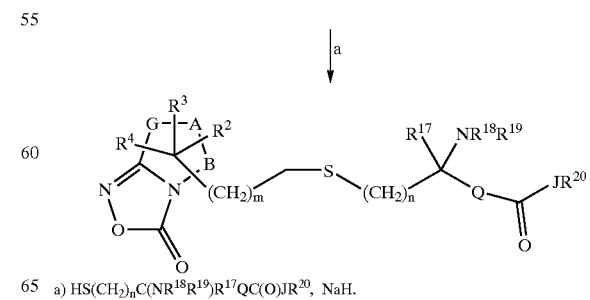

a) NHR$^5$(CH$_2$)$_n$C(NR$^{18}$R$^{19}$)R$^{17}$QC(O)JR$^{20}$, NaCNBH$_3$

Scheme 14

(structure with (CH$_2$)$_m$Br)

↓a (final structure with S linker)

a) HS(CH$_2$)$_n$C(NR$^{18}$R$^{19}$)R$^{17}$QC(O)JR$^{20}$, NaH.

Scheme 15
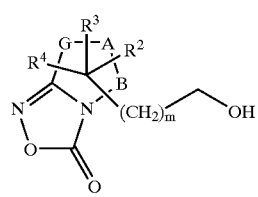
↓ a
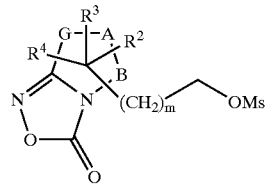
↓ b
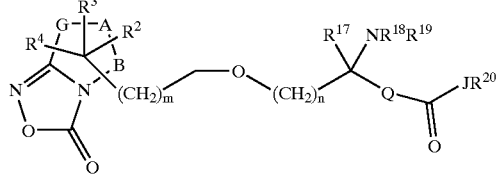
a) MeSO₂CL  b)HO (CH₂)ₙC(NR¹⁸R¹⁹)R¹⁷QC(O)JR²⁰, NaH.
Scheme 16
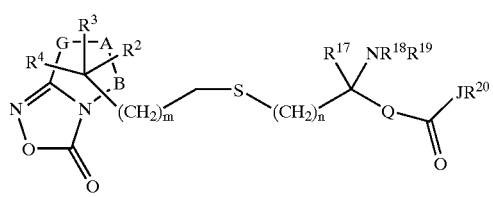
↓ a
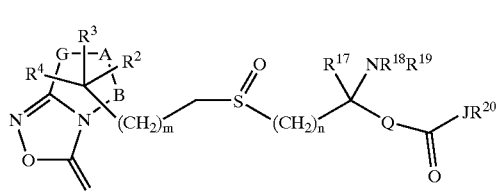
↓ b
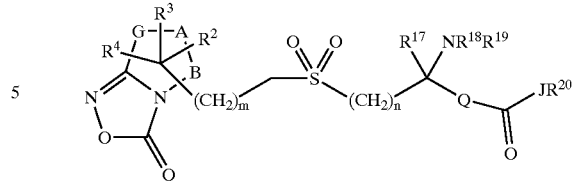
a) hydrogen peroxide, b) hydrogen peroxide, heat
Scheme 17
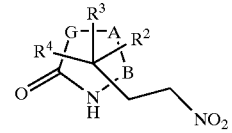
↓ a
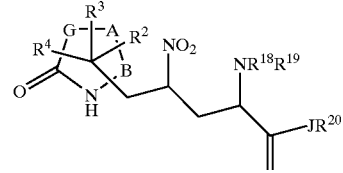
↓ b
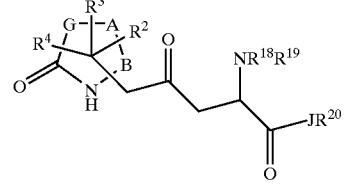
↓ c
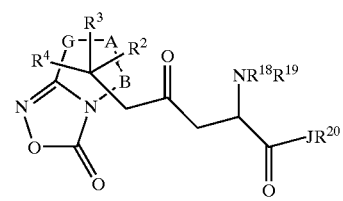
a) CH₂=CHC(NR¹⁸R¹⁹)C(O)JR²⁰, tetramethylguanidine. b) Nef Reaction c) By the method of Scheme 2.
Scheme 18
↓ a

Scheme 21

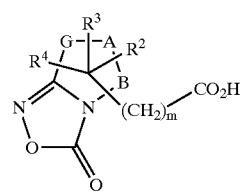

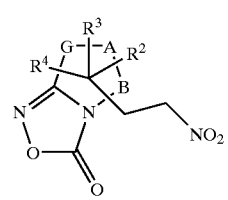

a) NH$_2$CH$_2$(CH$_2$)$_n$C(NR$^{18}$R$^{19}$)R$^{17}$QC(O)JR$^{20}$, CDI

Scheme 22

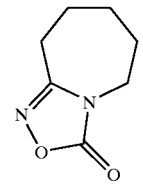

a) CH$_2$=CHC(O)JR$^{20}$, K$_2$CO$_3$, DMF

EXAMPLE 1

6,7,8,9-tetrahydro-3H,5H-[1,2,4]oxadiazolo[4,3-a]azepin-3-one

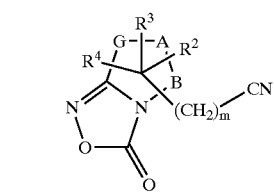

To a solution of 2 g (16 mmol) of 2-hydroximinohomopiperidine (Maybridge) in 20 mL of methylene chloride (CH$_2$Cl$_2$) was added 2.5 g (16 mmol) of 1,1'-carbonyldiimidazole (CDI). This was stirred at 25° C. for six days. This solution was diluted with CH$_2$Cl$_2$, washed -continued

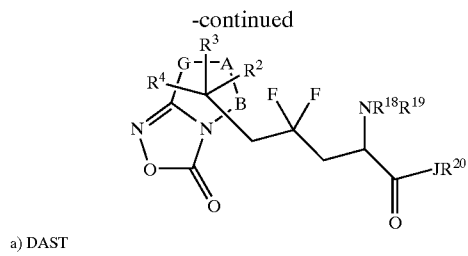

a) DAST

Scheme 19

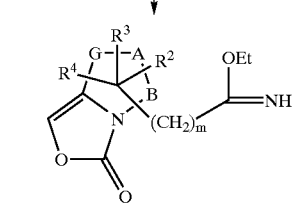

a) methylphosphonium bromide, n-BuLi

Scheme 20

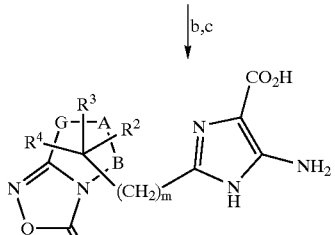

a) HCl, EtOH  b) ethyl aminocyanoacetate, CHCl$_3$  c) 10% HCl with water, dried (MgSO$_4$), filtered and concentrated to afford 2.2 g (89% yield) of the title compound as a white semi-solid. Mass Spectra for C$_7$H$_{10}$N$_2$O$_2$: M$^+$H155. $^1$H NMR,(CDCl$_3$) d 1.5–1.9 (m, 6H), 2.6 (dd, 2H), 3.6 (dd, 2H). $^{13}$C NMR (CDCl$_3$) d 25.3, 26.0, 28.2, 30.2, 43.7, 159.1, 161.6.

EXAMPLE 2

1,1-dimethylethyl[2-(6,7,8,9-tetrahydro-3-oxo-3H, 5H-[1,2,4]oxadiazolo[4,3-a]azepin-5-yl)ethyl] carbamate

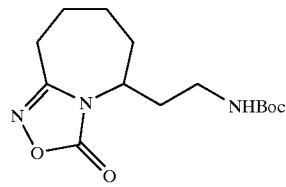

Ex-2a)

A mixture of sodium acetate (6.4 g, 78 mmol) and acetic anhydride (30 mL, 330 mmol) was stirred at 0–5° C. To this slurry was added 2-nitroethanol (30 g, 280 mmol) dropwise over a period of approximately 1 hour. After the 2-nitroethanol addition, the orange reaction mixture was stirred at 0–5° C. for an additional hour and then at ambient temperature for approximately 70 min, the exotherm of the reaction increased the temperature to 30° C. and the mixture was cooled with an ice bath to 20° C. The reaction was then stirred at ambient temperature under N$_2$ overnight. The reaction mixture was diluted with ethyl acetate (EtOAc, 40 mL) and saturated brine (80 mL). The layers were separated and the bottom aqueous layer was extracted again with ethyl acetate (25 mL). The combined ethyl acetate layers were washed once with saturated brine (50 mL), dried (MgSO$_4$), filtered and concentrated to afford 38 g of 2-nitroethylacetate as a reddish orange oil.

Ex-2b)

To a solution of 1-morpholino-1-cyclohexene (51 g; 300 mmol) in 120 mL anhydrous acetonitrile at 0–4° C. was added the 2-nitroethylacetate product of Example 2a (37.8 g, 293 mmol) dropwise. The resulting red solution was stirred under N$_2$ atmosphere in an ice bath for 2½ hrs. The red solution was then stirred at ambient temperature under an N$_2$ atmosphere overnight. Water (100 mL) was added to the red solution over a 10–15 minute period. The temperature rose from 20 to 29° C. with the first 200 mL of water, but then dropped to 27° C. by the end of the addition. This was then acidified with aqueous HCl. The dark red reaction mixture was diluted with 85 mL of EtOAc and the layers separated. The light orange water layer (bottom) was extracted again with 50 mL of EtOAc. The combined EtOAc layers were washed with saturated brine (2×85 mL), dried (MgSO$_4$), filtered and concentrated to afford 45 g of 2-(2-nitroethyl) cyclohexanone as a red oil.

Ex-2c)

To a solution of hyroxylamine-O-sulfonic acid (9.9 g; 86 mmol) in 17 mL of 96% formic acid was added the product of Example 2b (13.7 g; 88 mmol) in 5 mL of 96% formic acid dropwise at 60–65° C. over a period of 65 minutes. After the addition, the temperature was slowly raised in 10° C. increments. An exotherm was observed at around 85–90° C. After the exotherm subsided (35 min), the dark brownish red mixture was heated gently at reflux for 1 hr. After cooling to room temperature, the dark brown red reaction mixture was slowly poured into water. The solution was cooled to produce a heavy precipitate. Filtration afforded 5.7 g of 7-(2-nitroethyl)caprolactam as a brown solid. mp=140–141° C.

Ex-2d)

The product of Example 2c was allowed to react with palladium black and ammonium formate in methanol to afford 2-(2-aminoethyl)caprolactam.

Ex-2e)

The product of Example 2d was allowed to react with Boc anhydride to afford 2-(2-Boc-aminoethyl)caprolactam.

Ex-2f)

A portion of the product of Example 2e (1 g, 4 mmol) was allowed to react with 0.74 g (5 mmol) of trimethyloxonium tetrafluoroborate in 25 mL CH$_2$Cl$_2$ over a 16 hour period. The mixture was diluted with 100 mL CH$_2$Cl$_2$ and washed with 2×50 mL 5% NaHCO$_3$ and 100 mL brine. The organic phase was dried over MgSO$_4$, filtered and the solvent was evaporated in vacuo to afford the iminoether.

Ex-2 g)

The product of Example 2e (0.67 g, 2.48 mmol) was allowed to react with 0.207 g (3 mmol) of hydroxylamine hydrochloride in 25 mL MeOH for 16 hours. The methanol was evaporated to afford the hydroxamidine as an oil.

Ex-2)

The product of Example 2 g was allowed to react with 0.49 g (3 mmol) of 1,1'-carbonyldiimidazole in 25 mL of CH$_2$Cl$_2$ for 24 hours at room temperature. The title compound is isolated from the reaction mixture using C$_{18}$ reverse phase HPLC (10–50% acetonitrile gradient in 30 minutes).

EXAMPLE 3

5-(2-aminoethyl)-6,7,8,9-tetrahydro-3H,5H-[1,2,4] oxadiazolo[4,3-a]azepin-3-one, mono (trifluoroacetate)

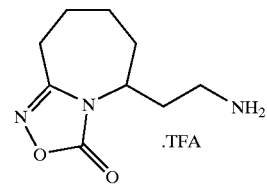

Ex-3)

The product of Example 2 was treated with 10 mL trifluoroacetic acid for 15 minutes to remove the Boc-protecting group. The solvent was evaporated in vacuo and title compound was isolated via C$_{18}$ reversed phase HPLC (0–40% acetonitrile gradient in 30 minutes) to yield 100 mg of the title material. Mass Spectra for C$_{11}$H$_{16}$F$_3$N$_3$O$_4$: M$^+$H= 198. $^1$H NMR (D$_2$O): d 1.25–2.20 (m; 8H), 2.48–2.62 (m; 1H), 2.75–3.04 (m; 3H), 4.10–4.22 (m; 1H). Elemental analysis for C$_7$H$_{10}$N$_2$O$_2$: Calcd. C, 42.45 H, 5.18N, 13.50 Found: C, 40.93 H, 5.43 N, 11.91.

EXAMPLE 4 methyl 6,7,8,9-tetrahydro-3-oxo-3H,5H-[1,2,4]oxadiazolo[4,3-a]azepine-5-carboxylate

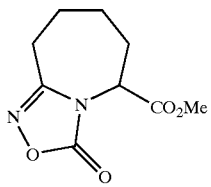

Ex-4a)

To a solution of 7-methylcarboxylate caprolactam (9.78 g, 57 mmol) in $CH_2Cl_2$ at room temperature was added trimethyloxonium tetrafluoroborate (9.30 g, 63 mmol). This solution was stirred for 16 hours at 25° C. The solution was then washed twice with sodium bicarbonate and twice with brine, dried over magnesium sulfate and stripped of all solvent under reduced pressure to yield the iminoether as a light yellow colored oil. Mass Spectra of $C_9H_{15}N_1O_3$: $M^+H=186$. $^1H$ NMR (CDCl3) d 3.96–3.98 (d, 1H), 3.6 (s, 3H), 3.5 (s, 3H) 2.2–2.3 (m, 2H), 1.8–1.9 (m, 2H), 1.4–1.5 (m, 4H), 1.1–1.2 (m, 1). $^{13}C$ NMR (CDCl3) d 174.5, 168.9, 61.7, 52.7, 51.8, 32.2, 30.9, 29.6, 22.9.

Ex-4b)

To a solution of the product of Example 4a in methanol was added hydroxylamine hydrochloride (4.81 g, 69 mmol). The solution was stirred for 6 hours before the solvent was removed under pressure to yield the oxime. Mass Spectra for $C_8H_{14}N_2O_3$: $M^+H=187$. $^{13}C$ NMR (CDCl3) d 170.4, 162.9, 56.9, 53.5, 32.0, 28.4, 25.0, 23.5.

Ex-4)

To a solution of the product of Example 4b in $CH_2Cl_2$ was added CDI (11.2 g, 69 mmol). This solution was stirred for 16 hours at 25° C. The solution was then washed twice with potassium hydrogen sulfate and twice with brine. All solvent was removed under reduced pressure to yield the title compound. Mass Spectra for $C_9H_{12}N_2O_4$: $M^+H=212$. $^{13}C$ NMR (CDCl3) d 169.2, 161.0, 159.1, 56.2, 53.3, 30.6, 26.6, 26.3, 25.0.

EXAMPLE 5

6,7,8,9-tetrahydro-5-(hydroxymethyl)-3H,5H-[1,2,4]oxadiazolo[4,3-a]azepin-3-one

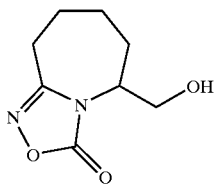

Ex-5)

To a solution of the product of Example 4 in anhydrous THF was added lithium borohydride (21.5 mL, 43 mmol). This solution was stirred for 16 hours at 25° C. The lithium borohydride was quenched with methanol and the solvent was removed under reduced pressure. The residue was dissolved in ethyl acetate, washed twice with potassium hydrogen sulfate and twice with brine. The organic phase was dried over magnesium sulfate and all solvent was removed under reduced pressure to yield the title compound. Mass Spectra for $C_8H_{12}N_2O_3$: $M^+H=184$. $^1H$ NMR (CDCl3) d 4.1–4.2 (m, 1H), 3.8 (d, 2H), 3.1 (s, 1H), 2.8–2.9 (m, 1H), 2.6–2.7 (m, 1H), 2.1–2.2 (m, 1H), 1.9–2.0 (m, 1H), 1.7–1.8 (m, 3H), 1.4–1.6 (m, 1H). $^{13}C$ NMR (CDCL3) d 161.1, 160.1, 62.2, 56.4, 29.5, 25.9, 25.2, 25.0.

EXAMPLE 6

6,7,8,9-tetrahydro-5-(2-propenyl)-3H,5H-[1,2,4]oxadiazolo[4,3-a]azepin-3-one

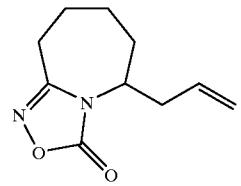

Ex-6a)

A suspension of potassium t-butoxide (200 g, 1.78 mol) in toluene which was cooled to 0° C. in an ice bath under $N_2$ was treated with cyclohexanone (157 g, 1.60 mol). To the reaction mixture was slowly added allyl bromide (194 g, 1.60 mol) over a 2 hour period. The reaction was warmed to room temperature over 5 hours. The reaction was then poured into EtOAc (400 mL) and washed once with 10% potassium hydrogen sulfate (250 mL). The organic solution was then washed with brine (3×200 mL), dried over magnesium sulfate, and evaporated under reduced pressure. The resulting oil was then chromatographed to yield 158.4 g (71.6%) of 2-allyl cyclohexanone as an oil. $^1H$ NMR (CDCl_3, 300 MHz) d 1.2–2.5 (m, 10H), 2.59 (m, 1H), 5.0 (dd, 2H), 5.75 (m, 1H). $^{13}C$ NMR (CDCl_3, 75 MHz) d 25.04, 28.03, 33.46, 33.86, 42.12, 50.35, 116.3, 136.6, 212.5.

Ex-6b)

A solution of the product of Example 6a (56.4 g, 0.408 mol) in formic acid (200 mL) was stirred under $N_2$ for 5 minutes. To this solution was added hydroxylamine-O-sulfonic acid (53.0 g, 0.448 mol). The reaction was stirred at reflux for 45 minutes before the solvent was removed under reduced pressure. Ethyl acetate was poured into the resulting black slurry and the mixture was neutralized with a solution of saturated sodium bicarbonate until the evolution of gas ceased. The organic layer was separated, washed with brine (3×150 mL), dried over magnesium sulfate and stripped of solvent under reduced pressure. The resulting dark brown solid was chromatographed with 1:1 ethyl acetate:hexane to afford 18.5 g (30%) of the lactam as a cream colored solid. $^1H$ NMR (CDCl_3, 300 MHz) d 1.25 (m, 2H), 1.42 (m, 2H), 1.86 (m, 2H), 2.15 (m, 2H), 2.33 (m, 2H), 3.28 (m, 2H), 5.04 (dd, 2H), 5.64 (m, 1H) 6.07 (bs, 1H). $^{13}C$ NMR (CDCl_3, 75 MHz) d 23.30, 29.87, 35.51, 37.14, 40.66, 53.05, 118.9, 134.1, 177.9.

Ex-6c)

A solution of the product of Example 6b (20 g, 0.130 mol) in $CH_2Cl_2$ (200 mL) was stirred under a blanket of $N_2$ for 5 minutes. To the solution was added trimethyloxonium tetrafluoroborate (20 g, 0.135 mol). The reaction was stirred at reflux for 2 hours while being monitored by thin layer chromatography and then cooled to room temperature. The reaction was neutralized with a solution of saturated sodium bicarbonate. The organic layer was separated, washed with brine (3×100 mL), and dried over magnesium sulfate before all solvent was removed under reduced pressure to afford 20 g of the iminoether as an oil.

Ex-6d)

To a solution of the product of Example 6c (~20 g) in methanol (200 mL) under $N_2$ was added hydroxylamine hydrochloride (22.2 g, 0.154 mol). The reaction was brought to reflux and stirred at reflux for 2 hours before it was cooled to room temperature. The solvent was removed under reduced pressure and toluene was added to the oil residue. The toluene was then removed under reduced pressure to afford 20 g of the hydroxamidine as a cream colored solid.

Ex-6)

To a solution of the product of Example 6d (~20 g) in CH$_2$Cl$_2$ (200 mL) under N$_2$ was added 1,1'-carbonyldiimidazole (22.7 g, 0.140 mol) portionwise. The reaction was then stirred for 1 hour. To the reaction was added an additional portion of the 1,1'-carbonyldiimidazole (1 g, 0.00617 mol) to insure all starting material had reacted. To the reaction was then added a solution of 10% potassium hydrogensulfate (200 mL). The organic was separated, washed with brine (3×100 mL), dried over magnesium sulfate and stripped of all solvent under reduced pressure. The resulting solid was chromatographed (silica gel) with 1:1 ethyl acetate:hexane to afford the title compound 8.0 g (31.5%). $^1$H NMR (CDCl$_3$, 300 MHz) d 1.50–2.25 (m, 6H), 2.51 (m, 4H), 2.87 (dd, 2H), 4.29 (m, 1H), 5.05 (dd, 2H), 5.75 (m, 1H). $^{13}$C NMR (CDCl$_3$, 75 MHz) d 23.97, 25.66, 26.32, 31.22, 36.52, 53.45, 119.1, 133.0, 159.7, 160.7.

EXAMPLE 7

5-ethyl-6,7,8,9-tetrahydro-3H,5H-[1,2,4]oxadiazolo[4,3-a]azepin-3-one

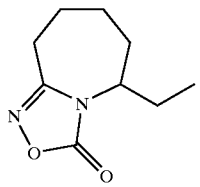

Ex-7a)

A sample of 7-ethylcaprolactam (5 g, 35.4 mmol) was allowed to react with 6.8 g (46.0 mmol) of trimethyloxonium tetrafluoroborate in 120 mL CH$_2$Cl$_2$ over a 5 day period. The product iminoether (4.2 g) was obtained as a pale yellow oil from the reaction mixture by the methods of Example 2f.

Ex-7b)

The product of Example 7a (4.2 g, 27.0 mmol) was allowed to react with 1.9 g (27.0 mmol) of hydroxylamine hydrochloride in 40 mL MeOH for 24 hours. The hydroxamidine product was obtained as an oil by the methods of Example 2g.

Ex-7)

The product of Example 7b is allowed to react 1,1'-carbonyldiimidazole in CH$_2$Cl$_2$ for 24 hours at room temperature and the title compound is isolated from the reaction mixture using C$_{18}$ reverse phase HPLC as described in Example 2.

EXAMPLE 8

6,7,8,9-tetrahydro-3-oxo-3H,5H-[1,2,4]oxadiazolo[4,3-a]azepine-5-acetaldehyde

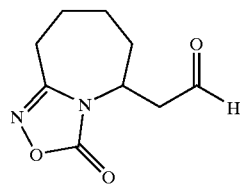

Ex-8)

To a solution of the product of Example 6 in dioxane (200 mL) and water (135 mL) was added sodium periodate (15.11 g, 0.071 mol) and osmium tetraoxide (12 drops of a 1 ppm solution of osmium dioxide in n-BuOH/H$_2$O). The reaction was stirred at room temperature and monitor by thin layer chromatography for one day. Since the starting material had not completely reacted, additional osmium tetraoxide (12 drops of 1 ppm solution of osmium dioxide in n-BuOH/H$_2$O) was added. A white precipitate was filtered off and the filtrate was removed under reduced pressure to the point where no dioxane remained. Additional water (75 mL) was then added to the aqueous layer and this aqueous mixture was washed with CH$_2$Cl$_2$ (3×75 mL). The organic layer was combined, dried over magnesium sulfate, and stripped of all solvent under reduced pressure to afford a yellow oil. Chromatographic (silica gel) purification of this material eluting with the 1:1, ethyl acetate:hexane afforded 4.0 g (67%) of the title compound. $^1$H NMR (CDCl$_3$, 300 MHz) d 1.2–2.5 (m, 6H), 2.59 (q, 2H), 2.92 (m, 2H), 4.79 (m, 1H), 9.79 (ss, 1H). $^{13}$C NMR (CDCl$_3$, 75 MHz) d 24.12, 31.52, 32.00, 45.61, 49.10, 53.98, 159.9, 160.8, 198.1.

EXAMPLE 9

6,7,8,9-tetrahydro-5-(2-hydroxyethyl)-3H,5H-[1,2,4]oxadiazolo[4,3-a]azepin-3-one

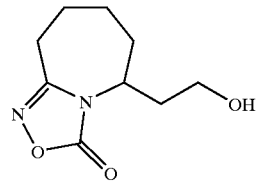

To a solution of the product of Example 8 (3.0 g, 0.015 mol) in tetrahydrofuran (20 mL) was added a borane. THF complex (20 mL, 0.020 mol). The reaction stirred for 2 hours upon which methanol (19 mL) was added. The solvent was removed under reduced pressure. The resulting oil was partioned between CH$_2$Cl$_2$ (40 mL) and water (2×20 mL). The organic layer was dried over magnesium sulfate and all solvent was removed under reduced pressure. The residue was chromatographed eluting with 1:1 ethyl acetate/hexane to produce 2.1 g (69%) of the title material. $^1$H NMR (CDCl$_3$, 300 MHz) d 1.18–2.15(m, 8H), 3.59(m, 2H), 4.39 (m, 1H). $^{13}$C NMR (CDCl$_3$, 75 MHz) d 24.45, 25.71, 26.47, 32.56, 34.67, 51.16, 58.85, 160.66, 160.89.

EXAMPLE 10 ethyl 4,5-dihydro-5-[(6,7,8,9-tetrahydro-3-oxo-3H,5H-[1,2,4]oxadiazolo[4,3-a]azepin-5-yl)methyl]-3-isoxazolecarboxylate

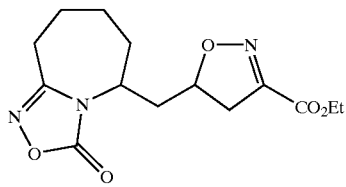

To a solution of 0.5 g (2.6 mmol) of the product of Example 6 in 100 mL of toluene was added 0.8 g (5.2 mmol) of ethyl chlorooximidoacetate (Aldrich). This solution was brought to reflux and stirred for 18 hours. All solvent was removed in vacuo and the residue purified via C-18 chromatography (0–60% acetonitrile/water, 25 min.) with the product eluting at 54% acetonitrile. Concentration of the relevant fractions afforded 0.6 g (75% yield) of the title compound as a pale yellow oil. Mass Spectra for $C_{14}H_{19}N_3O_5$: $M^+H=310$. $^1H$ NMR (CDCl$_3$) d 1.3 (t, 3H), 1.5 (bt, 1H), 1.7–2.2 (m, 7H), 2.5 (m, 1H), 2.8–3.0 (m, 2H), 3.3–3.5 (m, 1H), 4.3 (q, 2H), 4.4 (m, 1H), 4.8 (m, 1H). Elemental analysis for $C_{14}H_{19}N_3O_5 + 0.25\ H_2O$: Calcd: C, 53.58 H, 6.26 N, 13.39. Found: C, 53.93 H, 6.16 N, 13.13.

EXAMPLE 11

6,7,8,9-tetrahydro-5-(3-hydroxypropyl)-3H,5H-[1,2,4]oxadiazolo[4,3-a]azepin-3-one

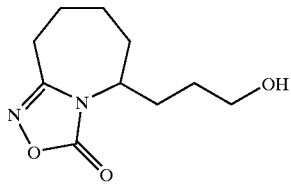

A solution of the product of Example 6 (3.0 g, 0.0155 mol) in tetrahydrofuran (44 mL) under nitrogen was treated with a Borane.THF complex (1M, 18.56 mL) and this reaction was stirred for 2 hours. Methanol (2.50 mL) was added before a solution of saturated sodium bicarbonate (2.32 mL) and hydrogen peroxide (30%, 2.32 mL) were added resulting in a white precipitate. The precipitate was filtered off and the solvent was removed from the filtrate under reduced pressure to afford the title compound. $^1H$ NMR (CDCl$_3$, 300 MHz) d 1.2–2.5 (m, 8H), 2.59 (m, 2H), 2.95 (dd, 2H), 3.72 (m, 2H), 4.25 (m, 1H). $^{13}C$ NMR (CDCl$_3$, 75 MHz) d 23.87, 25.73, 26.23, 28.57, 31.88, 53.97, 61.90, 68.07, 159.9, 160.8.

EXAMPLE 12

5-(3-bromopropyl)-6,7,8,9-tetrahydro-3H,5H-[1,2,4]oxadiazolo[4,3-a]azepin-3-one

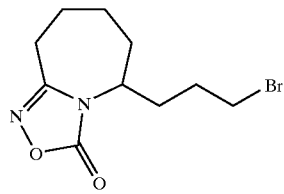

To a solution of the product of Example 11 in methylene chloride at 0° C. is added carbon tetrabromide and triphenylphosphine. The reaction is stirred for 2 hours and the solvent is removed under reduced pressure. The crude product is dissolved in an eluting solvent system and chromatographed to afford the title compound.

EXAMPLE 13

(E)-5-(2-butenyl)-6,7-dihydro-3H,5H,9H-[1,2,4]oxadiazolo[3,4-c][1,4]oxazepin-3-one

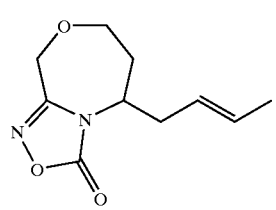

Ex-13a)

A solution of 55 g (550 mmol) of tetrahydropyran-4-one (Aldrich) and 50.4 mL (600 mmol) of pyrrolidine in benzene was stirred at reflux for three hours while collecting and removing the separated water in a Dean-Stark trap. This solution was allowed to cool to room temperature and was used without further purification in the following step.

Ex-13b)

To the product solution from Example 13a was added dropwise one equivalent of crotyl iodide in benzene. An exotherm to 55° C. was noted and a precipitate formed. The reaction was stirred for 18 hours, diluted with 500 mL of water and stirred for an additional two hours. The organic layer was separated and the aqueous layer was extracted with ethyl acetate. The combined organic extracts were dried (MgSO$_4$), filtered and concentrated to afford a yellow oil. Distillation (60–80° C., 0.1 torr) of this material afforded 40.9 g (48%) of the 2-(2-butenyl)tetrahydropyran-4-one as a colorless oil.

Ex-13c)

The product of Example 13b (40.9 g, 266 mmol) was dissolved in 150 mL of formic acid. To this solution was added 33.9 g (300 mmol) of hydroxylamine-O-sulfonic acid. This was stirred at reflux for one hour. After cooling the reaction to room temperature it was partitioned between water and methylene chloride. The organic layer was separated, dried (MgSO$_4$), filtered and concentrated to afford 27.1 g of an oily solid. This material was purified via silica gel chromatography eluting with 30% acetone/hexanes to yield 12.6 g (28% yield) of the lactam.

Ex-13d)

The product of Example 13c (2 g, 10.6 mmol) was dissolved in methylene chloride to which 1.57 g of trimethyloxonium tetrafluoroborate was added. This mixture was stirred at room temperature for two days before it was diluted with aqueous sodium bicarbonate. The separated organic layer was filtered through a pad of silica gel which was washed liberally with ethyl acetate. The combined organic eluant was dried (MgSO$_4$), filtered and concentrated to afford 1.8 g (84%) of the iminoether.

Ex-13e)

The product of Example 13d (1.8 g, 8.9 mmol) was dissolved in 100 mL of ethanol to which 0.6 g (8.6 mmol) of hydroxylamine hydrochloride was added. This reaction was stirred at reflux for twenty four hours. The solvent was then removed in vacuo to afford a tan solid. Crystallization of this crude material afforded 1.25 g (66%) of the hydroxamidine as an amber solid.

Ex-13)

The product of Example 13e (1.25 g, 6.8 mmol) was dissolved in 25 mL of CH$_2$Cl$_2$ to which 1.1 g (7 mmol) of carbonyl diimidazole was added. This mixture was stirred overnight at room temperature. The reaction mixture was then washed with water, dried (MgSO$_4$), filtered and concentrated to afford 1 g of an oil. Purification via C-18 chromatography eluting with an 55% acetonitrile/water mixture afforded 0.6 g (42%) of the desired title product. Mass Spectra for C$_{10}$H$_{14}$N$_2$O$_3$: M$^+$H=211. $^1$H NMR (CDCl$_3$) d 1.8 (d, 3H), 2.4–2.6 (m, 2H), 2.8–3.1 (m, 2H), 3.55 (m, 2H), 4.0 (m, 1H), 4.1 (m, 2H), 5.3 (m, 1H), 5.6 (m, 1H). $^{13}$C NMR (CDCl$_3$) 17.7, 29.0, 33.9, 56.4, 68.4, 72.2, 124.0, 130.1, 158.0, 158.8. Elemental analysis for C$_{10}$H$_{14}$N$_2$O$_3$+0.2 H$_2$O:

| Calcd. C, 56.17 | H, 6.79 | N, 13.10 |
| Found C, 56.45 | H, 6.95 | N, 12.84 |

EXAMPLE 14

9-ethyl-6,7,8,9-tetrahydro-3H,5H-[1,2,4]oxadiazolo[4,3-a]azepin-3-one

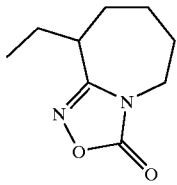

Ex-14a)

A sample of 3-ethylcaprolactam (5 g, 35.4 mmol) was allowed to react with 6.8 g (46.0 mmol) of trimethyloxonium tetrafluoroborate in 140 mL CH$_2$Cl$_2$ over a 5 day period. The product iminoether (4.7 g) was obtained as a pale yellow oil from the reaction mixture by the methods of Example 2f.

Ex-14b)

The product of Example 14a (4.7 g, 30.3 mmol) was allowed to react with 2.19 g (30.3 mmol) of hydroxylamine hydrochloride in 40 mL MeOH for 24 hours. The hydroxamidine product was obtained as an oil by the methods of Example 2g.

Ex-14)

The product of Example 14b is allowed to react 1,1'-carbonyldiimidazole in CH$_2$Cl$_2$ for 24 hours at room temperature and the title compound is isolated from the reaction mixture using C$_{18}$ reversed phase HPLC as described in Example 2.

EXAMPLE 15

5-(bromomethyl)-6,7,8,9-tetrahydro-3H,5H-[1,2,4]oxadiazolo[4,3-a]azepin-3-one

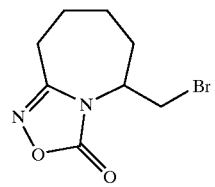

To a solution of the product of Example 5 in dichloromethane was added carbon tetrabromide (460 mg, 1.3 mmol). This solution was cooled in an ice bath and stirred for 5 minutes. Triphenylphosphine (437 mg, 1.6 mmol) was added to the solution and stirring was continued for 5 minutes at 0° C. before allowing it to warm slowly to room temperature. The solvent was removed under reduced pressure. The residue was placed on a filter and washed three times with ether. The filtrate solvent was then removed under reduced pressure to yield the title compound. Mass Spectra for C$_8$H$_{11}$N$_2$O$_2$Br: M$^+$H=246.

EXAMPLE 16

6,7,8,9-tetrahydro-5-(2-nitroethyl)-3H,5H-[1,2,4]oxadiazolo[4,3-a]azepin-3-one

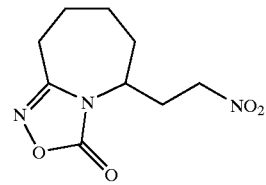

Ex-16a)

The product of Example 2c (5.5 g; 30 mmol) was allowed to react with trimethyloxonium tetrafluoroborate (5 g; 33 mmol) in 50 mL of CH$_2$Cl$_2$. This mixture was stirred for 18 hours before saturated NaHCO$_3$ (50 mL) was added. The mixture was stirred until gas evolution ceased and the pH reached 8. The layers were separated and the organic phase was dried over MgSO$_4$ and concentrated in vacuo to yield 5.8 g of the iminoether as an oil.

Ex-16b)

The product of Example 16a was combined with hydroxylamine hydrochloride (4.2 g, 28 mmol) and ethanol (50 mL) and then stirred at reflux for one hour. The mixture was cooled and concentrated in vacuo. The residue was partitioned between saturated NaHCO$_3$/CH$_2$Cl$_2$. The organic layer was dried over MgSO$_4$ and concentrated in vacuo to afford the hydroxamidine as an oil.

Ex-16)

The product of Example 16b and 1,1'-carbonyldiimidazole (4.5 g; 0.028 mole) dissolved in 50 mL of CH$_2$Cl$_2$ were stirred 18 hours. The reaction mixture was washed with 10% KHSO$_4$ to remove excess imidazole. The organic solution was dried over MgSO$_4$ and concentrated in vacuo. The residue was chromatographed on Merck silica, eluting with 40% EtOAc/hexane. The title compound eluted first off the column and was crystallized upon concentration to yield 3.1 g of a white powder. Mass spectra of C$_9$H$_{13}$N$_3$O$_4$: M$^+$H=228. $^1$H NMR (CDCl$_3$) d 1.4–1.6 (m, 1H); 1.75–1.86 (m, 2H); 1.95–2.19 (m, 3H); 2.28–2.39 (m, 1H); 2.48–2.62 (m, 2H); 2.91–3.01 (ddt, 1H); 4.28–4.38 (m, 1H); 4.38–4.54 (m, 2H).

EXAMPLE 17

4,5-dihydro-5-[(6,7,8,9-tetrahydro-3-oxo-3H,5H-[1,2,4]oxadiazolo[4,3-a]azepin-5-yl)methyl]-3-isoxazolecarboxylic acid

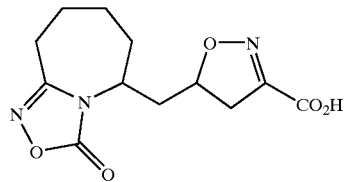

Ex-17)

A solution of 2.2 g (7 mmol) of the product of Example 10 in 80 mL of acetone, 40 mL of water, and 20 mL of conc. HCl was stirred at reflux for three days. All solvent was removed in vacuo. The residue, dissolved in aqueous sodium bicarbonate, was washed with ethyl acetate, acidified with dilute HCl, and extracted with ethyl acetate. The organic extract was dried (MgSO$_4$), filtered and concentrated to afford 1 g (51%) of the title product as a colorless oil. $^1$H NMR (CDCl$_3$) d 1.5 (bt, 1H), 1.8–2.2 (m, 7H), 2.5 (m, 1H), 2.8–3.1 (m, 2H), 3.3–3.5 (m, 1H), 4.45 (m, 1H), 4.9 (m, 1H), 7.9 (bs, 1H).

EXAMPLE 18

5-(3-butenyl)-6,7,8,9-tetrahydro-3H,5H-[1,2,4]oxadiazolo[4,3-a]azepin-3-one

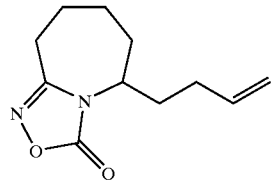

Ex-18a)

A suspension of potassium t-butoxide in toluene cooled to 0° C. in an ice bath under N$_2$ is treated with cyclohexanone. To the reaction mixture is slowly added 3-butenyl bromide. The reaction is warmed to room temperature. The reaction is then poured into EtOAc and washed once with 10% potassium hydrogen sulfate. The organic solution is then washed with brine, dried over magnesium sulfate, and the solvent evaporated under reduced pressure to afford 2-(3-butenyl)cyclohexanone.

Ex-18b)

A solution of the product of Example 18a in formic acid is stirred under N$_2$. To this solution is added hydroxylamine-O-sulfonic acid. The reaction is stirred at reflux, cooled to room temperature, stripped of solvent under reduced pressure. Ethyl acetate is poured into the resulting black slurry and the mixture is neutralized with a solution of saturated sodium. The organic layer is separated, washed with brine, dried over magnesium sulfate and stripped of solvent under reduced pressure to afford the lactam.

Ex-18c)

A solution of the product of Example 18b in CH$_2$Cl$_2$ is stirred under a blanket of N$_2$. To the solution is added trimethyloxonium tetrafluoroborate. The reaction is refluxed while being monitored by thin layer chromatography and then cooled to room temperature. The reaction is neutralized with a solution of saturated sodium bicarbonate. The organic layer is separated, washed with brine, and dried over magnesium sulfate. The solvent is removed under reduced pressure to afford the iminoether.

Ex-18d)

To a solution of the product of Example 18c in methanol under N$_2$ is added hydroxylamine hydrochloride. The reaction is brought to reflux, cooled to room temperature, and stripped of all solvent under reduced pressure to afford the hydroxamidine.

Ex-18)

To a solution of the product of Example 18d in CH$_2$Cl$_2$ under N$_2$ is added 1,1'-carbonyldiimidazole portion-wise. The reaction is then stirred at room temperature. To the reaction is added a solution of 10% potassium hydrogen-sulfate. The organic is separated, washed with brine, dried over magnesium sulfate and stripped of all solvent under reduced pressure to afford the title compound.

EXAMPLE 19

6,7,8,9-tetrahydro-3-oxo-3H,5H-[1,2,4]oxadiazolo[4,3-a]azepine-5-propanal

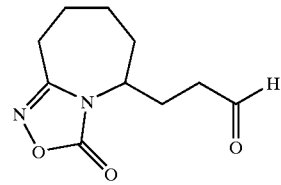

To a solution of the product of Example 18 in dioxane and water is added sodium periodate and osmium tetraoxide. The reaction is stirred at room temperature and monitored by thin layer chromatography. Water is added to the reaction mixture and the solution is extracted with CH$_2$Cl$_2$. The organic layer is dried over magnesium sulfate, filtered, and stripped of all solvent under reduced pressure to afford the title compound.

EXAMPLE 20

5-(2-bromoethyl)-6,7,8,9-tetrahydro-3H,5H-[1,2,4]oxadiazolo[4,3-a]azepin-3-one

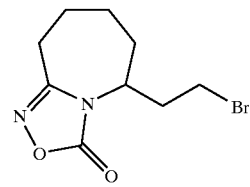

Ex-20)

The product of Example 9 (0.20 g, 0.01 mol) was treated by the methods described in Example 12 to yield 0.21 g (81%) of the title compound. $^1$H NMR (CDCl$_3$, 300 MHz) d 1.50–2.60 (m, 9H), 2.99 (dd, 1H), 3.35 (m, 2H), 4.41 (m, 1H). $^{13}$C NMR (CDCl$_3$, 75 MHz) d 23.89, 25.33, 26.04, 28.06, 31.59, 35.05, 52.79, 159.3, 160.2. Elemental analysis for C$_9$H$_{13}$N$_2$O$_2$Br$_1$: Calcd. C, 41.40 H, 5.02N, 10.73 Br, 30.60 Found C, 41.59 H, 5.07N, 10.60 Br, 30.86

EXAMPLE 21 bis(1,1-dimethylethyl)4-nitro-4-[(6,7,8,9-tetrahydro-3-oxo-3H,5H-[1,2,4]oxadiazolo[4,3a]azepin-5-yl)methyl]heptanedioate

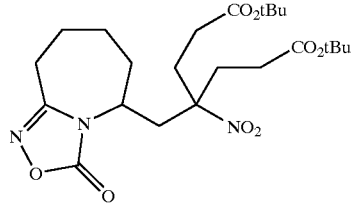

The product from example 16 (0.23 g, 1 mmole) was combined with t-butyl acrylate (0.26 g, 2 mmole) and $K_2CO_3$ in 5 mL of DMF. The reaction mixture was stirred for 18 hours. The reaction mixture was concentrated and the residue was partitioned between $CH_2Cl_2$ and water. The organic layer was dried over $MgSO_4$ then concentrated. The residue crystallized and was triturated with $Et_2O$ to yield 354 mg of the title material as a solid. Elemental analysis for $C_{23}H_{37}N_3O_8$. Calc: C: 57.13; H: 7.75; N: 8.69. Found: C: 57.24; H: 7.95; N: 8.53. Mass Spectral analysis for $C_{23}H_{37}N_3O_8$: $M^+NH_4=501$ $^1H$ NMR ($CDCl_3$) d 1.38–1.58 (m, 18H); 1.6–2.0 (m, 5H); 2.1–2.4 (m, 10H); 2.48–2.62 (m, 2H); 2.82–3.02 (m, 1H); 4.3–4.5 (m, 1H).

EXAMPLE 22

8,9-dihydro-5-[(phenylmethoxy)methyl]-3H,5H-[1,2,4]oxadiazolo[4,3-a]azepin-3-one

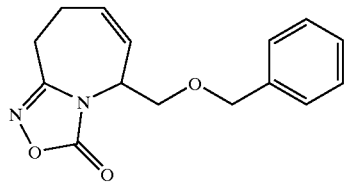

Ex-22a)

The Boc protected nitrile was synthesized according to the procedure published in J. Org. Chem. 56, 4196, 1991. $^1H$ NMR ($CDCl_3$) d 1.3–1.6 (m, 15H); 2.35–2.7 (m, 4H); 3.6–3.7 (dd, 1H); 3.95–4.1 (t, 1H); 4.5–4.7 (m, 1H); 5.4–5.6 (m, 2H).

Ex-22b)

The product of Example 22a (1.1 g, 3.9 mmol) was dissolved in 25 mL of EtOH saturated with HCl at 0° C. This mixture was allowed to warm to room temperature and stir for 18 hours. It was then concentrated in vavuo and the residue was triturated with ether to afford the ethyl imidate. $^1H$ NMR ($DMSOd_6$) d 1.3 (t, 3H); 2.3–2.9 (m, 4H); 3.4–3.6 (m, 2H); 3.38–3.98 (m, 1H); 4.36–4.48 (m, 2H); 5.4–5.66 (m, 2H).

Ex-22c)

Amberlyst A-27 (15.7 mL, 0.096 equivalents) was washed with water, 2N NaOH, water, then EtOH. The product of Example 22b was dissolved in EtOH and this solution was added to the Amberlyst A-27 resin. This mixture was agitated for 18 hours. The mixture was then filtered and the resin washed with EtOH. The filtrate was concentrated and the residue purified by C-18 chromatography (0% to 30% $CH_3CN/H_2O+0.05\%$ TFA, 25 min.). The amidine eluted just after the solvent front. Removal of solvent in vacuo afforded the 450 mg of the amidine as an oil. $^1H$ NMR ($MeODd_3$) d 2.3–2.6 (m, 3H); 2.7–2.8 (m, 1H); 3.15–3.25 (m, 1H); 3.55–3.8 (m, 2H); 5.4–5.6 (m, 1H); 5.75–5.9 (m, 1H). $^{13}C$ NMR ($MeODd_3$) d 24.6, 28.3, 53.2, 63.0, 126.7, 130.3, 171.3 Elemental analysis for $C_7H_{12}N_2O+1.1HCl+1.3MeOH$:

| Calc: C,44.92 | H,8.31 N, 12.62 | Cl,17.57 |
|---|---|---|
| Found: C,44.86 | H,7.84 N, 12.24 | Cl,17.84 |

Ex-22d)

The product of Example 22c is dissolved in pyridine and cooled to 0° C. The requisite amount of benzyl bromide is added and the mixture is stirred until the tlc indicates that the starting material is consumed. The reaction mixture is concentrated and the residue is partitioned between water and $CH_2Cl_2$. The organic phase is dried over $MgSO_4$ and concentrated to afford the benzyl ether.

Ex-22e)

The product of Example 22d is dissolved in EtOH containing hydroxylamine and potassium t-butoxide. This solution is refluxed until the starting material is consumed. The solvent is removed in vacuo. The residue is dissolved in water and made basic with $K_2CO_3$. The product is then extracted into $CH_2Cl_2$. The organic phase is dried over $MgSO_4$ and concentrated to afford the hydroxamidine.

Ex-22)

The product of Example 22e is combined with 1,1'-carbonyldiimidazolein $CH_2Cl_2$ and stirred until the thin layer chromatography (tlc) data indicates the starting material is consumed. The reaction mixture is washed with 10% $KHSO_4$ to remove excess imidazole. The organic solution is dried over $MgSO_4$ and concentrated in vacuo. The residue is chromatographed on silica gel to afford the title compound.

EXAMPLE 23

5-ethyl-6,7,8,9-tetrahydro-3H,5H-[1,2,4]oxadiazolo[4,3-a]azepine-3-thione

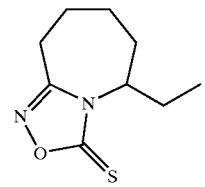

The product of Example 7b is allowed to react with 1,1'-thiocarbonyldiimidazole in $CH_2Cl_2$ for 24 hours at room temperature and the title compound is isolated from the reaction mixture using $C_{18}$ reverse phase HPLC as described in Example 2.

EXAMPLE 24

6-ethyl-7,8,9,10-tetrahydro-6H-[1,2,4]oxadiazino[4,3-a]azepine-3,4-dione

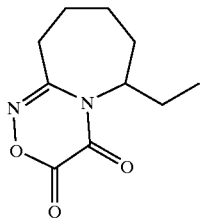

The product of Example 7b is allowed to react with oxalyl chloride in $CH_2Cl_2$ for 24 hours at room temperature and the title compound is isolated from the reaction mixture using $C_{18}$ reverse phase HPLC as described in Example 2.

EXAMPLE 25

5-[(4-amino-1H-imidazol-2-yl)methyl]-6,7,8,9-tetrahydro-3H,5H-[1,2,4]oxadiazolo[4,3-a]azepin-3-one,monohydrochloride

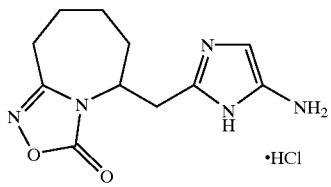

Ex-25a)

To a solution of the product of Example 8 in acetone is added Jones reagent until the red color persists as described in J. Chem. Soc. 1956, 39. The reaction is then quenched with isopropyl alcohol and concentrated under reduced pressure. The residue is then partitioned between brine and methylene chloride. The organic layer is back washed with a solution of sodium carbonate. The water layer is then acidified with concentrated hydrochloric acid and the precipitate is filtered and washed with water to afford the carboxylic acid.

Ex-25b)

To a solution of the product of Example 25a in methylene chloride is added a catalytic amount of DMF. Oxalyl chloride is added dropwise at room temperature and evolution of gas is observed. The reaction is followed by thin layer chromatography to determine when the reaction is complete. The completed reaction is concentrated under reduced pressure and the residue is dissolved in methylene chloride. The reaction mixture is cooled to 0° C. in an ice bath and ammonia is bubbled through it. The solvent is the removed under reduced pressure and the product is partitioned between brine and methylene chloride. The organic is dried over magnesium sulfate and solvent is removed under reduced pressure to afford the carboxamide.

Ex-25c)

To a solution of the product of Example 25b in methylene chloride is added triethylamine. The reaction is cooled to 0° C. in an ice bath and 12% phosgene in toluene is added dropwise. The reaction is stirred until completed as noted by thin layer chromatography. The reaction is washed with brine, dried over magnesium sulfate, and concentrated under reduced pressure. The crude residue is chromatographed to afford the nitrile.

Ex-25d)

To a solution of ethanol saturated with hydrogen chloride is added portion-wise the product of Example 25c. The reaction is allowed to warm to room temperature and is followed by thin layer chromatography. The completed reaction is concentrated and the residue is dissolved in ethanol to afford a solution of the ethyl acetimidate.

Ex-25)

The product of Example 25d is allowed to react with aminoacetonitrile to give the title material.

EXAMPLE 26

4,5,5a,6,7,8,9,9a-octahydro-5-methyl-1-oxo-1H-[1,2,4]oxadiazolo[4,3-a]quinoline-8-propanoic acid

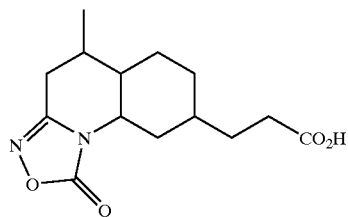

Ex-26a)

7-bromo-4-methyl-quinolin-2-ol is prepared from acetoacetic acid-(3-bromoanilde) and sulfuric acid by the method described in Monti et. al.; Gazz. Chim. Ital; 66; 1936; 723.

Ex-26b)

A solution of the product of Example 26a, Acrylic acid methyl ester, tetrabutyl ammonium chloride, $NaHCO_3$, and $Pd(OAc)_2$ in DMF is heated at 85° C. for 16 h. The solvent is removed and the product is purified by chromatography to afford the coupling product.

Ex-26c)

A mixture of the product of Example 26b and platinum oxide in glacial acetic acid is hydrogented at room temperature and 50 psi. The catalyst is filtered washed with acetic acid and concentrated. The desired lactam 26c is purified by column chromatography on silica gel.

Ex-26d)

A portion of the product of Example 26c is allowed to react with of trimethyloxonium tetrafluoroborate in $CH_2Cl_2$ over a 16 hour period. The mixture is diluted with $CH_2Cl_2$ and washed with 5% $NaHCO_3$ and brine. The organic phase is dried over $MgSO_4$, filtered and the solvent was evaporated in vacuo to afford the iminoether.

Ex-26e)

The product of Example 26d is allowed to react with hydroxylamine hydrochloride in MeOH for 16 hours. The methanol is evaporated to afford the hydroxamidine.

Ex-26f)

The product of Example 26e is allowed to react with 1,1'-carbonyldiimidazole in $CH_2Cl_2$ for 24 hours at room temperature. The methyl ester of the title compound is isolated from the reaction mixture using $C_{18}$ reverse phase HPLC.

Ex-26)

The product of Example 26f is hydrolyzed in 10% hydrochloric acid at reflux followed by concentration under reduced pressure. The resulting crude product residue is dissolved in water and extracted with diethyl ether. The product is purified on an ion exchange resin to produce the title material.

EXAMPLE 27

5,6,7,8-tetrahydro-5-(4-pentyl)-3H-[1,2,4]oxadiazolo[4,3-a]pyridin-3-one

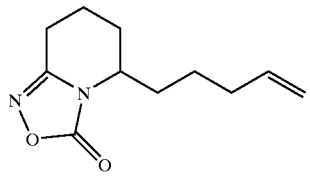

Ex-27a)

Methyl 2-oxocyclopentanecarboxylate (4.2 g, 30 mmol), 5-bromo-1-pentene (5.0 g, 33 mmol) and $K_2CO_3$, were combined in DMF (50 mL) and stirred for 18 hours. The reaction mixture was then poured onto ice and the product was extracted two times with $Et_2O$ then two times with hexane. The combined organic extracts were back washed with brine, dried over $MgSO_4$ and concentrated to yield approximately 4.0 g of the 1-pentenyl, 1-methoxycarbonylcyclopentanone as an oil. $^1H$ NMR (CDCl$_3$) d 1.3–1.6 (m, 3H); 1.75–2.0 (m, 6H); 2.1–2.4(m, 2H); 2.45–2.6 (m, 1H); 3.6–3.7 (m, 3H); 4.85–5.05 (m, 2H); 5.6–5.8 (m, 1H).

Ex-27b)

The product of Example 27a (0.42 g, 2 mmol) and LiCl (0.508 g, 12 mmol) were dissolved/suspended in 2.0 mL of DMF (DMF was not dried) and the mixture was placed in an oil bath heated to 153° C. The mixture was heated and stirred until gas evolution ceased. The reaction mixture was cooled and diluted with an equal volume of water. The product was extracted into 1:1 $Et_2O$:hexane. The organic extracts were back washed with brine, dried over $MgSO_4$ and concentrated to yield approximately 300 mg of the pentenylcyclopentanone as an oil. This material was chromatographed eluting with 3% EtOAc/hexane to yield an analytical sample. $^1H$ NMR (CDCl$_3$) d 1.2–1.35 (m, 1H); 1.36–1.6 (m, 3H); 1.65–1.8 (m, 2H); 1.9–2.15 (m, 5H); 2.18–2.45 (m, 2H); 4.9–5.02 (m, 2H); 5.7–5.85 (m, 1H).

Ex-27c)

The product of Example 27b (0.3 g, 2 mmol) was combined with hydroxylamine hydrochloride (0.277 g, 4 mmol) and sodium acetate (0.41 g, 5 mmol) in EtOH (20 mL) and water (10 mL). This mixture was refluxed until tlc (20% EtOAc/hexane) indicated that the starting material was consumed. The reaction mixture was concentrated to ⅓ of the original volume and the product was extracted into 1:1 $Et_2O$:hexane. The organic extracts were back washed with brine, dried over $MgSO_4$ and concentrated, to yield approximately 223 mg of an oil. The oil was chromatographed on silica eluting with EtOAc/hexane to yield 155 mg of the oxime as an oil. $^1H$ NMR (CDCl$_3$) d 1.28–1.5 (m, 3H); 1.54–1.9 (m, 4H); 1.65–1.8 (m, 2H); 1.95–2.1 (m, 2H); 2.26–2.64 (m, 2H); 4.88–5.02 (m, 2H); 5.7–5.86 (m, 1H); 8.75 (s, 1H). $^{13}C$ NMR (CDCl$_3$) d 22.2, 27, 27.5, 31.89, 31.92, 34.2, 42.5, 116, 138.5, 168.

Ex-27d)

TMSPPE was prepared by combining $P_2O_5$ (20 g, 146 mmol) and Hexamethyldisiloxane (49.6 mL, 234 mmol) in toluene (200 mL) and refluxed until the mixture was homogeneous. This mixture was cooled to room temperature and the product of Example 27c (9.5 g, 58 mmol) was added. This mixture was stirred and after 6 hours the mixture started to develop a red color which became deeper with time. A tlc in 100% $CH_3CN$ after 18 & 20 hours indicated a trace of starting material, but that the reaction had not changed. An equal volume of water was added and the mixture stirred for 2 hours. The phases were separated and the aqueous phase was washed with $CH_2Cl_2$.

The combined organic extracts were back washed with brine, dried over $MgSO_4$ and concentrated, to yield 9.2 g of a mixture of the regioisomers of the lactam as an oil. A 4.0 g sample of this oil was chromatographed (silica gel) eluting with 100% $CH_3CN$, to yield 1.4 g of the desired 7-isomer. $^1H$ NMR (CDCl$_3$) d 1.3–1.52 (m, 5H); 1.56–1.72 (m, 1H); 1.8–1.94 (m, 2H); 2.0–2.1 (q, 2H); 2.18–2.42 (m, 2H); 3.28–3.4 (m, 1H); 4.92–5.02 (m, 2H); 5.68–5.82 (m, 1H); 6.9 (s, 1H).

Ex-27)

The product of Example 27d (1.42 g; 8.5 mmol) was reacted by the methods described in Example 16 to yield 0.8 g of the title compound as an oil. Mass Spectra for $C_{11}H_{16}N_2O_2$: $M^+H=209$. $^1H$ NMR (CDCl$_3$) d 1.35–1.48 (m, 2H); 1.49–1.68 (m, 1H); 1.7–1.95 (m, 4H); 1.95–2.39 (m, 3H); 2.6–2.75 (m, 2H); 3.8–3.9 (m, 1H); 4.89–5.03 (m, 2H); 5.66–5.82 (m, 1H).

EXAMPLE 28

5,6,7,8-tetrahydro-3-oxo-3H-[1,2,4]oxadiazolo[4,3-a]pyridine-5-butanal

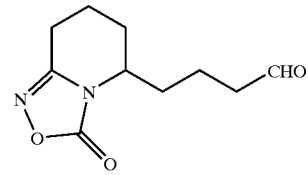

Ex-28)

The product of Example 27 (0.42 g; 2 mmol) and $NaIO_4$ (0.86 g; 4 mmol) were dissolved in a mixture of 12 mL of dioxane and 8 mL of $H_2O$. Two drops of a 2% solution of $OsO_4$ in n-butanol was added to the mixture. The reaction mixture was stirred until tlc (100% EtOAc) indicated that the starting material was consumed. A precipitate had formed and was filtered. This solid was washed with dioxane. The filtrate was concentrated and the residue was partitioned between $H_2O/CH_2Cl_2$. The organic layer was dried over $MgSO_4$ and concentrated to afford the title compound as an oil. $^1H$ NMR (CDCl$_3$) d 1.4–2.2 (m, 7H); 2.3–2.7 (m, 4H); 3.7–3.9 (m, 2H); 9.7 (s, 1H).

EXAMPLE 29

6,7-dihydro-5-pentyl-3H,5H-pyrrolo[2,1-c][1,2,4]thiadiazole-3-thione

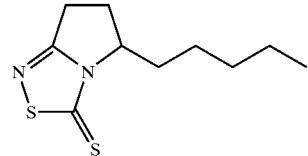

Ex-29a)

A suspension of ethyl acrylate, 1-nitrohexane, $K_2CO_3$, and Aliquat 336 (6 drops) is sonicated for 5 h. To the reaction is added $Et_2O$. The reaction mixture is filtered, extracted with brine, dried over $Na_2SO_4$ (anhydrous), filtered, and concentrated under reduced pressure to give a yellow liquid.

The product is purified by column chromatography to give methyl 4-nitrononanoate.

Ex-29b)

The product of Example 29a is reduced under catalytic hydrogenation conditions in methanol (60 psi, 55° C.) using Raney nickel. The reaction is heated for 8 h to effect cyclization after reduction of the nitro group. After concentrating the reaction mixture under reduced pressure, the residue is purified by column chromatography to give 5-n-pentylpyrrolidine-2-one.

Ex-29c)

This lactam product of Example 29b is treated with trimethyloxonium tetrafluoroborate as described in Example 2f to give the corresponding imino ether.

Ex-29d)

The imino ether product of Example 29c and hydroxylamine hydrochloride are refluxed in methanol under a nitrogen atmosphere for 3.5 h. After cooling the reaction to room temperature, it is filtered, stripped of all solvent under reduced pressure, and partitioned between water and EtOAc. The organic and aqueous phases are separated and the aqueous phase is washed with another portion of EtOAc before it is lyophilized to provide 5-n-pentyl-2-hydroximinopyrrolidine hydrochloride.

Ex-29)

The product of Example 29d is treated with carbondisulfide in an alcoholic KOH solution by the procedure of *Chem. Ber.* 22, 2441 (1889) to give the title material.

EXAMPLE 30

5,6,7,8-tetrahydro-5-propyl[1,2,3,5]oxathiadiazolo[3,4-a]pyridine 3,3-dioxide

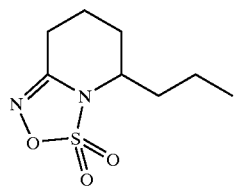

Ex-30a)

Cyclopentanone is treated with potassium-t-butoxide and then with allyl bromide in the same manner and in the same proportions as described for cyclohexanone in Example 6a, yielding 2-allylcyclopentanone.

Ex-30b)

A sample of the 2-allylcyclopentanone product of Example 30a is combined with $NH_2OH.HCl$ and sodium acetate in a mixture of ethanol and water. This mixture is refluxed for 5 h under a nitrogen atmosphere and stirred at room temperature for an additional 5 days. All solvent is removed under reduced pressure. The residue is partitioned between ethyl acetate and water and the organic phase is washed with 1×75 mL of saturated NaCl (brine), dried over $Na_2SO_4$, and stripped of all solvent under reduced pressure, giving the corresponding oxime.

Ex-30c)

A sample of the oxime product of Example 30b is added to a dropping funnel containing 80% $H_2SO_4$. After using a stirring rod to obtain a turbid solution, this mixture is added dropwise (10 min) to 80% $H_2SO_4$ stirred magnetically and maintained at 120° C. with an external oil bath. An exotherm may be noted and the temperature of the reaction may rise to 160° C. before cooling again to 120° C. Ten minutes later the flask is removed from the bath and allowed to cool to room temperature. The product mixture is diluted with water and brought to pH 6 with concentrated $NH_4OH$. This solution is further diluted with of water and extracted with 3 portions of $CH_2Cl_2$. The combined organic phase is washed with 1×50 mL of brine, dried ($Na_2SO_4$), filtered, and stripped of all solvent under reduced pressure to give the lactam. Silica column chromatography is used to separate the 3-allyl piperidine-2-one from the desired 6-allyl piperidine-2-one.

Ex-30d)

The 6-allyl-piperidine-2-one product of Example 30c is reduced with palladium on carbon in methanol under hydrogen to give the 6-n-propyl-piperidine-2-one.

Ex-30e)

The 6-n-propyl-piperidine-2-one product of Example 30d is treated with trimethyloxonium tetrafluoroborate as described in Example 2f to give the corresponding imino ether.

Ex-30f)

The imino ether product of Example 30e is treated with of hydroxylamine hydrochloride as described in Example 2g to give the corresponding hydroxyamidine.

Ex-30g)

The hydroxyamidine product of Example 30f is allowed to react with 1,1'-sulfonyldiimidazole in $CH_2Cl_2$ for 24 hours at room temperature. The title compound is isolated from the reaction mixture using $C_{18}$ reversed phase HPLC (water-acetonitrile gradient).

EXAMPLE 31

6,7-dihydro-5-pentyl-3H-pyrrolo[1,2-a]imidazole-2,3(5H)-dione

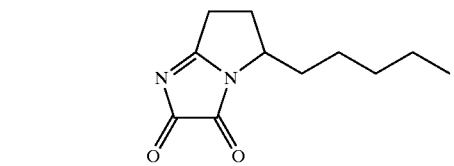

Ex-31a)

A suspension of ethyl acrylate, 1-nitrohexane, $K_2CO_3$, and Aliquat 336 (6 drops) is sonicated for 5 h. To the reaction is added $Et_2O$. The reaction mixture is filtered, extracted with brine, dried over $Na_2SO_4$ (anhydrous), filtered, and concentrated under reduced pressure to give a yellow liquid. The product is purified by column chromatography to give methyl 4-nitrononanoate.

Ex-31b)

The product of Example 31a is reduced under catalytic hydrogenation conditions in methanol (60 psi, 55 C.) using Raney nickel. The reaction is heated for 8 h to effect cyclization after reduction of the nitro group. After concentration of the reaction mixture under reduced pressure, the residue is purified by column chromatography to give 5-n-pentyl-pyrrolidine-2-one.

Ex-31c)

This lactam product of Example 31b is treated with trimethyloxonium tetrafluoroborate as described in Example 2f to give the corresponding imino ether.

Ex-31d) The imino ether product of Example 31c and ammonium chloride ($NH_4Cl$) are refluxed in methanol under a nitrogen atmosphere for 3.5 h. After cooling the reaction to room temperature, it is filtered, stripped of all solvent under reduced pressure, and partitioned between water and EtOAc. The organic and aqueous phases are separated and the aqueous phase is washed with another portion of EtOAc before it is lyophilized to provide 5-n-pentyl-2-iminopyrrolidine hydrochloride.

Ex-31)

The product of Example 31d is treated with oxalyl chloride and diazabicyclooctane in acetonitrile to give the title compound, which is purified by partition between water and EtOAc, and passage over a silica column.

EXAMPLE 32

5,6,7,8-tetrahydro-7-methyl-5-propyl-2H-[1,2,4]oxadiazolo[2,3-a]pyridin-2-one

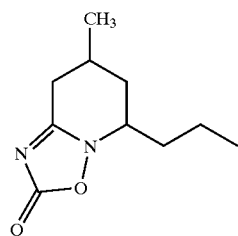

Ex-32a)

Methyl Propionate is deprotonated with lithium diisopropylamide in THF at −30° C. and treated with 1-bromo-2-oxopentane. The product methyl 2-methyl-4-oxohepatoate is isolated by partition of the reaction mixture between water and methylene chloride.

Ex-32b)

The product methyl ester of Example 32a is hydrolyzed with lithium hydroxide in methanol to provide the free acid.

Ex-32c)

The resulting free acid of Example 32b is reduced to the corresponding alcohol by careful addition of borane in THF, giving 2-methyl-4-oxo-1-heptanol.

Ex-32d)

Treatment of the product alcohol of Example 32c with methanesulfonyl chloride in pyridine gives the corresponding mesylate.

Ex-32e)

The mesylate product of Example 32d is treated with potassium cyanide in DMSO to give 3-methyl-5-oxo-ocanenitrile.

Ex-32f)

The 3-methyl-5-oxo-ocanenitrile product of Example 32e is reduced to the corresponding alcohol with aluminum isopropoxide in isopropanol.

Ex-32g)

This 6-methyl-7-cyano-4-heptanol product of Example 32f is treated with carbon tetrabromide and triphenylphosphine to give 3-methyl-5-bromo-ocanenitrile.

Ex-32h)

The 3-methyl-5-bromo-ocanenitrile product of Example 32g is reacted with hydroxylamine hydrochloride to give 1-hydroxy-4-methyl-6-n-propyl-2-iminopiperidine.

Ex-32)

The product of Example 32h is condensed with carbonyldiimidazole to give the title compound.

EXAMPLE 33

7,8-dihyro-7-methyl-6-(2-propenyl)-3H-pyrrolo[1,2-b][1,2,4]oxadiazine-2,3(6H)-dione

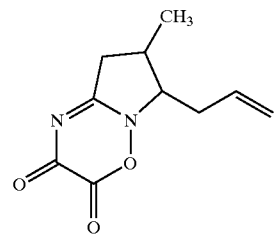

Ex-33a)

Diethylketone is deprotonated with lithium diisopropylamide in THF at −30° C. and treated with bromoacetonitrile. The product is isolated by partition of the reaction mixture between water and methylene chloride. The organic layer is dried and stripped of all solvent to yield the 3-methyl, 4-oxovaleronitrile product.

Ex-33b)

The product methyl ester of Example 33a is reduced to the corresponding alcohol with aluminum isopropoxide in isopropanol.

Ex-33c)

The product of Example 33b is treated with carbon tetrabromiide and triphenyiphosphine to give 3-methyl, 4-bromovaleronitrile Ex-33d)

The product of Example 33c is reacted with hydroxylamine hydrochloride to give 1-hydroxy-4-methyl-5-ethyl-2-iminopyrrolidine.

Ex-33)

The product of Example 33d is allowed to react with oxalyl chloride in pyridine to give the title material.

EXAMPLE 34

Methyl 5,6,7,8-tetrahydro-6,8-dimethyl-3-oxo-7-(trifluoromethyl)-3H-[1,2,4]oxadiazolo[4,3-a]pyridine-5-acetate

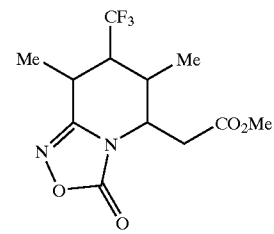

EXAMPLE 35

5-(3-butenyl)-6,7,8,9-tetrahydro-5H-[1,2,3,5]oxathiadiazolo[3,4-a]azepine3-oxide

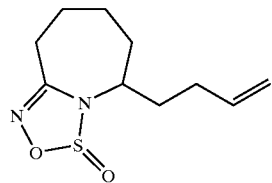

Ex-35a)
The reactions with cyclohexanone described in Examples 6a–6d are repeated with the replacement of allyl bromide by 3-butenyl-1-bromide to generate the hydroxyamidine hydrochloride.

Ex-35)
The hydroxyamidine hydrochloride product of Example 35a is treated at 0° C. with thionyl chloride in acetonitrile in the presence of triethylamine. The reaction mixture is poured on ice and extracted with three portions of methylene chloride. The organic fractions are combined, dried, flitered, stripped, and purified by silica chromatography to give the title compound.

EXAMPLE 36

6,7-dihydro-5-pentyl-3H,5H-pyrrolo[2,1-c][1,2,4]thiadiazol-3-one

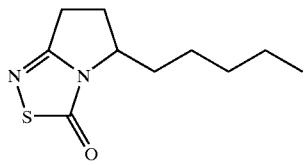

Ex-36a)
As depicted in Scheme 10, 2-Trimethylsilylethanol is treated with tosyl chloride in pyridine to give 2-trimethylsilyl-1-tosylethane.

Ex-36b)
The product of Example 36a is treated with sodium hydrosulfide to give 2-trimethylsilylethanethiol.

Ex-36c)
The 2-trimethylsilylethanethiol hydrochloride product of Example 35a is treated with chloramine to give 1-thia-3-trimethylsilyl-n-propylamine hydrochloride.

Ex-36d)
The imino ether product from Example 31 is treated with 2-thia-3-trimethylsilyl-n-propylamine hydrochloride in refluxing methanol to give compound 36d.

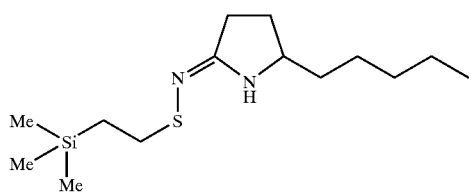

36d

Ex-36)
The product of Example 36d is treated under anhydrous conditions with anhydrous tetrabutylammonium flouride, followed by carbonyldiimidazole, to give the title compound.

EXAMPLE 37

5-(ethoxymethyl)-6,7,8,9-tetrahydro-3H,5H-[1,2,4]oxadiazolo[4,3-a]azepin-3-one

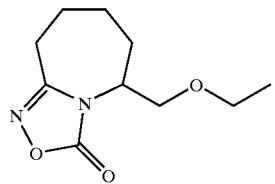

Ex-37a)
A sample of the product of Example 5 (1.3 g, 7.2 mmol) and carbontetrabromide (3.0 g, 8.9 mmol) in $CH_2Cl_2$ (70 mL) was cooled to 0° C. To this stirred mixture was added triphenylphosphine (2.8 g, 10.7 mmol) portion-wise. The reaction was allowed to warm to room temperature and stirr for 18 h. After the reaction was concentrated, the residue was dissolved in a minimum of 20% acetonitrile/toluene and chromatographed on silica eluting with the dissolving solvent mixture to produce 1.5 g (86%) of the bromomethyl intermediate.

Ex-37)
To the product of Example 37a or the product of Example 15 in ethanol is added an ethanolic solution of sodium ethoxide. After thin layer chromatography indicates the reaction is complete, it is concentrated and the residue partitioned between water and an extraction solvent. The dried organic layer is stripped of all solvent and the residue chromatographed to produce the title material.

EXAMPLE 38

5-[(ethylthio)methyl]-6,7,8,9-tetrahydro-3H,5H-[1,2,4]oxadiazolo[4,3-a]azepin-3-one

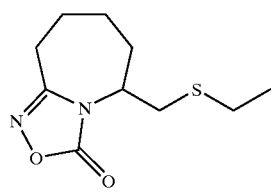

The product of Example 37a or the product of Example 15 is reacted with sodium thioethoxide by the methods of Example 37 to generate the title material.

EXAMPLE 39

5-[(ethylsulfinyl)methyl]-6,7,8,9-tetrahydro-3H,5H-[1,2,4]oxadiazolo[4,3-a]azepin-3-one

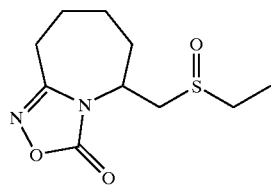

The product of Example 38 is reacted with one equivalent of MCPBA in $CH_2Cl_2$ to generate the title material.

EXAMPLE 40

5-[(ethylsulfonyl)methyl]-6,7,8,9-tetrahydro-3H,5H-[1,2,4]oxadiazolo[4,3-a]azepin-3-one

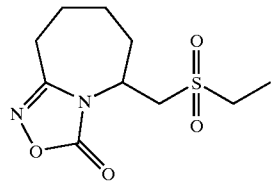

To the product of Example 38 in MeOH is added excess 30% $H_2O_2$ and the solution warmed sufficiently to generate the title material.

EXAMPLE 41

6,7,8,9-tetrahydro-5-(1-oxo-3-butenyl)-3H,5H-[1,2,4]oxadiazolo[4,3-a]azepin-3-one

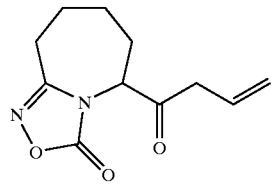

Ex-41a)

A sample of the product of Example 4 (0.5 g, 2.0 mmol) dissolved in 5 mL of THF was treated with 2.5 mL of water that 0.23 g (85% pellets, 4.1 mmol) of potassium hydroxide had dissolved in. After stirring this reaction for 45 min, it was poured into a mixture of EtOAc(50 mL) and 1M $KHSO_4$. The organic layer was separated, dried, and concentrated to produce the crude carboxylic acid intermediate product. This material can be used crude or purified by chromatography.

Ex-41b)

To a sample of the product of Example 41a dissolved in DMF is added O,N-dimethylhydroxylamine hydrochloride, 1(3-dimethylaminopropyl)-3-ethyl carbodiimide hydrochloride, 1-hydroxybenzotriazole hydrate, and triethyl amine. The reaction mixture is stirred overnight at room temperature to yield the methoxymethyl amide after purification.

Ex-41)

A solution of the product of Example 41b in THF is cooled and subsequently treated with a THF solution of allylmagnesium bromide. The reaction is warmed to room temperature and worked up. The title material is isolated by chromatography.

EXAMPLE 42

N-[2-(6,7,8,9-tetrahydro-3-oxo-3H,5H-[1,2,4]oxadiazolo[4,3-a]azepin-5-yl]ethyl]methanesulfonamide

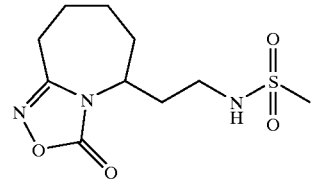

The product of Example 3 dissolved in an organic solvent is reacted with excess triethyl amine followed by excess methyl sulfonyl chloride to yield the title material following work up and chromatography.

EXAMPLE 43

5-(2-aminomethyl)-6,7,8,9-tetrahydro-3H,5H-[1,2,4]oxadiazolo-[4,3-a]azepin-3-one

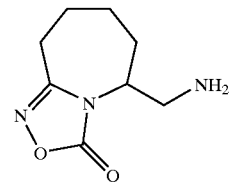

Ex-43a)

The product of Example 15 (1.55 g, 6.27 mmol) was dissolved in 15 mL of dimethylformamide (DMF), and then sodium azide (2.04 g, 31 mmol) was added to this solution. The resulting mixture was stirred under nitrogen at 50° C. overnight, at which time HPLC analysis indicated that the bromomethyl starting material had disappeared. The DMF was removed under reduced pressure. The residue was dissolved in ethyl acetate and water. The EtOAc layer was washed with water, 0.1 N HCl, water and brine, dried over $Na_2SO_4$, filtered and evaporated to give 1.26 g (96%) of the desired azide product as a yellow oil (95% pure by HPLC analysis). $^1$H NMR (CDCl$_3$) d 4.53 (m, 1H), 3.61 (m, 2H), 2.96 (m, 1H), 2.57 (m, 1H), 2.18 (m, 1H), 2.07 (m, 1H), 1.95 (m, 1H), 1.76 (m, 2H), 1.55 (m, 1H) MS $C_8H_{11}N_5O_2$ m/z=210.2 [M+H]$^+$.

The azide product from Ex-43a (180 mg, 0.86 mmol) was dissolved in 10 mL of THF and 0.4% water, then polymer-bound PPh$_3$ (320 mg, 0.94 mmol; loaded with 3 mmol PPh$_3$/g) was added. The resulting mixture was stirred under nitrogen at room temperature overnight, at which time mass spectral analysis indicated that the azide starting material had disappeared and a new signal corresponding to the desired amine product had formed. The polymer was removed by filtration and was washed with methanol. The filtrate was evaporated to give 100 mg of the desired 5-(2-aminomethyl)-6,7,8,9-tetrahydro-3H,5H-[1,2,4]oxadiazolo-[4,3-a]azepin-3-one product as an off-white solid. $^1$H NMR (CDCl$_3$) d 4.24 (m, 1H), 3.29 (m, 2H), 2.86 (m, 1H), 2.10 (m, 2H), 1.88 (m, 2H), 1.77 (m, 2H), 1.48 (m, 1H). HRMS calcd. for $C_8H_{13}N_3O_2$: 184.1086 [M+H]$^+$; found 184.1067.

EXAMPLE 44

N-[2-(6,7,8,9-tetrahydro-3-oxo-3H,5H-[1,2,4]
oxadiazolo-[4,3-a]azepin-5-yl)methyl]
methanesulfonamide

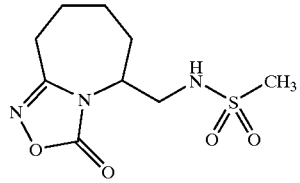

The product of Example 43 dissolved in an organic solvent is reacted with excess triethylamine followed by excess methyl sulfonyl chloride to yield the title material following work up and chromatography.

Additional Examples 45–51 can be prepared by one skilled in the art using similar methods, as shown in Example 44.

EXAMPLES 45–51

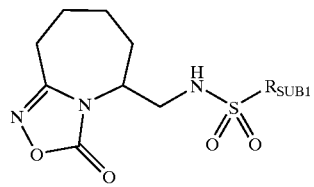

| Ex. No. | $R_{SUB1}$ |
|---|---|
| 45 | phenyl |
| 46 | 4-MeO$_2$C—C$_6$H$_4$— |
| 47 | 3-MeO$_2$C—C$_6$H$_4$— |
| 48 | 2-MeO$_2$C—C$_6$H$_4$— |
| 49 | 2-MeO$_2$C-3-thienyl- |
| 50 | 5-MeO$_2$C-2-furyl- |
| 51 | MeO$_2$C—CH$_2$CH$_2$— |

EXAMPLE 52

N-Methyl-N-[2-(6,7,8,9-tetrahydro-3-oxo-3H,5H-[1,2,4]-oxadiazolo-[4,3-a]azepin-5-yl]methyl]
methanesulfonamide

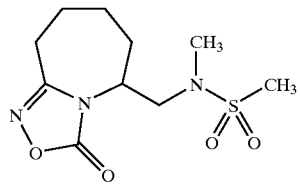

The product of Examples 44 dissolved in an organic solvent is reacted with excess diazomethane in diethyl ether at 0–5° C. overnight to yield the title material following work up and chromatography.

Additional Examples 53–59 can be prepared by one skilled in the art using similar methods.

EXAMPLES 53–59

N-Methyl-N-[2-(6,7,8,9-tetrahydro-3-oxo-3H,5H-[1,2,4]oxadiazolo[4,3-a]azepin-5-methyl]sulfonamides.

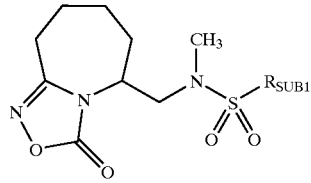

| Ex. No. | $R_{SUB1}$ |
|---|---|
| 53 | phenyl |
| 54 | 4-MeO$_2$C—C$_6$H$_4$— |
| 55 | 3-MeO$_2$C—C$_6$H$_4$— |
| 56 | 2-MeO$_2$C—C$_6$H$_4$— |
| 57 | 2-MeO$_2$C-3-thienyl- |
| 58 | 5-MeO$_2$C-2-furyl- |
| 59 | MeO$_2$C—CH$_2$CH$_2$— |

EXAMPLE 60

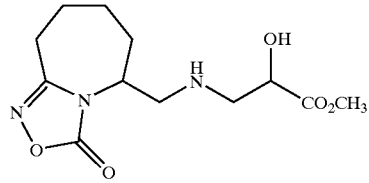

The product of Example 43 dissolved in an organic solvent is reacted with excess methyl glycidate to yield the indicated material following work up and chromatography.

EXAMPLE 61

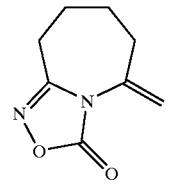

The product of Example 15 (247 mg, 1 mmol) was dissolved in 5 mL of DMF. Potassium carbonate (138 mg, 1 mmol) and methyl amine (0.5 mL, 2 M in THF) were added, and the resulting mixture was stirred under nitrogen at room temperature overnight, at which time HPLC analysis indicated that the bromomethyl starting material disappeared. The DMF was removed under reduced pressure. The residue was partitioned between methylene chloride and water, the aqueous layer was extracted with methylene chloride. The combined organic layers were concentrated, and the resultant crude product was purified by reverse phase HPLC to give 30 mg (18%) of the desired olefinic product as an off-white oil. $^1$H NMR (CDCl$_3$) d 5.34 (dd, 2H), 2.70 (m, 2H), 2.40 (m, 2H), 1.84 (m, 2H). $^{13}$C NMR (CDCl$_3$) d 159.17 (CO), 157.61 (CO), 138.47(C═), 114.46(C═), 35.39 (CH$_2$), 29.72 (CH$_2$), 26.27 (CH$_2$), 24.85 (CH$_2$). $^{13}$C NMR DEPT (CDCl$_3$) 35.39 (CH$_2$), 29.72 (CH$_2$), 26.27 (CH$_2$), 24.85 (CH$_2$). MS C$_8$H$_{10}$N$_2$O$_2$ m/Z=167.2 [M+H]$^+$.

EXAMPLE 62

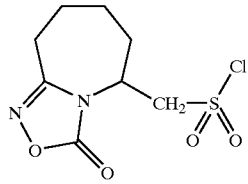

Ex-62a)

To a DMF (15 mL) solution of the bromide product from Example 15 (1.50 g, 6.1 mmol) was added potassium thioacetate (1.32 g, 11.6 mmol). The resulting cloudy brown solution was stirred at room temperature for 18 hours. The reaction mixture was poured into brine and the organic layer was separated. The organic layer was washed with water and brine, dried (MgSO$_4$) and evaporated to give 1.48 g (100%) of the desired thioacetate product as a tan solid. LCMS: m/z=265.0 [M+Na]. $^1$H NMR (CDCl$_3$) d 1.47 (m, 1H), 1.7–2.0 (m, 3H), 2.13 (m, 1H), 2.32 (s, 3H), 2.74 (m, 1H), 2.97 (m, 1H), 3.03 (dd, 1H), 3.42 (dd, 1H), 4.33 (m, 1H).

The thioacetate product from Ex-62a (1.48 g, 6.1 mmol) was dissolved in 10% EtOH in CHCl$_3$ (50 mL) and cooled in an ice/water bath. Chlorine gas was bubbled through the stirred solution until a yellow color persisted (approximately 5 minutes). The resulting slurry was stirred for 90 minutes in an ice bath. The solvent was removed under vacuum to give 1.58 g (96%) of the desired sulfonyl chloride product as a white solid. LCMS: m/z=267.0 [M+H]$^+$. $^1$H NMR (10% d$_6$DMSO in CDCl$_3$) d 1.21 (q, 1H), 1.5–1.7 (m, 3H), 1.85 (m, 1H), 2.02 (m, 1H), 2.33 (m, 1H), 2.65 (dd, 1H), 2.96 (m, 2H), 4.53 (m, 1H).

EXAMPLE 63

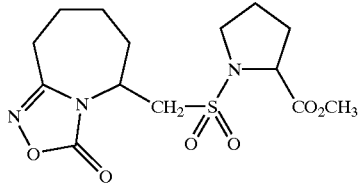

The product of Example 62 dissolved in an organic solvent is reacted with excess triethylamine followed by excess proline methyl ester hydrochloride to yield the indicated proline sulfonamide following work up and chromatography.

Additional Examples 64–77 can be prepared by one skilled in the art using similar methods.

EXAMPLES 64–77

[2-(6,7,8,9-tetrahydro-3-oxo-3H,5H-[1,2,4] oxadiazolo[4,3-a]azepin-5-yl]methyl]sulfonamides.

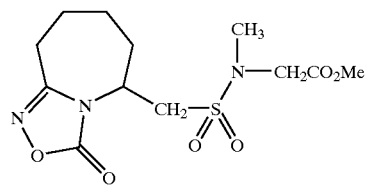

| Ex. No. | R$_{SUB1}$ |
|---|---|
| 64 | MeO$_2$C—CH$_2$CH$_2$— |
| 65 | 3-MeO$_2$C—C$_6$H$_4$— |
| 66 | 2-MeO$_2$C—C$_6$H$_4$— |
| 67 | 2-MeO$_2$C-3-thienyl- |
| 68 | MeO$_2$C—CH(CH$_3$)— |
| 69 | MeO$_2$C—CH(CH$_2$OH)— |
| 70 | MeO$_2$C—CH$_2$CH(CH$_3$)— |
| 71 | MeO$_2$C—CH(CH$_3$)CH$_2$— |
| 72 | MeO$_2$C—CH$_2$— |
| 73 | (EtO)$_2$PO—CH$_2$CH$_2$— |
| 74 | (EtO)$_2$PO—CH$_2$— |
| 75 | MeO$_2$C—CH(OH)CH$_2$— |
| 76 | H |
| 77 | MeOSO$_2$—CH$_2$CH$_2$— |

EXAMPLE 78

The product of Examples 72 dissolved in an organic solvent is reacted with excess diazomethane in diethyl ether at 0–5° C. overnight to yield the indicated N-methylsulfonamide material following work up and chromatography.

Additional Examples 79–90 can be prepared by one skilled in the art using similar methods.

EXAMPLES 79–90

N-Methyl-[2-(6,7,8,9-tetrahydro-3-oxo-3H,5H-[1,2,4]oxadiazolo[4,3-a]azepin-5-yl]methyl]sulfonamides.

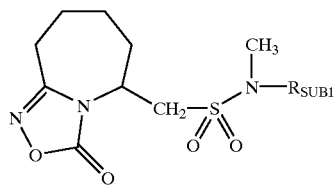

| Ex. No. | $R_{SUB1}$ |
|---|---|
| 79 | $MeO_2C-CH_2CH_2-$ |
| 80 | $3\text{-}MeO_2C-C_6H_4-$ |
| 81 | $2\text{-}MeO_2C-C_6H_4-$ |
| 82 | $2\text{-}MeO_2C\text{-}3\text{-thienyl-}$ |
| 83 | $MeO_2C-CH(CH_3)-$ |
| 84 | $MeO_2C-CH(CH_2OH)-$ |
| 85 | $MeO_2C-CH_2CH(CH_3)-$ |
| 86 | $MeO_2C-CH(CH_3)CH_2-$ |
| 87 | $MeOSO_2-CH_2CH_2-$ |
| 88 | $(EtO)_2PO-CH_2CH_2-$ |
| 89 | $(EtO)_2PO-CH_2-$ |
| 90 | $MeO_2C-CH(OH)CH_2-$ |

EXAMPLE 91

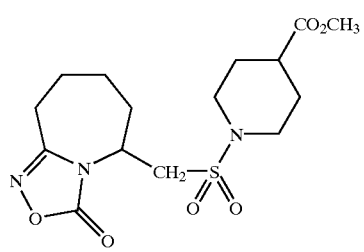

The product of Example 62 dissolved in an organic solvent is reacted with excess triethylamine followed by excess methyl isonipecotate to yield the indicated piperidine sulfonamide following work up and chromatography.

EXAMPLE 92

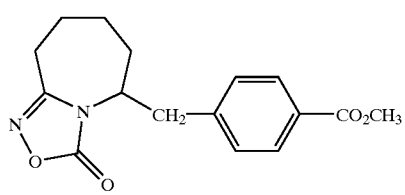

The product of Example 15 dissolved in an organic solvent is reacted with excess aqueous sodium carbonate followed by excess 4-methoxycarbonyl phenylboronic acid and a catalytic amount of tetrakistriphenylphosphine palladium to yield the indicated p-substituted benzoate ester following work up and chromatography.

EXAMPLE 93

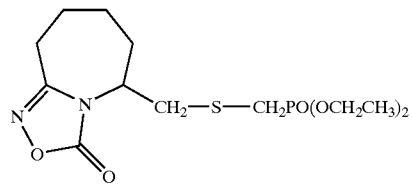

The product of Example 15 dissolved in an organic solvent is reacted with excess triethylamine followed by excess diethyl mercaptomethyl phosphonate to yield the indicated phosphonomethyl thioether product following work up and chromatography.

EXAMPLE 94

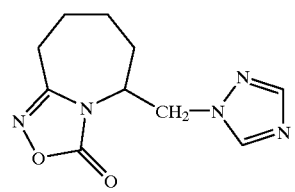

The product of Example 15 dissolved in an organic solvent is reacted with excess triethylamine followed by excess 1,2,4-triazole to yield the indicated N-substituted triazole product following work up and chromatography.

EXAMPLE 95

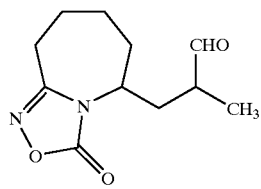

EXAMPLE 96

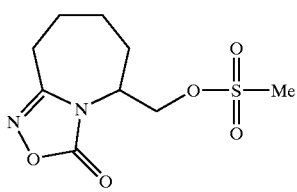

A sample of the product of Example (5) (4.2 g, 22.5 mmol) dissolved in a mixture of 27 mL of pyridine and 50 mL of $CH_2Cl_2$ was cooled to 0° C. To this was added dropwise 1.9 mL (25.1 mmol) of methane sulfonyl chloride. The reaction was allowed to slowly warm to room temperature and stirr over night before all solvent was removed under reduced pressure. Toluene (10 mL) was added to the residue and again all solvent was removed under reduced pressure. The residue was diluted with a mixture of EtOAc (200 mL) and 1M $KHSO_4$ (50 mL). The organic layer was separated, washed with brine, dried ($MgSO_4$), and concentrated to produce 4.1 g of the title product. This material can be used crude or purified by chromatography.

Elemental analysis for $C_9H_{14}N_2O_5Cl$:

| Calcd: C,41.21 | H,5.98 | N,10.68. |
|---|---|---|
| Found: C,41.29 | H,5.93 | N,10.45. |

EXAMPLE 97

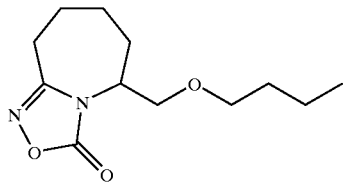

Argon was bubbled through a solution of n-butanol (0.07 g, 0.76 mmol) dissolved in 10 mL of THF. To this stirred solution was added a 60% dispersion of sodium hydride (33.6 mg, 0.84 mmol). After gas evolution had ceased, a sample of the product of Example (96) (0.2 g, 0.76 mmol) dissolved in 5 mL of THF was added to the stirred reaction mixture. The reaction was allowed to stirr for 6 hours before it was poured into a mixture of EtOAc and 1M $KHSO_4$. The organic layer was separated, dried, and concentrated to produce 120 mg of crude title product. This material was purified by chromatography to yield 70 mg of the title product.

EXAMPLE 98

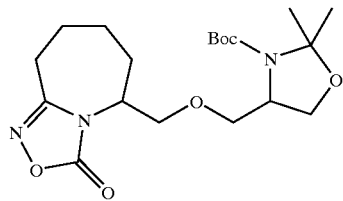

Argon was bubbled through a solution of Garner's alcohol (0.88 g, 3.81 mmol) dissolved in 40 mL of THF. To this stirred solution was added a 60% dispersion of sodium hydride. After gas evolution had ceased, a sample of the product of Example (96) (1.0 g, 3.81 mmol) dissolved in 5 mL of THF was added to the stirred reaction mixture. The reaction was allowed to reflux for 2 hours before it was cooled to room temperature and worked up as described by Example (97). This material was purified by chromatography to yield 830 mg of the title product.

EXAMPLE 99

6,7,8,9-tetrahydro-3-oxo-3H,5H-[1,2,4]oxadiazolo[4,3-a]azepine-5-carboxylic acid

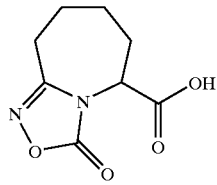

Potassium hydroxide (0.47 g, 8.39 mmol) was dissolved in 10 mL of 50% aqueous THF. To this was added a solution of the product of Example 4 in 6 mL THF and the reaction mixture was stirred for 2 h at 25° C. Diethylether (20 mL) was then added and the reaction mixture was made acidic by adding 10 mL of 1N HCl. The organic layer was separated, dried over magnesium sulfate, filtered and all solvent evaporated to give 0.43 g (52% yield) of the title product. The structure of the compound was characterized by $^1H$ and $^{13}C$ NMR.

EXAMPLE 100

6,7,8,9-tetrahydro-3-oxo-3H,5H-[1,2,4]oxadiazolo[4,3-a]azepine-5-carboxylic acid chloride

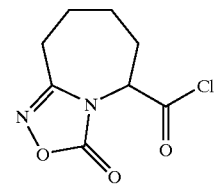

To a solution of the 5 g of the product of Example (99) in 50 mL $CH_2Cl_2$ was added thionyl chloride (50 mL) and the reaction mixture was stirred for 6 h at 20° C. The solvent was evaporated under reduced pressure to give 5.1 g of the white title product residue which was characterized by $^1H$ NMR.

EXAMPLE 101

6,7,8,9-tetrahydro-3-oxo-3H,5H-[1,2,4]oxadiazolo[4,3-a]azepine-5-methoxymethycarboxylic acid amide

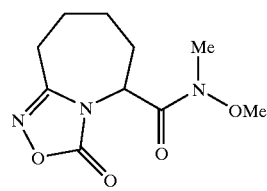

To a solution of the product of Example (99) (5 g, 21.01 mmol) in methylene chloride (45 mL) was added carbonyl diimidazole (CDI, 3.71 g, 23.11 mmol) and the reaction mixture was stirred for 10 min. Methoxymethyl amine (2.25 g, 23.11 mmol) was then added to the above reaction mixture and stirring was continued for 16 h at 25° C. A 1N potassium hydrogen sulfate solution (50 mL) was then added before this solution was extracted with 200 mL of toluene. The organic layer was washed with saturated aq. sodium bicarbonate and then brine, dried over magnesium sulfate, filtered and evaporated to give 4.59 g (91% yield) of the title product.

EXAMPLE 102

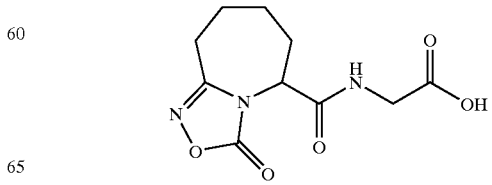

EXAMPLE 103

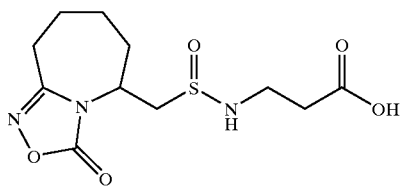

EXAMPLE 104

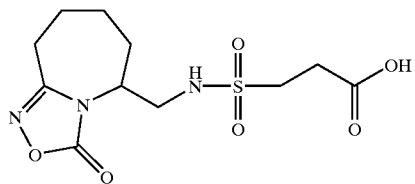

EXAMPLE 105

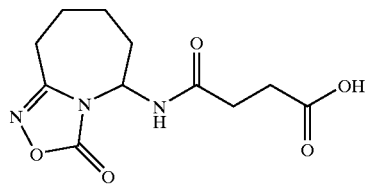

EXAMPLE 106

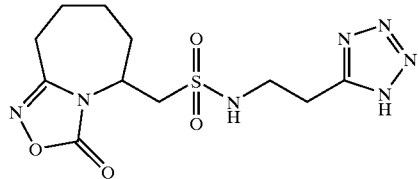

EXAMPLE 107

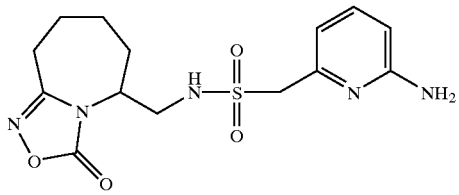

EXAMPLE 108

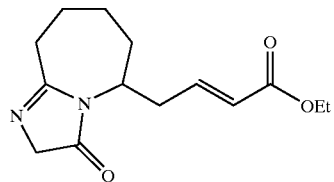

EXAMPLE 109

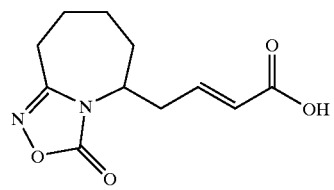

EXAMPLE 110

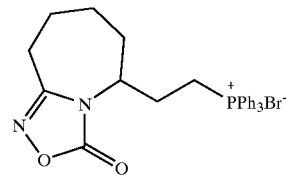

Ex-110

To a solution of EX-20 (5.71 g, 0.026 mol) in toluene (25 mL) was added triphenylphosphine (7.17 g, 0.027 mol). The reaction was heated at reflux in an oil bath for 16 hours. After cooling, the toluene was decanted from the glassy solid. The solid was triturated with diethyl ether overnight to afford the title product (10.21 g, 0.020 mol) in 90% yield. $^1$H NMR (CDCl$_3$, 300 MHz) d 1.50–2.9(m, 11H), d 3.58 (m, 1H), d 4.16(m, 1H), d 4.41(m, 1H) d 7.6–8.0(m, 15H). $^{13}$C NMR (CDCl$_3$, 75 MHz) d 24.43, 24.97, 25.50, 55.08, 55.27, 116.9, 118.1, 130.4, 130.6, 133.5, 135.1, 135.2, 159.4, 160. $^{31}$P NMR (CDCl$_3$, 300 MHz) d 26.0.

EXAMPLE 111

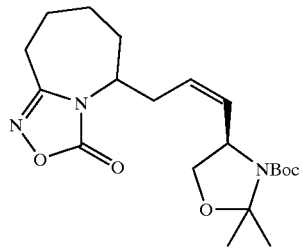

Ex-111

To a 50 mL 3-neck round bottom flask fitted with an addition funnel was added
Ex-110
(5.0 g, 0.010 mol) in THF(20 mL). The solution was cooled to −78° C. in a dry ice bath. To the solution was added potassium bis(trimethylsilyl)amide (0.5M)(21 mL, 0.021 mol) slowly so that the temperature would not raise above −72° C. The reaction stirred at −78° C. for 15 minutes.

The dry-ice bath was placed so that the reaction stirred at −45° C. for 1.5 hours. To the reaction was added Garner's Aldehyde (1.97 g, 0.009 mol) drop wise so that the temperature did not raise above −72° C. The reaction stirred for an additional 45 minutes then the dry ice bath was removed and stirred at room temperature for 4 hours. To the reaction was added a saturated solution of ammonium chloride. The organics were collected and washed with brine(3×25 mL), dried over magnesium sulfate anhydrous, removed under reduced pressure. The product was purified utilizing flash chromatography with 30:70 ethyl acetate:hexane to afford the title (1.85 g, 0.005) compound in 54.7% yield. $^1$H NMR (CDCl$_3$, 300 MHz) d 1.21(s, 9H), d 1.25–3.0 (m, 15H), d 3.65(dd, 1H), d 4.11(m, 1H), d 5.40(m, 4H). Mass Spec m/z 394.5(M+H), m/z 432.4(M+K), m/z 294.4(M+H-100).

EXAMPLE 112

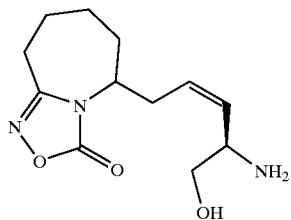

Ex-112

To a 2N hydrochloric acid dissolved in methanol (20 mL) solution was added Ex-111

(1.13 g, 0.003 mol). The reaction stirred for 3 hours. The solvent was removed in vacuo to afford the title product in quantitative yield. Mass Spec: 254.1(M+H).

EXAMPLE 113

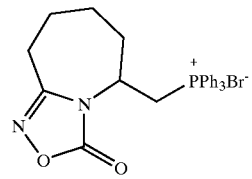

Ex-113

To a flask was added Ex-15 (1 g, 0.004 mol) and triphenylphosphine (1.08 g, 4.1 mol). The mixture was placed into an oil bath which held a constant temperature of 110° C. for 16 hours. When the reaction cooled, the glassy solid was triturated with diethyl ether for 10 hours. The title product was isolated as a fine white powder (0.93 g, 0.002 mol) in 50% yield. $^{31}$P NMR (CDCl$_3$, 300 MHz) d 22(s). Chemical Analysis: $C_{26}H_{26}N_2O_2BrP$

|  | carbon | hydrogen | nitrogen | bromine |
|---|---|---|---|---|
| calculated | 61.31 | 5.14 | 5.50 | 15.69 |
| found | 58.64 | 5.19 | 5.64 | 17.46 |

EXAMPLE 114

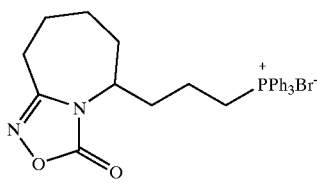

Ex-114

The procedure to make EX-110 was followed to afford the title product in 98% yield. $^1$H NMR (CDCl$_3$, 300 MHz) d1.38–2.61(m, 9H), d 2.85 (dd, 1H), d 3.60(m, 1H), d 3.19(m, 1H), d 4.45(m, 1H), d 7.60–7.9(m, 15H).

EXAMPLE 115

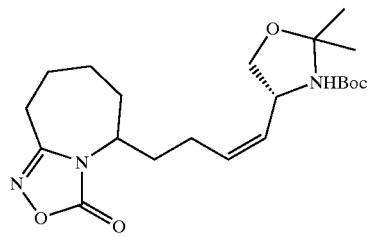

Ex-115

To a 50 mL 3-neck round bottom flask fitted with an addition funnel was added Ex-114

(5.0 g, 0.010 mol) in THF (20 mL). The solution was cooled to −78° C. in a dry ice bath. To the solution was added potassium bis(trimethylsilyl)amide (0.5M)(21 mL, 0.02 mol) slowly so that the temperature would not raise above −72° C. The reaction stirred at −78° C. for 15 minutes. The dry-ice bath was placed so that the reaction stirred at −45° C. for 1.5 hours. To the reaction was added Garner's Aldehyde (1.97 g, 0.009 mol) drop wise so that the temperature did not raise above −72° C. The reaction stirred for an additional 45 minutes then the dry ice bath was removed and stirred at room temperature for 4 hours. To the reaction was added a saturated solution of ammonium chloride. The organics were collected and washed with brine(3×25 mL), dried over magnesium sulfate anhydrous, removed under reduced pressure. The product was purified utilizing flash chromatography with 30:70 ethyl acetate:hexane to afford the title(1.85 g, 0.005) compound in 40% yield. $^1$H NMR (CDCl$_3$, 300 MHz) d 1.21(s, 9H), d 1.25–3.0 (m,17H), d 3.65(dd, 1H), d 4.11(m, 2H), d 4.2(t, 1H), d 4.6(d, 1H), d 5.40(m, 2H). Mass Spec m/z 408.2(M+H). EXAMPLE 116

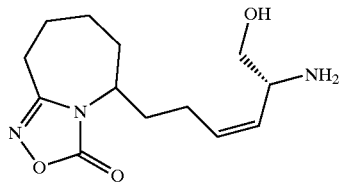

Ex-116

To a 2N hydrochloric acid dissolved in methanol(20 mL) solution was added Ex-115

(1.13 g, 0.003 mol). The reaction stirred for 3 hours. The solvent was removed in vacuo to afford the title product in quantitative yield. $^1$H NMR (D$_2$O, 300 MHz) d 1.21(t, 1H), d 1.45(q, 1H), d 1.6–2.3 (m,9H), d 2.50 (t,1H), d 3.35(dd, 1H), d 3.49(m, 1H), d 3.7(m, 2H), d 4.21(t, 1H), d 5.40(m, 2H). Mass Spec m/z 268.1(M+H).

EXAMPLE 117

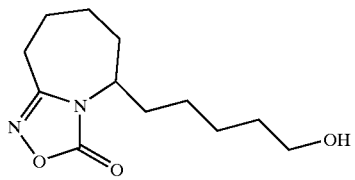

Ex-117

A solution of BH$_3$ (1M)(26 mL) in THF was cooled to 0° C. in an ice bath. To this solution was added a solution Ex-27 (5.0 g, 0.025 mol) in dry THF (25 mL) drop wise via an addition funnel. The reaction stirred at 0° C. for 2.5 hours. To the reaction was added a 3% hydrogen peroxide at a pH of 10, adjusted 1N sodium hydroxide. After 3 hours, ethyl acetate(50 mL) was added and was partitioned between brine(50 mL). The organics were collected and dried over magnesium sulfate anhydrous then removed under reduced pressure. The pale yellow oil was purified by flash chromatography using 1:1 ethyl acetate:hexane to afford the title product (2.42 g) in 30% yield. $^1$H NMR (CDCl$_3$, 300 MHz) d1.4–2.2(m, 15H), d 2.51 (t, 1H), d 2.89(dd, 1H), d 3.61(q, 2H), d 4.25(m, 1H).

EXAMPLE 118

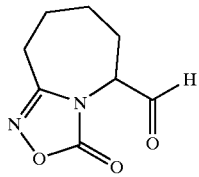

Ex-118

A solution of 8 mL (16 mmol) 2 M oxalylchloride in CH$_2$Cl$_2$ was diluted with 15 mL CH$_2$Cl$_2$. It was cooled to −60° C. and 5 mL (70 mmol) DMSO was added very slowly. After 5 minutes stirring 2.1 g (11.4 mmol) alcohol in 50 mL CH$_2$Cl$_2$ was added and the mixture was stirred for 30 minutes at −60° C. To this mixture was added 10 mL (72 mmol) TEA and stirring continued for 16 hours. The mixture was diluted with 200 mL CH$_2$Cl$_2$ and washed with 2×100 mL sat. KHSO$_4$ and brine. The organic phase was dried over MgSO$_4$ and the solvent was evaporated in vacuo, yielding 2 g (96%) of the title product as oil. FAB MS: MH$^+$=183.0

EXAMPLE 119

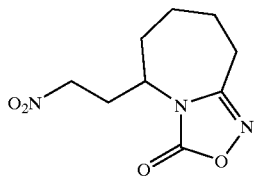

Ex-119A

The nitro-lactam (5.5 g; 0.03 mole) was combined with trimethyloxonium tetrafluoroborate (5.0 g; 0.033 mole) and dissolved/suspended in 50 ml of CH$_2$Cl$_2$. The mixture was stirred for 18 hours, where the mixture was homogenous. Saturated NaHCO$_3$ (50 ml) was added and the mixture stirred until gas evolution ceased and the pH was at least 8. The layers were separated and the organic phase was dried over MgSO$_4$ and concentrated in vacuo, yielding 5.8 g of an oil.

Ex-119B

The above oil was combined with hydroxylamine hydrochloride (4.2 g; 0.028 mole) and ethanol (50 ml) then refluxed for one hour. The mixture was cooled and concentrated in vacuo. The residue was partitioned between saturated NaHCO$_3$/CH$_2$Cl$_2$. The organic layer was dried over MgSO$_4$ and concentrated in vacuo, yielding an oil.

Ex-119

This oil was combined with 1,1'-carbonyldiimidazole (4.5 g; 0.028 mole) and dissolved in 50 ml of CH$_2$Cl$_2$, and stirred 18 hours. The reaction mixture was washed with 10% KHSO$_4$ to remove excess imidazole. The organic solution was dried over MgSO$_4$ and concentrated in vacuo. The residue was chromatographed on Merck silica, eluting with 40% EtOAc/hexane. The desired product eluted first off the column and crystallized upon concentration, to yield 3.1 g of a white powder. C$_9$H$_{13}$N$_3$O$_4$, MW 227.218. Mass Spec: M+H@ 228 $^1$H NMR (CDCl$_3$) * 1.4 to 1.6, m (1H); 1.75 to 1.86, m (2H); 1.95 to 2.19, m (3H); 2.28 to 2.39, m (1H); 2.48 to 2.62, m (2H); 2.91 to 2.98 & 2.98 to 3.01, d of d of t (1H); 4.28 to 4.38, m (1H); 4.38 to 4.54, m (2H).

EXAMPLE 120 EXAMPLE 121

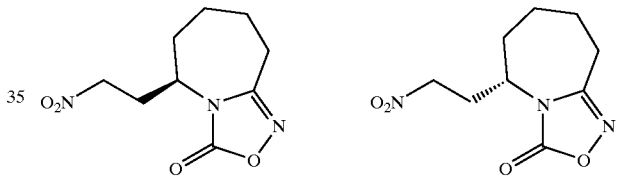

Ex-120/121

The product of EX-119 (1.0 g) was separated into the two enantiomers on a reverse phase chiral column. The first component was EX-120 (459 mg) and the second component was EX-121 (429 mg).

EXAMPLE 122

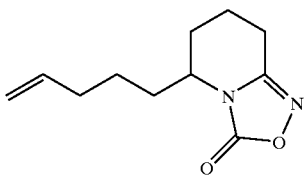

Ex-122a

Methyl 2-oxocyclopentanecarboxylate (4.2 g; 0.03 mole), 5-bromo-1-pentene (5.0 g; 0.033 mole) and K$_2$CO$_3$, were combined in DMF (50 ml) and stirred 18 hours. The reaction mixture was poured on to ice and the product was extracted two times with Et$_2$O then two times with hexane. The combined organic extracts were back washed with brine, dried over MgSO$_4$ and concentrated, to yield approximately 4.0 g of an oil. $^1$H NMR (CDCl$_3$) * 1.3 to 1.6, m (3H); 1.75 to 2.05, m (6H); 2.1 to 2.4, m (2H); 2.45 to 2.6, m (1H); 3.6 to 3.7, m (3H); 4.85 to 5.05, m (2H); 5.6 to 5.8, m (1H).

Ex-122b

The crude product (420 mg; 0.002 mole) and LiCl (508 mg; 0.012 mole) were dissolved/suspended in 2.0 ml of DMF (DMF was not dried) and the mixture was placed in an oil bath heated to 153° C. The mixture was heated and stirred until gas evolution ceased. The reaction mixture was cooled and diluted with an equal volume of water. The product was extracted into 1:1 Et$_2$O:hexane. The organic extracts were back washed with brine, dried over MgSO$_4$ and concentrated, to yield approximately 300 mg of an oil. Tlc 20% EtOAc/hexane indicated that the starting material was consumed.

Ex-122c

Chromatography of 247 g eluting with 3% EtOAc/hexane yielded 102 g of the desired product. $^1$H NMR (CDCl$_3$) * 1.2 to 1.35, m (1H); 1.36 to 1.6, m 3H); 1.65 to 1.8, m (2H); 1.9 to 2.15, m (5H); 2.18 to 2.45, m (2H); 4.9 to 5.02, m (2H); 5.7 to 5.85, m (1H).

Ex-122d

The olefinic ketone (300 mg; 0.002 mole) was combined with hydroxylamine hydrochloride (277 mg; 0.004 mole) and sodium acetate (410 mg; 0.005 mole) in EtOH (20 ml) and water (10 ml). This was refluxed until tlc 20% EtOAc/hexane indicated that the starting material was consumed. The reaction mixture was concentrated to ⅓ of the original volume and the product was extracted into 1:1 Et$_2$O:hexane. The organic extracts were back washed with brine, dried over MgSO$_4$ and concentrated, to yield approximately 223 mg of an oil. The oil was chromatographed on silica, eluting with EtOAc/hexane, yielding 155 mg of an oil. $^1$H NMR (CDCl$_3$) * 1.28 to 1.5, m (3H); 1.54 to 1.9, m (4H); 1.65 to 1.8, m (2H); 1.95 to 2.1, m (2H); 2.26 to 2.64, m (2H); 4.88 to 5.02, m (2H); 5.7 to 5.86, m (1H); 8.75, s (1H). $^{13}$C NMR (CDCl$_3$) * 22.2, 27, 27.5, 31.89, 31.92, 34.2, 42.5, 116, 138.5, 168.

Ex-122E

TMSPPE was prepared by combining P$_2$O$_5$ (20 g, 0.146 mole) and Hexamethyldisiloxane (49.6 ml, 0.234 mole) in toluene (200 ml) and refluxed until the mixture was homogeneous. This mixture was cooled to room temperature and the oxime (9.5 g, 0.058 mole) was added. This mixture was stirred, and after 6 hours the mixture started to develop a red color, which became deeper with time. Tlc 100% CH$_3$CN after 18 & 20 hours indicated a trace of starting material, but that the reaction had not changed. An equal volume of water was added and the mixture stirred for 2 hours. The phases were separated and the aqueous phase was washed with CH$_2$Cl$_2$. The combined organic extracts were back washed with brine, dried over MgSO$_4$ and concentrated, to yield 9.2 g of an oil containing both regio isomers. 4.0 g of the oil was chromatographed, eluting with 100% CH$_3$CN, to yield 1.4 g of the desired regio isomer. $^1$H NMR (CDCl$_3$) * 1.3 to 1.52, m (5H); 1.56 to 1.72, m (1H); 1.8 to 1.94, m (2H); 2.0 to 2.1, q (2H); 2.18 to 2.42, m (2H); 3.28 to 3.4, m (1H); 4.92 to 5.02, m (2H); 5.68 to 5.82 m (1H); 6.9, s (1H).

Ex-122

The olefinlactam (1.42 g; 0.0085 mole) was carried on as described in Example 119 to yield 770 mg of an oil. C$_{11}$H$_{16}$N$_2$O$_2$, MW 208.25. Mass Spec: M+H@ 208.9 $^1$H NMR (CDCl$_3$) * 1.35 to 1.48, m (2H); 1.49 to 1.68, m (1H); 1.7 to 1.95, m (4H); 1.95 to 2.39, m (3H); 2.6 to 2.75, m (2H); 3.8 to 3.9, m (1H); 4.89 to 5.03, m (2H); 5.66 to 5.82, m (1H).

EXAMPLE 123 EXAMPLE 124

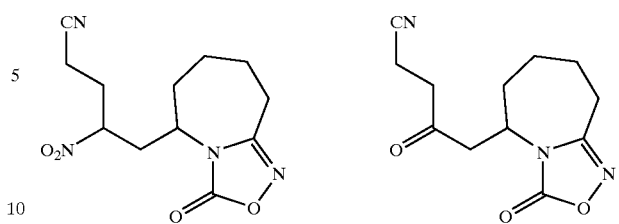

Ex-123/124

The product from Example 119 (227 mg; 0.001 mole) was combined with acrylonitrile (106 mg; 0.002 moles) and potassium carbonate (149 mg; 0.001 moles) in DMF (5.0 ml). The reaction mixture was stirred under nitrogen for 48 hr. The starting material was consumed. The reaction mixture was concentrated and the residue was partitioned between H$_2$O/CH$_2$Cl$_2$. The organic layer was dried over MgSO$_4$ then concentrated. The residue was chromatographed by prep tlc. Eluted with 40% EtOAc/hexane. Two products were collected:

The less polar component (30 mg) was EX-123. C$_{12}$H$_{15}$N$_3$O$_3$, MW 280.28. Mass Spec: M+H@ 281. Elemental Analysis: Calc: C, 51.42; H, 5.75; N, 19.99; Found: C, 51.16; H, 5.72; N, 19.87.

The more polar component (107 mg) was EX-124. C$_{12}$H$_{15}$N$_3$O$_3$, MW 249.27. Mass Spec: M+H@ 250. $^1$H NMR (CDCl$_3$) * 1.1 to 2.95, m (11H); 3.5, s (2H); 4.2 to 4.8, m (2H).

EXAMPLE 125

(2S,3Z)-2-amino-5-(6,7,8,9-tetrahydro-3-oxo-3H, 5H-[1,2,4]oxadiazolo[4,3-a]azepin-5-yl)-3-pentenoic acid

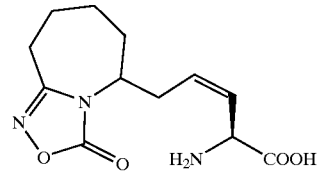

Ex-125a)

A suspension of potassium t-butoxide (200 g, 1.78 mol) in toluene which was cooled to 0° C. in an ice bath under N$_2$ was treated with cyclohexanone (157 g, 1.60 mol). To the reaction mixture was slowly added allyl bromide (194 g, 1.60 mol) over a 2 hour period. The reaction warmed to room temperature over 5 hours. The reaction was then poured onto ethyl acetate (400 mL) and washed once with 10% potassium hydrogen sulfate (250 mL). The organic solution was then washed with brine (3×200 mL), dried over magnesium sulfate, and evaporated under reduced pressure. The resulting oil was then chromatographed to yield the allyl cyclohexanone as an oil, 158.4 g (71.6%). $^1$H NMR (CDCl$_3$, 300 MHz) d 1.2–2.5(m, 10H), 2.59 (m, 1H), 5.0(dd, 2H), 5.75(m, 1H). $^{13}$C NMR (CDCl$_3$, 75 MHz) d 25.04, 28.03, 33.46, 33.86, 42.12, 50.35, 116.3, 136.6, 212.5.

Ex-125b)

A solution of the product of Ex-125a (56.4 g, 0.408 mol) in formic acid (200 mL) stirred under N$_2$ for 5 minutes. To this solution was added hydroxylamine-O-sulfonic acid (97%, 53.0 g, 0.448 mol). The reaction was refluxed for 45 minutes then the solvent was removed under reduced pressure. Ethyl acetate was poured onto the resulting black slurry and neutralized with a solution of saturated sodium bicarbonate until the evolution of gas ceased. The organic was separated, washed with brine (3×150 mL), dried over magnesium sulfate anhydrous and removed under reduced pressure. The resulting dark brown solid was chromatographed with 1:1 ethyl acetate:hexane to afford the caprolactam as a cream colored solid, 18.5 g (30%). $^1$H NMR (CDCl$_3$, 300 MHz) d1.25(m, 2H), 1.42(m, 2H), 1.86(m, 2H), 2.15(m, 2H), 2.33(m, 2H), 3.28(m, 2H), 5.04(dd, 2H), 5.64(m, 1H) 6.07(bs, 1H). $^{13}$C NMR (CDCl$_3$, 75 MHz) d 23.30, 29.87, 35.51, 37.14, 40.66, 53.05, 118.9, 134.1, 177.9.

Ex-125c)

A solution of the product of Ex-125b (10 g, 0.068 mol) in methylene chloride (200 mL) stirred under a blanket of N$_2$ for 5 minutes. To the solution was added Meerwein's reagent (13.09 g, 0.089 mol) in two portions which had been ground into a powder. The reaction was stirred for 16 hours while being monitored by thin layer chromatograph. The reaction was neutralized by a solution of saturated sodium bicarbonate until the evolution of gas ceased and the pH was 10. The organic was separated, washed with brine (3×100 mL), dried over magnesium sulfate anhydrous, then removed under reduced pressure. The imino ether was isolated as an oil (~10 g) and carried to the next reaction with no further purification.

Ex-125d)

To a solution of the product of Ex-125c (~10) in methanol (100 mL) under N$_2$ was added hydroxylamine hydrochloride (5.92 g, 0.085 mol). The reaction refluxed for 2 hours then was cooled to room temperature. The solvent was removed under reduced pressure then methylene chloride (100 mL) and water (100 mL) was added to the resulting oil. To the well stirred bilayer was added K$_2$CO$_3$ until the pH of the water was 10.5. The organics were then separated, washed with brine (3×100 mL), dried over magnesium sulfate anhydrous and removed in vacuo. The hydroxamidine was isolated as a cream colored solid (~11 g) and was carried on without further purification.

Ex-125e)

To a round bottom flask was added the product of Ex-125d (~11 g) in methylene chloride (150 mL) under N$_2$. To a separate round bottom flask was added 1,1'-carbonyldiimidazole (CDI) (12.15 g, 0.079 mol) in methylene chloride. Both flasks were cooled to 0° C. in an ice bath. To the flask containing the CDI was added the solution of the product of example 1d via a canula. After the last of the addition, the reaction stirred in the ice bath as it warmed to room temperature overnight. To the reaction was added a solution of 10% potassium hydrogensulfate (200 mL). The organic was separated, washed with brine (3×100 mL), dried over magnesium sulfate anhydrous, then removed under reduced pressure. The resulting solid was chromatographed with 1:1 ethyl acetate:hexane to afford the oxadiazolinone, 8.02 g (60.6%). $^1$H NMR (CDCl$_3$, 300 MHz) d1.50–2.25(m, 6H), 2.51 (m, 4H), 2.87 (dd, 2H), 4.29(m, 1H), 5.05(dd, 2H), 5.75(m, 1H). $^{13}$C NMR (CDCl$_3$, 75 MHz) d 23.97, 25.66, 26.32, 31.22, 36.52, 53.45, 119.1, 133.0, 159.7, 160.7.

Ex-125f)

A solution of the product of Ex-125e (3.0 g, 0.015 mol) in methylene chloride and methanol(75/45 mL) was cooled to −78° C. in a dry ice bath. The reaction stirred as ozone was bubble through the solution at a 3 ml/min flow rate. When the solution stayed a consistent deep blue, the ozone was remove and the reaction was purged with nitrogen. To the cold solution was added sodium borohydride(2.14 g, 0.061 mol) very slowly to minimize the evolution of gas at one time. To the reaction was added glacial acetic acid slowly to bring the pH to 3. The reaction was then neutralized with saturated sodium bicarbonate. The oraganics were then washed 3×50 mL with brine, dried over magnesium sulfate anhydrous, removed under reduced pressure. The pale oil was run through a plug of silica (15 g) to afford the hydoxyethyl product, 5.15 g, 0.026 mol (64%). $^1$H NMR (CDCl$_3$, 300 MHz) d 1.18–2.15 (m, 8H), 3.59 (m, 2H), 4.39 (m, 1H). $^{13}$C NMR (CDCl$_3$, 75 MHz) d 24.45, 25.71, 26.47, 32.56, 34.67, 51.16, 58.85, 160.66, 160.89.

Ex-125g)

In a solution of the product of Ex-125f (5.15 g, 0.026 mol) in methylene chloride(100 mL) at 0° C. in an ice bath was added carbon tetrabromide (10.78 g, 0.033 mol). The solution was cooled to 0° C. in an ice bath. Then triphenylphosphine (10.23 g, 0.39 mol) was added portion-wise as not to allow the temperature raise above 3° C. The reaction was stirred for 2 hours and the solvent was removed in vacuo. The crude was purified by flash chromatography to yield the bromoethyl product, 5.9 g, 0.023 mol (87%). $^1$H NMR (CDCl$_3$, 300 MHz) d 1.50–2.60(m, 9H), 2.99 (dd, 1H), 3.35(m, 2H), 4.41(m, 1H). $^{13}$C NMR (CDCl$_3$, 75 MHz) d 23.89, 25.33, 26.04, 28.06, 31.59, 35.05, 52.79, 159.3, 160.2. Elemental analysis for C$_{10}$H$_{16}$N$_2$O$_3$:

|  | carbon | hydrogen | nitrogen | bromine |
|---|---|---|---|---|
| calculated | 41.40 | 5.02 | 10.73 | 30.60 |
| found | 41.59 | 5.07 | 10.60 | 30.86 |

Ex-125h)

To a solution of the product of Ex-125g (5.71 g, 0.026 mol) in toluene (25 mL) was added triphenylphosphine (7.17 g,0.027 mol). The reaction was stirred at reflux in an oil bath for 16 hours. After cooling, the toluene was decanted from the glassy solid. The solid was tritrated with diethyl ether overnight to afford the phosphonium bromide (10.21 g, 0.020 mol) in 90% yeild. $^1$H NMR (CDCl$_3$, 300 MHz) d 1.50–2.9(m, 11H), d 3.58 (m, 1H), d 4.16(m, 1H), d 4.41(m, 1H) d 7.6–8.0(m, 15H). $^{13}$C NMR (CDCl$_3$, 75 MHz) d 24.43, 24.97, 25.50, 55.08, 55.27, 116.9, 118.1, 130.4, 130.6, 133.5, 135.1, 135.2, 159.4, 160. $^{31}$p NMR (CDCl$_3$, 300 MHz) d 26.0.

Ex-125i)

To a 50 mL 3-neck round bottom flask fitted with an addition funnel was added the product of Ex-125i (5.0 g, 0.010 mol) in 20 mL of THF. The solution was cooled to −78° C. in a dry ice bath. To the solution was added potassium bis(trimethylsilyl)amide (0.5M)(21 mL, 0.021 mol) slowly so that the temperature would not raise above −72° C. The reaction stirred at −78° C. for 15 minutes. To the reaction was added Garner's Aldehyde (1.97 g, 0.009 mol) drop wise so that the temperature did not raise above −72° C. The reaction stirred for an additional 45 minutes then the dry ice bath was removed and stirred at room temperature for 4 hours. To the reaction was added a saturated solution of ammonium chloride. The organics were collected and washed with brine(3×25 mL), dried over magnesium sulfate anhydrous, removed under reduced pressure. The product was purified utilizing flash chromatography with 30:70 ethyl acetate:hexane to afford the protected amino alcohol (1.85 g, 0.005) in 54.7% yield. $^1$H NMR (CDCl$_3$, 300 MHz) d 1.21(s, 9H), d 1.25–3.0 (m, 15H), d 3.65(dd, 1H), d 4.11(m, 1H), d 5.40(m, 4H). Mass Spec m/z 394.5(M+H), m/z 432.4(M+K), m/z 294.4(M+H-100).

Ex-125j)

To a solution of the product of Ex-125i (1.13 g, 0.003 mol) in methylene chloride(20 mL) was added triflouroacetic acid(4 mL). The reaction stirred for two hours then a solution of 5% potassium carbonate was added. The organics were collected and washed with brine(3×20 mL), dried over magnesium sulfate anhydrous, removed under reduced pressure. To the resulting residue was added acetone(20 mL). To this solution was added Jone's Reagent(8N, 20 drops). After 2 hours, the reaction was monitored by TLC and starting material remained. Twenty additional drops were pipetted in and the reaction stirred over night. To the reaction was added methanol(10 mL). To the slurry was added water (100 mL) and the reaction was purified by reverse phase chromatography to afford the title product. $^1$H NMR ($D_2O$, 300 MHz) d 1.0–2.5 (m, 7H), d 3.5(d, 1H), d 4.6(d, 1H), d 5.35(t, 1H), d 5.75(m, 1H). Mass Spec: 226.3(M+H).

EXAMPLE 126 a-amino-4,5,5a,6,7,8,9,9a-octahydro-5-methyl-1-oxo-1H-[1,2,4]oxadiazolo[4,3-a]quinoline-8-propanoic acid

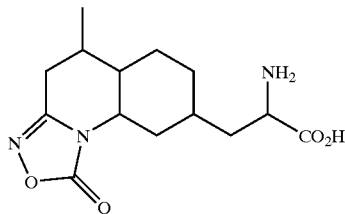

Ex-126a)

7-bromo-4-methyl-quinolin-2-ol is prepared from acetoacetic acid-(3-bromoanilde) and sulfuric acid by the method described in Monti et. al.; *Gazz. Chim. Ital;* 66; 1936; 723.

Ex-126b)

N-Butoxycarbonyldehydroalanine methyl ester is prepared by the method of Gladisli et. al.; *Tetrahedron Asymmetry;* 2; 7; 1991; 623–632. A solution of the product of Ex.-126a, N-butoxycarbonyldehydroalanine methyl ester, tetrabutyl ammonium chloride, $NaHCO_3$, and $Pd(OAc)_2$ in DMF is heated at 85° C. for 16 h. The solvent is removed and the product is purified by chromatography to afford the coupling product.

Ex-126c)

A mixture of the product of Ex.-126b and platinum oxide in glacial acetic acid is hydrogented at room temperature and 50 psi. The catalyst is filtered washed with acetic acid and concentrated. The desired lactam 126c is purified by column chromatography on silica gel.

Ex-126d)

A portion of the product of Ex.-126c is allowed to react with of trimethyloxonium tetrafluoroborate in $CH_2Cl_2$ over a 16 hour period. The mixture is diluted with $CH_2Cl_2$ and washed with 5% $NaHCO_3$ and brine. The organic phase is dried over $MgSO_4$, filtered and the solvent was evaporated in vacuo to afford the iminoether.

Ex-126e)

The product of Ex-126d is allowed to react with hydroxylamine hydrochloride in MeOH for 16 hours. The methanol is evaporated to afford the hydroxamidine.

Ex-126f)

The product of Ex-126e is allowed to react with 1,1'-carbonyldiimidazole in $CH_2Cl_2$ for 24 hours at room temperature. The title compound is isolated from the reaction mixture using $C_{18}$ reverse phase HPLC.

Ex-126g)

The product of Ex-126f is hydrolyzed in 10% hydrochloric acid at reflux followed by concentration under reduced pressure. The resulting crude product residue is dissolved in water and extracted with diethyl ether. The product is purified on an ion exchange resin to produce the title material.

EXAMPLE 127

N-[(1,1-dimethylethoxy)carbonyl]-3-[[2-(6,7,8,9-tetrahydro-3-oxo-3H,5H-[1,2,4]oxadiazolo[4,3-a]azepin-5-yl)ethyl]amino]-L-alanine

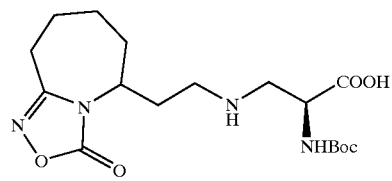

Ex-127a)

A solution of 2 g (10 mmol) of the product of Ex-125f was allowed to react with 2.04 g (10 mmol) N-a-Boc-L-diaminopropionic acid in 30 mL DMF (containing 0.3 mL acetic acid) with stirring for 1 hour. To this solution was added 1.25 g (20 mmol) $NaCNBH_3$ and stirring was continued for 18 hours. The DMF was evaporated in vacuo and the residue was dissolved in 200 mL ethyl acetate. The organic solution was washed with 2×100 mL 10%$KHSO_4$ and brine. The organic phase was dried over $MgSO_4$, filtered and the solvent was evaporated in vacuo, yielding 1.7 g (44%) of the title product as a slightly yellow oil. Mass spectral analysis for $C_{17}H_{28}N_4O_6$: M+H=385.

EXAMPLE 128

N-[(1,1-dimethylethoxy)carbonyl]-3-[ethyl[2-(6,7,8,9-tetrahydro-3-oxo-3H,5H-[1,2,4]oxadiazolo[4,3-a]azepin-5-yl)ethyl]amino]-L-alanine

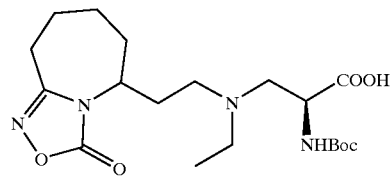

Ex-128)

A solution of 1.7 g (4.4 mmol) of the product of Ex-127 was dissolved in 30 mL DMF (containing 0.3 mL acetic acid) and 0.22 mL (5 mmol) acetaldehyde. This was stirred vigorously for 30 minutes. To this mixture was then added 0.625 g (10 mmol) $NaCNBH_3$ and stirring was continued for 18 hours. The DMF was evaporated in vacuo and the residue was dissolved in 100 mL ethyl acetate. This organic solution was washed with 2×50 mL 10%$KHSO_4$ and brine. The organic phase was dried over $MgSO_4$, filtered and the solvent was evaporated in vacuo to afford 1.4 g (77%) of the title product as a yellow oil. Mass spectral analysis for $C_{19}H_{32}N_4O_6$: M+H=412.

EXAMPLE 129 phenylmethyl(2S,4Z)-2-[[(1,1-dimethylethoxy)carbonyl]amino]-5-(6,7,8,9-tetrahydro-3-oxo-3H,5H-[1,2,4]oxadiazolo[4,3-a]azepin-5-yl)-4-pentenoate

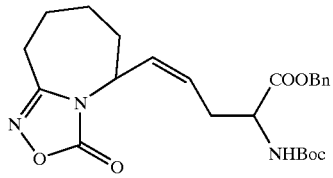

Ex 129a)

To a flask was added the product of Ex-131j (1 g, 0.004 mol) and triphenylphosphine (1.08 g, 4.1 mol). The mixture was placed into an oil bath which held a constant temperature of 110° C. for 16 hours. When the reaction cooled, the glassy solid was tritrated with diethyl ether for 10 hours. The phosphonium bromide was isolated as a fine white powder (0.93 g, 0.002 mol) in 50% yield. $^{31}$p NMR (CDCl$_3$, 300 MHz) d 22(s). Chemical Analysis: $C_{26}H_{26}N_2O_2BrP$

|  | carbon | hydrogen | nitrogen | bromine |
|---|---|---|---|---|
| calculated | 61.31 | 5.14 | 5.50 | 15.69 |
| found | 58.64 | 5.19 | 5.64 | 17.46 |

Ex-129b)

A solution of BH$_3$ (1M)(900 mL) in THF was cooled to 0° C. in an ice bath. To this solution was added a solution of Boc-Asp-OBn(150 g, 0.464 mol) in dry THF (300 mL) drop wise via an addition funnel. The reaction stirred at 0° C. for 2.5 hours. To the reaction was added a 5% glacial acetic acid methanol solution slowly. After 20 minutes the solvents were removed in vacuo and the residue was partitioned between ethyl acetate and 1N hydrochloric acid. The aqueous layer was back washed with ethyl acetate (1x). The combined organics were washed with brine(2x) then with saturated sodium bicarbonate, dried over magnesium sulfate anhydrous and removed under reduced pressure. The pale yellow oil was purified by running it through a plug of silica (650 g) to afford the aspartic alcohol (106 g) in 74% yield.

Ex-129c)

The product of Ex-129b (10.05 g, 0.033 mol) was then combined with 1-ethyl-3-(3-dimethylamino-propyl)carbodiimide (EDC)(26.65 g, 0.139 mol) and DMSO(10 mL) in methylene chloride(125 mL). A stream over nitrogen was passed over the solution and exhausted into a bleach solution. The reaction was cooled in an ice bath. To the reaction, a slurry at this point, was added dichloroacetic acid(4.19 g, 0.033 mol) slowly. After ½ hour the ECD dissolved and the ice bath was removed. The reaction stirred over night. To the reaction was added DI water(50 mL) and methylene chloride(50 mL). The organics were collected and washed with brine (3x50 mL), dried over magnesium sulfate anhydrous, then removed under reduced pressure. The product was purified using flash chromatography with 1:1 ethyl acetate:hexanes to afford the aspartic aldehyde (7.5 g, 0.024 mol) in 75% yield. Mass Spec: m/z308.4(M+H), m/z314.4(M+Li), m/z264.3(M-CO$_2$), m/z208.3(M-Boc).

Ex-129d)

To a 50 mL 3-neck round bottom flask fitted with an addition funnel is added the product of example 5a in 20 mL of THF. The solution is cooled to −78° C. in a dry ice bath. To this solution is added potassium bis(trimethylsilyl)amide (0.5M) slowly so that the temperature does not raise above −72° C. The reaction is stirred at −78° C. for 15 minutes. To the reaction is added the product of example 5c dropwise so that the temperature does not raise above −72° C. The reaction is stirred for an additional 45 minutes then the dry ice bath is removed and is stirred at room temperature for 4 hours. To the reaction is added a saturated solution of ammonium chloride. The organics are collected and washed with brine(3x25 mL), dried over magnesium sulfate anhydrous, removed under reduced pressure. The product is purified utilizing flash chromatography with 30:70 ethyl acetate:hexane to afford the title product.

EXAMPLE 130 a-amino-5-fluoro-6,7,8,9-tetrahydro-3-oxo-3H,5H-[1,2,4]oxadiazolo[4,3-a]azepine-5-hexanoic acid

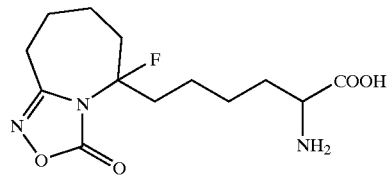

EXAMPLE 131

N-[(1,1-dimethylethoxy)carbonyl]-S-[(6,7,8,9-tetrahydro-3-oxo-3H,5H-[1,2,4]oxadiazolo[4,3-a]azepin-5-yl)methyl]-L-cysteine

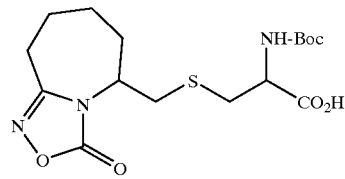

Ex-131a)

Anhydrous HCl was bubbled into a mixture of 25 g (0.14 moles) of 2-aminopimellic acid in 500 ml of MeOH until the solid was dissolved. After standing for 18 hours, the reaction was concentrated to afford 33.5 g (100%) of the bis-methyl ester as a white solid HCl salt. The HCl salt product was neutralized by addition of a small amount of water containing 1 equivalent of sodium bicarbonate. The aqueous mixture was extracted with EtOAc and the organic extract was dried (MgSO4), filtered and concentrated to afford 22 g of the amino-pimelate.

Ex-131b)

A solution of 17 g (0.084 moles) of the product of Ex-131a in 900 ml of p-cymene was stirred at reflux for two days. All solvent was removed in vacuo and the residue was recrystallized from cyclohexane to afford 12.2 g (85%) of 7-(methoxycarbonyl)caprolactam as an off-white solid. $^1$H NMR (CDCl$_3$, 300 MHz) d 1.5–2.5 (m, 8H), 3.7 (s, 3H), 4.0 (m, 1H), 6.4 (s, 1H). Melting Point (Mettler FP900) 79.5–85.8° C.

Ex-131c)

To a solution of the product of Ex-131b (70.01 g, 0.409 moles) in dichloromethane (500 ml) was added Trimethyloxonium tetrafluoroborate(75.68 g, 0.512 moles). The solution was stirred at reflux for two hours. The reaction cooled to room over 1 hour. The pH was adjusted to 7.0 with saturate Sodium hydrogen carbonate (700 ml). The organic layer was washed with brine, dried over Magnesium sulfate, filtered and concentrated under reduced pressure. The resulting oil was chromatographed to give 77.78 g (100% crude yield) of the imino methyl ether as an oil.
Ex-131d)

A solution of the product of Ex-131c (77.78 g, 0.409 moles) in methanol (400 ml) was stirred under $N_2$ for 5 minutes. To this solution was added Hydroxylamine hydrochloride (36.48 g, 0.525 moles). The reaction was stirred at reflux for 2 hours and at room temperature for 6 hours before the solvent was removed under reduced pressure. The resulting brownish slurry was mixed with dichloromethane (500 ml) and deionized water (500 ml). The pH of the water layer was adjusted to 9.0 with Potassium carbonate. The solution stirred 1 hour under $N_2$. The organic layer was separated, dried over Magnesium sulfate, filtered, and evaporated under reduced pressure to afford the hydroxamidine (74.30 g, 98% crude yield).
Ex-131e)

A solution of the product of Ex-131d (74.30 g, 0.399 moles) in dichloromethane (500 ml) was placed in an ice bath and stirred under $N_2$ for 20 minutes. To this solution was added a suspension of 1,1-carbonyldiimidazole (82.90 g, 0.511 moles) in dichloromethane (500 ml). The reaction mixture was stirred in an ice bath under $N_2$ for 1 hour. The reaction mixture removed from the ice bath was stirred under $N_2$ for 12 hours. To reaction mixture was added Potassium hydrogen sulfate (500 ml, 10%) and stirred under $N_2$ for 1 hour. The organic layer was separated, washed with brine, dried over Magnesium sulfate, filtered and evaporated under reduced pressure. The crude product was chromatographed to yield 35.53 g (41%) of the oxadiazolinone as a white solid. $^1$H NMR (CDCl$_3$, 300 MHz) d 1.2–1.3 (m, 2H), 1.6–1.8 (m, 1H), 1.9–2.0 (m, 2H), 2.3–2.5 (m, 2H), 2.7–2.9 (dd, 1H), 3.7 (s, 3H), 4.8 (m, 1H) $^{13}$C NMR (CDCl$_3$, 300 MHz) d 24.86, 26.20, 26.48, 30.40, 53.30, 56.18, 159.03, 161.17, 169.32 Melting Point (Mettler FP900) 69.7–74.1° C.
Ex-131f)

A solution of the product of Ex-131e (17.47 g, 0.082 moles) in Tetrahydrofuran (300 ml) stirred under $N_2$ for 5 minutes. To this solution was added Lithium borohydride (51.0 ml, 0.103 moles). The reaction stirred under $N_2$ for 90 minutes. The solvent was removed under reduced pressure. The white residue was dissolved in Ethyl acetate (200 ml) and Potassium hydrogen sulfate (200 ml, 10%). The organic layer was separated, washed with brine, dried over Magnesium sulfate, filtered and evaporated under reduced pressure. The resulting residue was chromatographed to yield 14.2 g (94%) of the hydroxymethyl product. $^1$H NMR (CDCl$_3$, 300 MHz) d 1.5–1.6 (m, 1H), 1.6–1.9 (m, 3H), 1.9–2.0 (m, 1H), 2.1–2.2 (m, 1H), 2.6–2.7 (dt, 1H), 2.8–2.9 (dd, 1H), 3.1 (s, 1H), 3.8–3.9 (d, 2H), 4.1–4.2 (m, 1H) 13C NMR (CDCl$_3$, 300 MHz) d 25.04, 25.28, 25.97, 29.50, 56.46, 62.24, 160.16, 161.10 Melting Point (Mettler FP900) 105.9–108.5° C.
Ex-131g)

To a solution of the product of Ex-131f (5.6 g, 0.030 moles) in dichloromethane (125 ml) was added Carbon tetrabromide (15.27 g, 0.046 moles). The reaction vessel was place in an ice bath and stirred for 30 minutes under nitrogen. To this mixture was added Triphenylphosphine (16.07 g, 0.061 moles). The mixture stirred 1 hour under nitrogen. The mixture was removed from the ice bath and stirred at room temperature under nitrogen for 12 hours. The solvent was removed under reduced pressure. The brown residue was triturated with ether (300 ml). The solvent was removed under reduced pressure. The residue was chromatographed to yield 6.70 g of the bromomethyl product. $^1$H NMR (CDCl$_3$, 300 MHz) d 1.5–1.6 (m, 1H), 1.6–1.9 (m, 3H), 1.9–2.0 (m, 1H), 2.1–2.2 (m, 1H), 2.6–2.7 (dt, 1H), 2.8–2.9 (dd, 1H), 3.4–3.5 (d, 2H), 4.4 (m, 1H) $^{13}$C NMR (CDCl$_3$, 300 MHz) d 23.48, 25.21, 26.03, 29.85, 30.29, 54.63, 159.19, 160.05
Ex-131h)

To a solution of Boc L-cysteine (5.1 g, 0.023 moles) in Dimethylformamide (70 ml) was added Sodium hydride (1.92 g, 0.048 moles) and stirred under nitrogen for 15 minutes. To this solution was added a solution of the product of Ex-131g (5.0 g, 0.020) in Dimethylformamide (30 ml). The reaction stirred 12 hours under nitrogen. The reaction was quenched with Potassium hydrogen sulfate (300 ml, 10%). The solution was concentrated under reduced pressure. The residue was purified by reverse phase HPLC to yield 7.0 g (91%) of the title product as a white fluffy, hydroscopic solid. $^1$H NMR (CDCl$_3$, 300 MHz) d 1.4–1.6 (s, 9H), 1.7–2.3 (m, 5H), 2.4–2.6 (t, 1H), 2.8–3.2 (m, 4H), 4.2–4.6 (m, 2H), 5.2–5.4 (m, 3H).

EXAMPLE 132

S-[(6,7,8,9-tetrahydro-3-oxo-3H,5H-[1,2,4] oxadiazolo[4,3-a]azepin-5-yl)methyl]-L-cysteine, monohydrochloride

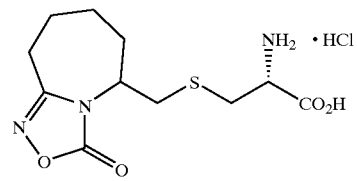

Ex-132)

A solution of the product from Ex-131 (1.32 g 0.0034 moles) was treated with 2 N HCl (8 ml), the pH was adjusted to 2, and stirred under $N_2$ for 1 hour. The product was purified by reverse phase HPLC and then lyophilized to give 0.78 g (79.6%) of the title product as a white solid. $^1$H NMR (CDCl$_3$, 300 MHz) d 1.7–2.3 (m, 5H), 2.4–2.6 (t, 1H), 2.8–3.2 (m, 4H), 4.2–4.6 (m, 2H), 5.2–5.4 (m, 3H).

EXAMPLE 133

3-[[(6,7,8,9-tetrahydro-3-oxo-3H,5H-[1,2,4] oxadiazolo[4,3-a]azepin-5-yl)methyl]sulfinyl]-L-alanine, monohydrochloride

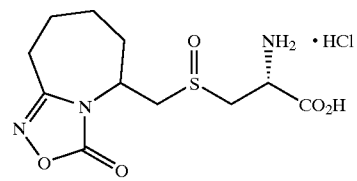

Ex-133)

A solution of the product from Ex-132 (0.039 g 0.00012 moles) in deionized water (5 ml) was placed in an ice bath and stirred under nitrogen for 30 minutes. To this solution was added Hydrogen peroxide (0.25 ml, 0.00012 moles) in formic acid (0.25 ml). The reaction vessel stirred in an ice bath under nitrogen for 1.5 hours. The reaction mixture continued to stir while the solution warmed to room temperature. Product was purified on reverse phase HPLC to give 0.030 g (75%) of the title product as a thick yellow oil. $^1$H NMR (CDCl$_3$, 300 MHz) d 1.4–1.6 (m, 6H), 2.4–2.5 (m, 1H) 2.6–2.7 (m, 1H), 3.1–3.2 (m, 4H), 3.3–3.4 (m, 3H), 3.6–3.7 (m, 1H), 4.0–4.2 (m, 2H)

EXAMPLE 134

3-[[(6,7,8,9-tetrahydro-3-oxo-3H,5H-[1,2,4]oxadiazolo[4,3-a]azepin-5-yl)methyl]sulfonyl]-L-alanine, monohydrochloride

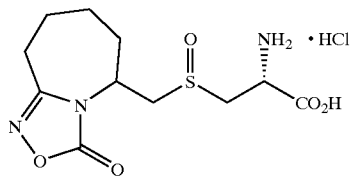

Ex-134)

A solution of Hydrogen peroxide (10 ml, 0.009 moles) in formic acid (10 ml) was placed in an ice bath, under nitrogen and stirred 30 minutes. To this solution a solution of the product of Ex-132 (1.0 g, 0.0031 moles) in deionized water (15 ml) was added. The reaction vessel remained in the ice bath, stirring, for 2 hours. The reaction vessel was removed from the ice bath and stirred while warming to room temperature. The reaction solution was lyophilized to afford 1.03 g (94%) of the title product as a yellow solid. $^1$H NMR (CDCl$_3$, 300 MHz) d 1.4–1.9 (m, 6H), 2.5–2.8 (m, 3H), 3.5–4.1 (m, 4H) 4.2–4.4 (m, 1H)

EXAMPLE 135 methyl a-(acetylamino)-6,7,8,9-tetrahydro-g,3-dioxo-3H,5H-[1,2,4]oxadiazolo[4,3-a]azepine-5-pentanoate

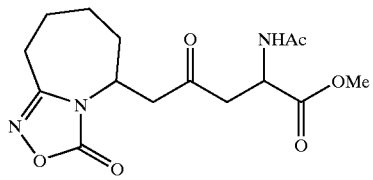

Ex-135a)

A sample of 2-nitroethanol (10 g, 110 mmol) was added over a period of 30 minutes to a mixture of sodium acetate (2.5 g) and acetic anhydride (13 g, 127 mmol) cooled in ice bath and maintained under a N$_2$ atmosphere. After 1 hour of stirring, the ice bath was removed and the mixture was stirred for 12 hours at room temperature. The reaction was diluted with 200 mL water and extracted with 3×100 mL EtOAc. The combined extracts were washed with brine, dried (MgSO$_4$) and stripped of all solvent in vacuo to afford the 2-nitro ethylacetate as a clear oil.

Ex-135b)

The product of Ex-135a (13.3 g, 100 mmol) was dissolved in 15 mL acetonitrile which was added to a solution of 1 morpholino cyclohexene (18.4 g, 110 mmol) in 30 mL AcCN at −20° C. under N$_2$. After the addition was complete stirring was continued for 16 hours at room temperature. After 40 mL of 1 N HCl was added to the solution, stirring was continued for 4 more hours. The mixture was diluted with 100 mL water and extracted with 3×100 mL EtOAc. The combined organic phase was washed with brine, dried (MgSO$_4$) and evaporated in vacuo to yield 14.5 g 2-(2-nitroethyl)cyclohexanone as dark oil (85% overall yield). Mass spectral analysis for C$_8$H$_{13}$NO$_3$: M$^+$H=172 and M$^+$Li=178.

Ex-135c)

The product of Ex-135b (3.42 g, 20 mmol) in 25 mL formic acid was refluxed for 30 minutes in the presence of H$_2$N—OSO$_3$H (2.48 g, 22 mmol). The formic acid was removed in vacuo. The residual oil was dissolved in a mixture of water (40 mL) and AcCN (10 mL) and the isomers were separated on preparative HPLC using AcCN/H$_2$O (0.05% TFA) gradient (10–25% AcCN in 30 minutes) to yield 7-(2-nitroethyl)caprolactam: 1.95 g (52%). Mass spectral analysis for C$_8$H$_{14}$N$_2$O$_3$: M$^+$H=187.

Ex-135d)

7-(2-nitroethyl)caprolactam (5.5 g; 0.03 mol) was combined with trimethyloxonium tetrafluoroborate (5.0 g; 0.033 mol) and dissolved/suspended in 50 ml of CH$_2$Cl$_2$. The mixture was stirred for 18 hours, affording a clear solution. Saturated NaHCO$_3$ (50 mL) was added and the mixture stirred until gas evolution ceased and the pH was greater than 8. The layers were separated, the organic phase dried over MgSO$_4$ and concentrated in vacuo to yield 5.8 g of the iminoether as an oil.

Ex-135e)

The product of Ex135-d was combined with hydroxylamine hydrochloride (4.2 g; 0.028 mol) and ethanol (50 mL) then stirred at reflux for one hour. The mixture was cooled and concentrated in vacuo. The residue was partitioned between saturated NaHCO$_3$/CH$_2$Cl$_2$. The organic layer was dried over MgSO$_4$ and concentrated in vacuo to yield the hydroxamidine as an oil.

Ex-135f)

The product of Ex-135e was combined with 1,1'-carbonyldiimidazole (4.5 g; 0.028 mol), dissolved in 50 mL of CH$_2$Cl$_2$, and stirred for 18 hours. The reaction mixture was washed with 10% KHSO$_4$ to remove excess imidazole. The organic solution was dried over MgSO$_4$ and concentrated in vacuo. The residue was chromatographed on Merck silica, eluting with 40% EtOAc/hexane. The desired product eluted first off the column and crystallized upon concentration to yield 3.1 g of the oxadiazolinone as a white powder. Mass spectra for C$_9$H$_{13}$N$_3$O$_4$, M+H=228 $^1$H NMR (CDCl$_3$) d 1.4 to 1.6, m (1H); 1.75 to 1.86, m (2H); 1.95 to 2.19, m (3H); 2.28 to 2.39, m (1H); 2.48 to 2.62, m (2H); 2.91 to 2.98 & 2.98 to 3.01, d of d of t (1H); 4.28 to 4.38, m (1H); 4.38 to 4.54, m (2H).

Ex-135h)

The product of Ex-135f (5.0 g; 0.022 mol) was combined with methyl N-acetylacrylate (3.2 g; 0.024 mol) and tetramethylguanidine (0.55 mL) in 50 mL of CH$_2$Cl$_2$. The reaction mixture was heated at reflux for 36 hours. The reaction mixture was concentrated and the residue was chromatographed on silica eluting with EtOH/EtOAc to afford two products. The more polar component was isaolated to afford 1 g of the title product. Mass spectra for C$_{15}$H$_{21}$N$_3$O$_6$, M+H=340 $^1$H NMR (CDCl$_3$) d 1.49, t (1H); 1.55 to 1.85, m (2H); 1.85 to 2.05, m (2H); 2.05, t (3H); 2.38 to 2.45, m (2H); 2.48 to 2.72, m (2H); 2.88 to 2.98, d of d (1H); 3.44, s (1H); 3.72, s (3H); 4.25 to 4.34, m (1H); 4.55 to 4.7, m (2H).

EXAMPLE 136 methyl a-(acetylamino)-g,g-difluoro-6,7,8,9-tetrahydro-3-oxo-3H,5H-[1,2,4]oxadiazolo[4,3-a]azepine-5-pentanoate

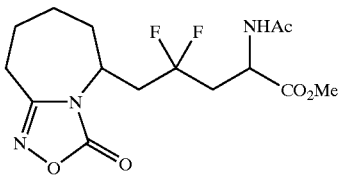

Ex-136)

The product of Ex-135 (200 mg; 0.00059 mol) is dissolved in CH$_2$Cl$_2$ (5.0 mlL) and (diethylamino)sulfur trifluoride (DAST) (190 mg: 0.0018 mol) is added and the reaction mixture is stirred for 18 hours. The reaction is quenched with water. The organic layer is dried over MgSO$_4$ and concentrated to afford the title product.

EXAMPLE 137 methyl a-(acetylamino)-6,7,8,9-tetrahydro-g-nitro-3-oxo-3H,5H-[1,2,4]oxadiazolo[4,3-a]azepine-5-pentanoate

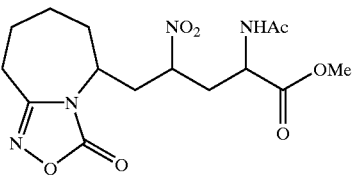

Ex-137)

The less polar component from Ex-135 was isolated to afford 5 g of the title product. Mass spectra for C$_{15}$H$_{22}$N$_4$O$_7$, M+H=371 $^1$H NMR (MeOD) d 1.5, t (1H); 1.7 to 2.9, m (3H); 1.95 to 2.2, m (7H); 2.25 to 2.8, m (4H); 2.95, t (1H); 3.7 to 3.8, m (3H); 4.2 to 4.75, m (3H); 6.35 to 6.6, m (1H).

EXAMPLE 138 methyl a-(acetylamino)-6,7,8,9-tetrahydro-g-methylene-3-oxo-3H,5H-[1,2,4]oxadiazolo[4,3-a]azepine-5-pentanoate

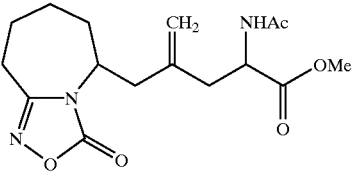

Ex-137)

Methyltriphenylphosphonium bromide (360 mg; 0.001 mol) is dissolved/suspended in THF (5.0 mL) then cooled to −78° C. n-BuLi is added and the temperature is raised to −40° C. for one hour. The mixture is recooled to −78° C. and the product of example 11 (200 mg; 0.00059 mol) is dissolved in THF and added to the mixture. The reaction mixture is allowed to warm to room temperature. Saturated NH$_4$Cl (5.0 ml) is added and the mixture is stirred for one hour. The organic layer is separated and dried over MgSO$_4$ and concentrated. The residue is chromatographed on silica gel. Elution with EtOAc/hexane affords the title product.

EXAMPLE 139

N-[(1,1-dimethylethoxy)carbonyl]-3-[[(6,7,8,9-tetrahydro-3-oxo-3H,5H-[1,2,4]oxadiazolo[4,3-a]azepin-5-yl)methyl]amino]-L-alanine

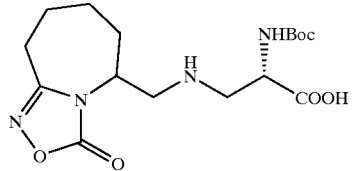

Ex-139a)

A solution of 8 mL (16 mmol) 2M oxalylchloride in CH$_2$Cl$_2$ was diluted with 15 mL CH$_2$Cl$_2$. This solution was cooled to −60° C. and 5 mL (70 mmol) of DMSO was added. After 5 minutes, 2.1 g (11.4 mmol) of the product of example 7f in 50 ml CH$_2$Cl$_2$ was added to the mixture. After 30 minutes stirring at −60° C. 10 mL (72 mmol) triethylamine was added to the reaction mixture and stirring was continued for 18 hours at room temperature. The reaction mixture was then diluted with 200 mL CH$_2$Cl$_2$ and washed with 2×100 mL 10% KHSO$_4$ and brine. The organic phase was dried over MgSO$_4$ and the solvent was evaporated to afford the aldehyde as an oil, 2 g (96%). Mass spectrak analysis for C$_8$H$_{10}$N$_2$O$_3$: M+H=183.

Ex-139)

A solution of 2 g (11 mmol) of the product of Ex-139a was dissolved in 15 mL DMF (containing 0.15 mL acetic acid) and allowed to react with 2.2 g (11 mmol) N-a-Boc-L-diaminopropionic acid. After 15 minutes stirring, 1.25 g (20 mmol) NaCNBH$_3$ was added and stirring was continued for 18 hours. The DMF was evaporated in vacuo and the residue was dissolved in 100 mL ethyl acetate. This solution was washed with 2×50 mL 10%KHSO$_4$ and brine. The organic phase was dried over MgSO$_4$, filtered and the solvent was evaporated in vacuo to afford the title product as an oil, 3.7 g (91%). Mass spectral analysis for C16H26N4O6: M+H= 371.

EXAMPLE 140 methyl(2S,4Z)-2-[[(1,1-dimethylethoxy)carbonyl]amino]-6-(6,7,8,9-tetrahydro-3-oxo-3H,5H-[1,2,4]oxadiazolo[4,3-a]azepin-5-yl)-4-hexenoate

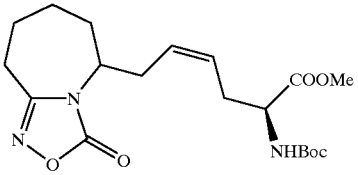

Ex-140)

The product of Ex-149 is allowed to stir at reflux in methanol containing a catalytic amount of acid. Evaporation of the solvent in vacuo affords the title product.

EXAMPLE 141

(3Z)-2-amino-6-(6,7,8,9-tetrahydro-3-oxo-3H,5H-[1,2,4]oxadiazolo[4,3-a]azepin-5-yl)-4-hexenoic acid

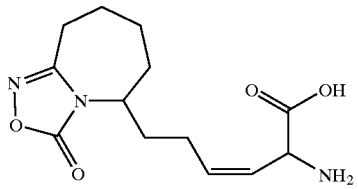

Ex-141a)

A solution of BH$_3$ (1M)(26 mL) in THF was cooled to 0° C. in an ice bath. To this solution was added a solution of the product of Ex125e (5.0 g, 0.025 mol) in dry THF (25 mL) drop wise via an addition funnel. The reaction stirred at 0° C. for 2.5 hours. To the reaction was added a 3% hydrogen peroxide at a pH of 10, adjusted by potassium carbonate. After 60 minutes, ethyl acetate(50 mL) was added and was partitioned between brine(50 mL). The organics were collected and dried over magnesium sulfate anhydrous then removed under reduced pressure. The pale yellow oil was purified by flash chromatography using 1:1 ethyl acetate-:hexane to afford hydroxypropyl product(2.42 g) in 44% yield. $^1$H NMR (CDCl$_3$, 300 MHz) d 1.4–2.2(m, 11H), 2.51 (t, 1H), 2.89(dd, 1H), 3.61(q, 2H), 4.25(m, 1H).

Ex-141b)

The procedure of Ex-125g was utilized with the product of Ex-141a to afford the bromopropyl product in 98% yield. $^1$H NMR (CDCl$_3$, 300 MHz) d 1.38–2.15(m, 11H), 2.51 (t, 1H), 2.95(dd, 1H), 3.42(m, 2H), 4.21(m, 1H).

EX-141c)

The procedure of Ex-125h was utilized with the product of Ex-141b to afford the phosphonium bromide in 98% yield. $^1$H NMR (CDCl$_3$, 300 MHz) d 1.38–2.61(m, 9H), 2.85 (dd, 1H), 3.60(m, 1H), 3.19(m, 1H), 4.45(m, 1H), 7.60–7.9(m, 15H).

Ex-141d)

To a 50 mL 3-neck round bottom flask fitted with an addition funnel was added the product of Ex-141c (4.93 g, 0.009 mol) in 20 mL of THF. The solution was cooled to –78° C. in a dry ice bath. To this solution was added potassium bis(trimethylsilyl)amide (0.5M)(10 mL, 0.020 mol) slowly so that the temperature would not raise above –72° C. The reaction stirred at –78° C. for 15 minutes. To the reaction was added Garner's Aldehyde (2.62 g, 0.012 mol) drop wise so that the temperature did not raise above –72° C. The reaction stirred for an additional 45 minutes then the dry ice bath was removed and stirred at room temperature for 4 hours. To the reaction was added a saturated solution of ammonium chloride. The organics were collected and washed with brine(3×25 mL), dried over magnesium sulfate anhydrous, removed under reduced pressure. The product was purified utilizing flash chromatography with 30:70 ethyl acetate:hexane to afford the protected amino alcohol (1.02 g, 0.002) in 39.9% yield. $^1$H NMR (CDCl$_3$, 300 MHz) d 1.49(s, 9H), 1.59–3.0 (m, 15H), 3.65(d, 1H), 4.1(m, 2H), 4.3(m, 1H), 4.6(bs, 1H), 5.40(m, 2H). Mass Spec m/z 208.2(M+H), m/z 430.2(M+Na), m/z 308.2(M+H-100).

Ex-141e)

To a solution of the product of Ex-141d (1 g, 0.003 mol) in methylene chloride(20 mL) was added triflouroacetic acid(4 mL). The reaction stirred for two hours then a solution of 5% potassium carbonate was added. The organ-ics were collected and washed with brine(3×20 mL), dried over magnesium sulfate anhydrous, removed under reduced pressure. To the resulting residue was added acetone(20 mL). To this solution was added Jone's Reagent(8N, 20 drops). After 2 hours, the reaction was monitored by TLC and starting material remained. Twenty additional drops were pipetted in and the reaction stirred over night. To the reaction was added methanol(10 mL). To the slurry was added water (100 mL) and the reaction was purified by reverse phase chromatography to afford the title product.

EXAMPLE 142 a-amino-6,7-dihydro-3-oxo-3H,5H-pyrrolo[2,1-c][1,2,4]oxadiazole-5-pentanoic acid

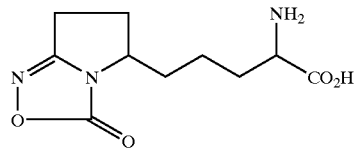

Ex-142a)

5-methoxy-2-pyrrolidinone is allowed to react with pentenyl magnesium bromide in THF at reflux for 3 h. The reaction solution is queched with saturated aqueous ammonium chloride and extracted with EA. The 5-(but-4-enyl)-2-pyrrolidinone is purified by column chromatography on silica gel.

Ex-142b)

A portion of the product of Ex-142a is allowed to react with of trimethyloxonium tetrafluoroborate in CH$_2$Cl$_2$ over a 16 hour period. The mixture is diluted with CH$_2$Cl$_2$ and washed with 5% NaHCO$_3$ and brine. The organic phase is dried over MgSO$_4$, filtered and the solvent was evaporated in vacuo to afford the iminoether.

Ex-142c)

The product of Ex-142b is allowed to react with hydroxylamine hydrochloride in MeOH for 16 hours. The methanol is evaporated to afford the hydroxamidine.

Ex-142d)

The product of Ex-142c is allowed to react with 1,1'-carbonyldiimidazole in CH$_2$Cl$_2$ for 24 hours at room temperature. The product is purified by column chromatography on silica gel.

Ex-142e)

A steam of ozone is allowed to pass through a CH$_2$Cl$_2$ solution of the product of Ex-142d until a blue color persists. A stream of argon is then allowed to pass through the reaction solution for 15 min. followed by the addition of Me$_2$S. The solution is allowed to stir at rt overnight. The solvent is removed under reduced pressure to yield the aldehyde.

Ex-142f)

DBU is added to a solution of Z-phosphonoglycinetrimethylester in CH$_2$Cl$_2$. A solution of Ex-142e CH$_2$Cl$_2$ is then added, and the resulting mixture is allowed to stir overnight at rt. The reaction mixture is then diluted with CH$_2$Cl$_2$ and extracted with HCl (1M) and brine. The product is purified by column chromatography on silica gel.

Ex-142 g)

Catalytic Rh(R,R-DIPAMP) is allowed to react with a solution of Ex-142f in MeOH under an atmosphere of H$_2$ at 60 psi and 50° C. for 20 h. The product is purified by column chromatography on silica gel.

Ex-142h)

The product of Ex-142h is hydrolyzed in 10% hydrochloric acid at reflux followed by concentration under reduced pressure. The resulting crude product residue is dissolved in water and extracted with diethyl ether. The title compound is isolated from the reaction mixture using $C_{18}$ reverse phase HPLC.

EXAMPLE 143 a-amino-6,7-dihydro-3-oxo-6-(trifluoromethyl)-3H, 5H-pyrrolo[2,1-c][1,2,4]oxadiazole-5-pentanoic acid

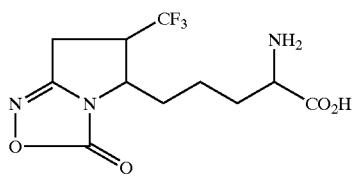

Ex-143a)

2-(3-nitro-propyl)-[1,3]dioxolane is prepared by the method of Knefeli et. al., Arch.Pharm. 316; 9; 1983; 773–781. 2-(3-nitro-propyl)-[1,3]dioxolane is then allowed to react with ethyl-4,4,4-trifluorocrotonate and DBU in acetonitrile at rt over a 16 h period. The solvent is removed and the residue is taken up in EA and extracted with $KHSO_4$ (10%) and brine. The solvent is evaporated in vacuo. The residue in MeOH is allowed to reduce under a $H_2$ atmosphere in the presence of Pd/C 10% at 60 psi and 50° C. The solvent is evaporated in vacuo. The product is purified by column chromatography on silica gel.

Ex-143b)

A portion of the product of Ex-143a is allowed to react with of trimethyloxonium tetrafluoroborate in $CH_2Cl_2$ over a 16 hour period. The mixture is diluted with $CH_2Cl_2$ and washed with 5% $NaHCO_3$ and brine. The organic phase is dried over $MgSO_4$, filtered and the solvent was evaporated in vacuo to afford the iminoether.

Ex-143c)

The product of Ex-143b is allowed to react with hydroxylamine hydrochloride in MeOH for 16 hours. The methanol is evaporated to afford the hydroxamidine.

Ex-143d)

The product of Ex-143c is allowed to react with 1,1'-carbonyldiimidazole in $CH_2Cl_2$ for 24 hours at room temperature. The product is purified by column chromatography on silica gel.

Ex-143e)

The product of Ex-143d is allowed to react with AcOH:$H_2O$ (70:30) for 16 hours at 70° C. The solvent is evaporated to afford the aldehyde.

Ex-143f)

DBU is added to a solution of Z-phosphonoglycinetrimethylester in $CH_2Cl_2$. A solution of 143c $CH_2Cl_2$ is then added, and the resulting mixture is allowed to stir overnight at rt. The reaction mixture is then diluted with CH2Cl2 and extracted with HCl (1M) and brine. The product is purified by column chromatography on silica gel.

Ex-143g)

Catalytic Rh(R,R-DIPAMP) is allowed to react with a solution of 143f in MeOH under an atmosphere of $H_2$ at 60 psi and 50° C. for 20 h. The product is purified by column chromatography on silica gel.

Ex-143)

The product of Ex-143g is hydrolyzed in 10% hydrochloric acid at reflux followed by concentration under reduced pressure. The resulting crude product residue is dissolved in water and extracted with diethyl ether. The title compound is isolated from the reaction mixture using $C_{18}$ reverse phase HPLC.

EXAMPLE 144 a-amino-5-(6,7-dihydro-3-oxo-3H,5H-pyrrolo[2,1-c][1,2,4]oxadiazol-5-yl)-2-furanacetic acid

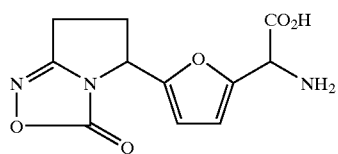

Ex-144a)

5-methoxy-2-pyrrlidinone is allowed to react with furan with catalytic PTSA in $CH_2Cl_2$ for 6 h at rt. The 5-furan-2-yl-pyrrolidin-2-one 144a is purified by column chromatography on silica gel.

Ex-144b)

A portion of the product of Ex-144a is allowed to react with of trimethyloxonium tetrafluoroborate in $CH_2Cl_2$ over a 16 hour period. The mixture is diluted with $CH_2Cl_2$ and washed with 5% $NaHCO_3$ and brine. The organic phase is dried over $MgSO_4$, filtered and the solvent was evaporated in vacuo to afford the iminoether.

Ex-144c)

The product of Ex-144b is allowed to react with hydroxylamine hydrochloride in MeOH for 16 hours. The methanol is evaporated to afford the hydroxamidine.

Ex-144d)

The product of Ex-144c is allowed to react with 1,1'-carbonyldiimidazole in $CH_2Cl_2$ for 24 hours at room temperature. The product is purified by column chromatography on silica gel.

Ex-144e)

The product of Ex-144d is allowed to react with ethyl 2-acetoxy-2-diphenylmethyleneaminoacetate and $TiCl_4$ in $CH_2Cl_2$ at rt for 4 h. The reaction mixture is quenched and treated with aqueous HCl (1M). The product is isolated from the reaction mixture using $C_{18}$ reverse phase HPLC.

Ex-144f)

The product of Ex-144e is allowed to hydrolyze in EtOH and aqueous LiOH. The reaction solution is acidified and concentrated in vacuo. The product is isolated from the reaction mixture using $C_{18}$ reverse phase HPLC.

EXAMPLE 145 a-amino-3-(6,7-dihydro-3-oxo-3H,5H-pyrrolo[2,1-c][1,2,4]oxadiazol-5-yl)-2-benzeneacetic acid

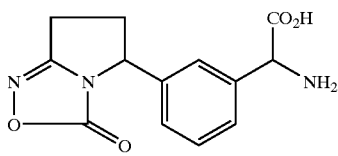

Ex-145a)

Magnesium is allowed to react with 2-(3-bromo-phenyl)-[1,3]-dioxolane in THF to form the Gringard. 5-methoxy-2-pyrrolidinone is allowed to react with the Gringard in THF at reflux for 3 h. The reaction solution is quenched with saturated aqueous ammonium chloride and extracted with EA. The product is purified by column chromatography on silica gel.

Ex-145b)

A portion of the product of Ex-145a is allowed to react with of trimethyloxonium tetrafluoroborate in $CH_2Cl_2$ over a 16 hour period. The mixture is diluted with $CH_2Cl_2$ and washed with 5% $NaHCO_3$ and brine. The organic phase is dried over $MgSO_4$, filtered and the solvent was evaporated in vacuo to afford the iminoether.

Ex-145c)

The product of Ex-145b is allowed to react with hydroxylamine hydrochloride in MeOH for 16 hours. The methanol is evaporated to afford the hydroxamidine.

Ex-145d)

The product of Ex-145c is allowed to react with 1,1'-carbonyldiimidazole in $CH_2Cl_2$ for 24 hours at room temperature. The product 145d is purified by column chromatography on silica gel.

Ex-145e)

The product of Ex-145e is allowed to react with $AcOH:H_2O$ (70:30)for 16 hours at 70° C. The solvent is evaporated to afford the aldehyde.

Ex-145f)

The product of Ex-145e is allowed to react with KCN and $NH_4Cl$ followed by hydrolysis in aqueous $H_2SO_4$. The product is isolated from the reaction mixture using $C_{18}$ reverse phase HPLC.

EXAMPLE 146 a-amino-4,5,5a,6,7,8,9,9a-octahydro-5-methyl-1-oxo-1H-[1,2,4]-oxadiazolo[4,3-a]quinoline-9-butanoic acid

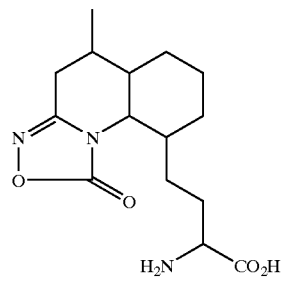

Ex-146a)

2-allyl-aniline is allowed to react with methylacetoacetate at 140° C. in a sealed vessel. The product is purified by column chromatography on silica gel.

Ex-146b)

The product 146a is allowed to react in concentrated $H_2SO_4$. The reaction mixture is poured onto water and the pH is adjusted to 7. The product is collected by filtration.

Ex-146c)

A steam of ozone is allowed to pass through a $CH_2Cl_2$ solution of the product of Ex-146b until a blue color persists. A stream of argon is then allowed to pass through the reaction solution for 15 min. followed by the addition of $Me_2S$. The solution is allowed to stir at rt overnight. The solvent is removed under reduced pressure to yield the aldehyde.

Ex-146d)

A solution of the aldehyde is allowed to react with anhydrous methanol, PTSA and trimethylorthoformate for 16 h at rt. The product 146d is purified by column chromatography on silica gel.

Ex-146e)

A mixture of the product of Ex-146d and platinum oxide in methanol is hydrogented at room temperature and 50 psi.

The catalyst is filtered washed with methanol and concentrated. The desired lactam 126c is purified by column chromatography on silica gel.

Ex-146f)

A portion of the product of Ex-146e is allowed to react with of trimethyloxonium tetrafluoroborate in $CH_2Cl_2$ over a 16 hour period. The mixture is diluted with $CH_2Cl_2$ and washed with 5% $NaHCO_3$ and brine. The organic phase is dried over $MgSO_4$, filtered and the solvent was evaporated in vacuo to afford the iminoether.

Ex-146g)

The product of Ex-146f is allowed to react with hydroxylamine hydrochloride in MeOH for 16 hours. The methanol is evaporated to afford the hydroxamidine.

Ex-146h)

The product of Ex-146g is allowed to react with 1,1'-carbonyldiimidazole in $CH_2Cl_2$ for 24 hours at room temperature. The product 145d is purified by column chromatography on silica gel.

Ex-146i)

The product of Ex-145h is allowed to react with $AcOH:H_2O$ (70:30)for 16 hours at 70° C. The solvent is evaporated to afford the aldehyde.

Ex-146j)

DBU is added to a solution of Z-phosphonoglycinetrimethylester in $CH_2Cl_2$. A solution of 146i $CH_2Cl_2$ is then added, and the resulting mixture is allowed to stir overnight at rt. The reaction mixture is then diluted with CH2Cl2 and extracted with HCl (1M) and brine. The product is purified by column chromatography on silica gel.

Ex-146k)

Catalytic Rh(R,R-DIPAMP) is allowed to react with a solution of 146j in MeOH under an atmosphere of $H_2$ at 60 psi and 50° C. for 20 h. The product is purified by column chromatography on silica gel.

Ex-146l)

The product of Ex-146k is hydrolyzed in 10% hydrochloric acid at reflux followed by concentration under reduced pressure. The resulting crude product residue is dissolved in water and extracted with diethyl ether. The title compound is isolated from the reaction mixture using $C_{18}$ reverse phase HPLC.

EXAMPLE 147

5-amino-2-[(6,7,8,9-tetrahydro-3-oxo-3H,5H-[1,2,4]oxadiazolo[4,3-a]azepin-5-yl)methyl]-1H-imidazole-4-carboxylic acid, monohydrochloride

Ex-147a)

To a solution of the product of Ex-125e in dioxane (200 mL) and water (135 mL) was added sodium periodate (15.11 g, 0.071 mol) and osmium tetraoxide (12 drops of a 1 ppm solution of osmium dioxide in n-BuOH/$H_2O$). The reaction was stirred at room temperature and monitor by thin layer chromatography for one day. Since the starting material had not completely reacted, additional osmium tetraoxide (12 drops of 1 ppm solution of osmium dioxide in n-BuOH/

H₂O) was added. A white precipitate was filtered off and the filtrate was removed under reduced pressure to the point where no dioxane remained. Additional water (75 mL) was then added to the aqueous layer and this aqueous mixture was washed with CH₂Cl₂ (3×75 mL). The organic layer was combined, dried over magnesium sulfate, and stripped of all solvent under reduced pressure to afford a yellow oil. Chromatographic (silica gel) purification of this material eluting with the 1:1, ethyl acetate:hexane afforded 4.0 g (67%) of the aldehyde. ¹H NMR (CDCl₃, 300 MHz) d 1.2–2.5 (m, 6H), 2.59 (q, 2H), 2.92 (m, 2H), 4.79 (m, 1H), 9.79 (ss, 1H). ¹³C NMR (CDCl₃, 75 MHz) d 24.12, 31.52, 32.00, 45.61, 49.10, 53.98, 159.9, 160.8, 198.1.

Ex-147b)

To a solution of the product from Ex-147a in acetone is added Jones reagent until the red color persists as described in *J. Chem. Soc.* 1956, 39. The reaction is then quenched with isopropyl alcohol and concentrated under reduced pressure. The residue is then partitioned between brine and methylene chloride. The organic layer is back washed with a solution of sodium carbonate. The water layer is then acidified with concentrated hydrochloric acid and the precipitate is filtered and washed with water to afford the carboxylic acid.

Ex-147c)

To a solution of the product of Ex-147b in methylene chloride is added a catalytic amount of DMF. Oxalyl chloride is added dropwise at room temperature and evolution of gas is observed. The reaction is followed by thin layer chromatography to determine when the reaction is complete. The completed reaction is concentrated under reduced pressure and the residue is dissolved in methylene chloride. The reaction mixture is cooled to 0° C. in an ice bath and ammonia is bubbled through it. The solvent is the removed under reduced pressure and the product is partitioned between brine and methylene chloride. The organic is dried over magnesium sulfate and solvent is removed under reduced pressure to afford the carboxamide.

Ex-147d)

To a solution of the product of Ex-147c in methylene chloride is added triethylamine. The reaction is cooled to 0° C. in an ice bath and 12% phosgene in toluene is added dropwise. The reaction is stirred until completed as noted by thin layer chromatography. The reaction is washed with brine, dried over magnesium sulfate, and concentrated under reduced pressure. The crude residue is chromatographed to afford the nitrile.

Ex-147e)

To a solution of ethanol saturated with hydrogen chloride is added portion-wise the product of Ex-147d. The reaction is allowed to warm to room temperature and is followed by thin layer chromatography. The completed reaction is concentrated and the residue is dissolved in ethanol to afford a solution of the ethyl acetimidate.

Ex-147f)

The product of Ex-147e is converted to the 2-amino, 3-ethoxycarbonyl-1,4-imidazol-1-yl utilizing the procedure published in *J. Chem Soc.* 1949, 1071.

Ex-147g)

The product of Ex-147f is hydrolyzed in 10% hydrochloric acid at reflux followed by concentration under reduced pressure. The resulting crude product residue is dissolved in water and extracted with diethyl ether. The product is purified on an ion exchange resin to produce the title product.

EXAMPLE 148 a-amino-6,7,8,9-tetrahydro-e-1H-imidazol-2-yl-3-oxo-3H,5H-[1,2,4]-oxadiazolo[4,3-a]azepine-5-hexanoic acid

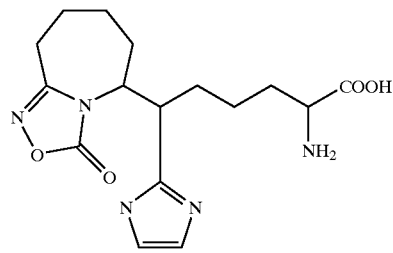

EXAMPLE 149 phenylmethyl(2S,4Z)-2-[[(1,1-dimethylethoxy)carbonyl]amino]-6-(6,7,8,9-tetrahydro-3-oxo-3H,5H-[1,2,4]oxadiazolo[4,3-a]azepin-5-yl)-4-hexenoate

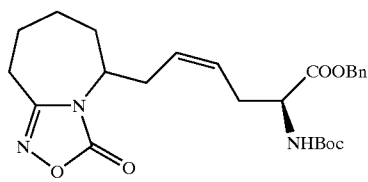

Ex-149)

To a 50 mL 3-neck round bottom flask fitted with an addition funnel was added the product of Ex-125 h (1.93 g, 0.004 mol) in 20 mL of THF. The solution was cooled to −78° C. in a dry ice bath. To he solution was added potassium bis(trimethylsilyl)amide (0.5M)(7.62 mL, 0.004 mol) slowly so that the temperature would not raise above −72° C. The reaction stirred at −78° C. for 15 minutes. To the reaction was added the product of example 5c (1.17 g, 0.004 mol) dropwise so that the temperature did not raise above −72° C. The reaction stirred for an additional 45 minutes then the dry ice bath was removed and stirred at room temperature for 4 hours. To the reaction was added a saturated solution of ammonium chloride. The organics were collected and washed with brine(3×25 mL), dried over magnesium sulfate anhydrous, removed under reduced pressure. The product was purified utilizing flash chromatography with 30:70 ethyl acetate:hexane to afford the title product (1.02 g, 0.002) in 57% yield. ¹H NMR (CDCl₃, 300 MHz) d 1.38(s, 9H), 1.4–2.6 (m, 10H), 2.92(d, 1H), 4.17(m, 1H), 4.38(m, 1H), 5.05(q, 2H), 5.40(m, 2H), 7.3(s,5H). ¹³C NMR (CDCl₃, 75 MHz) d 24.38, 25.0, 25.88, 26.54, 26.57, 28.73, 28.74, 30.11, 31.55, 54.04, 54.13, 67.60, 67.63, 127.3, 127.4, 128.2, 128.3, 128.8, 135.7, 159.9, 160.8, 172.1.

EXAMPLE 150

3-[ethyl[(6,7,8,9-tetrahydro-3-oxo-3H,5H-[1,2,4]oxadiazolo[4,3-a]azepin-5-yl)methyl]amino]-L-alanine

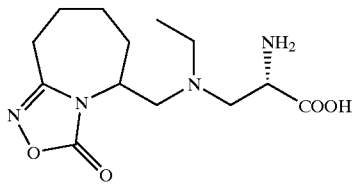

Ex-150)

A solution of 0.4 g (1 mmol) of the product from Ex-157 is dissolved in 25 mL 1 N HCl and the mixture is stirred for 8 hours at room temperature. The reaction mixture is diluted with 200 mL $H_2O$ and purified on preparative HPLC using acetonitrile/$H_2O$ (0.05% TFA) gradient from 0–40% AcN in 30 minutes to afford the title product.

EXAMPLE 151

(2S)-2-[[(phenylmethoxy)carbonyl]amino]-4-[[(6,7,8,9-tetrahydro-3-oxo-3H,5H-[1,2,4]oxadiazolo[4,3-a]azepin-5-yl)carbonyl]amino]butanoic acid

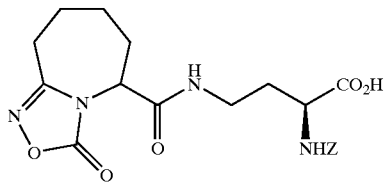

Ex-151a)

Potassium hydroxide (2.27 g, 0.040 mol) was dissolved in 31 ml THF and 25 ml deionized water and cooled to 5° C. The product of Ex-131e (5.00 g,0.202 mol) was dissolved in 20 ml THF and slowly added to the KOH/water/THF solution while stirring vigorously to prevent freezing. After stirring at reduced temperature for 2 hours, the mixture was transferred to a stirring mixture of 200 ml toluene and 50 ml 1 N potassium bisulfate. The layers were separated and the organics were treated with magnesium sulfate, filtered and solvent was removed under reduced pressure to afford 4.5 g of the acid. $^{13}C$ NMR ($CDCl_3$, 400 MHz) d 25.21, 26.49, 26.70, 30.62, 56.42, 159.95, 161.61, 170.73

Ex-151b)

The product of Ex-151a (1.00 g, 0.0047 mol) was dissolved in methylene chloride (10 ml) and charged with 1,1'-carbonyldiimidazole (0.835 g, 0.005 mol). After stirring for 5 minutes, diaminobutyric acid (1.30 g, 0.005 mol) was added and the reaction mixture was stirred overnight (20 hours). The reaction was transferred into a stirring mixture of 50 ml 1 N potassium bisulfate and 200 ml toluene. The layers were separated, and the organic phase was treated with saturated sodium bicarbonate, then solid magnesium sulfate. This was filtered through a sintered glass funnel, and solvent was removed under reduced pressure to afford 295 mg (15%) of the title product. Analysis calcd. for $C_{20}H_{24}N_4O_7$+1.2$H_2O$

|  | carbon | hydrogen | nitrogen |
| --- | --- | --- | --- |
| calcd. | 52.91 | 5.86 | 12.34 |
| found | 52.94 | 6.01 | 11.97 |

EXAMPLE 152

N-[(phenylmethoxy)carbonyl]-O-[(6,7,8,9-tetrahydro-3-oxo-3H,5H-[1,2,4]oxadiazolo[4,3-a]azepin-5-yl)methyl]-L-serine

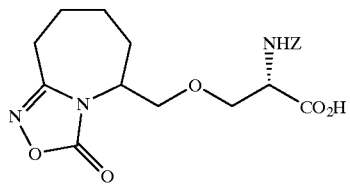

Ex-152a)

The product of Ex-131f (4.20 g, 0.0228 mol) was dissolved in 27 ml Pyridine and 50 ml Methylene Chloride and cooled to 0° C. in an ice bath under a nitrogen stream. Methane sulfonyl chloride (1.94 ml, 0.0251 mol) was added dropwise to the reaction vessel. After addition, the ice bath was removed and the reaction was allowed to warm to room temperature and stirred overnight (16 hour). The solvent was removed under reduced pressure, and excess pyridine was azeotroped using toluene. The residual solid was redissolved in 200 ml ethyl acetate and 50 ml 1 N potassium bisulfate. The layers were separated and the organic phase was treated with 50 ml brine. Layers were separated again, the aqueous layer was tested using thin layer chromatography (ethyl acetate, visualized by iodine) to ensure all organics were removed. The organic layer is treated with magnesium sulfate, filtered through a sintered glass funnel, then solvent removed under reduced pressure to afford the mesylate, (4.1 g, 68%). Elemental analysis calcd. for $C_9H_{14}N_2O_5S$

|  | carbon | hydrogen | nitrogen |
| --- | --- | --- | --- |
| calcd. | 41.21 | 5.38 | 10.68 |
| found | 41.29 | 5.73 | 10.45 |

$^{13}C$ NMR ($CDCl_3$, 400 MHz) d 24.48, 25.05, 25.93, 29.09, 37.97, 52.63, 66.58, 159.19, 160.02

Ex-152b)

N-Z-Serine (0.502 g, 0.0021 mol) was dissolved in THF (18 ml). This was cooled to 0° C. in an ice bath and slowly added Sodium Hydride (0.168 g, 0.0042 mol), with vigorous stirring. After gas evolution ceases, a solution of the product of Ex-152a (0.5 g, 0.0019 mol) was dissolved in THF (20 ml) and added to the Serine/NaH mixture slowly. Another 0.168 g of Sodium Hydride was added to the mixture. After 4.5 hours of stirring at 0° C., the reaction mixture was transferred to a stirring mixture of 50 ml 1 N potassium bisulfate, and 100 ml ethyl acetate. The layers were separated, and the organic phase was treated with magnesium sulfate, filtered and solvent removed under reduced pressure. Further chromatography using 50% ethyl acetate in hexane (visualized with iodine) produced 0.244 g (32%) of the title product.

EXAMPLE 153 bis(1,1-dimethylethyl)4-nitro4-[(6,7,8,9-tetrahydro-3-oxo-3H,5H-[1,2,4]oxadiazolo[4,3-a]azepin-5-yl)methyl]heptanedioate

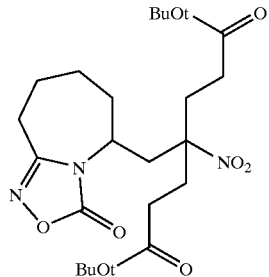

Ex-153)

The product of Ex-135f (227 mg; 0.001 mol) was combined with t-butyl acrylate (256 mg; 0.002 mol) and $K_2CO_3$ in 5 mL of DMF. The reaction mixture was stirred for 18 hours. The reaction mixture was then concentrated and the residue partitioned between $CH_2Cl_2$ and water. The organic layer was dried over $MgSO_4$ then concentrated. The residue crystallized and was triturated with $Et_2O$ to yield 354 mg of the title product as a solid. Anal. Calcd. for $C_{23}H_{37}N_3O_8C$: 57.13; H: 7.75; N: 8.69; Found: C: 57.24; H: 7.95, N: 8.53. Mass Spectra for $C_{23}H_{37}N_3O_8$ $M+NH_4=501$ $^1H$ NMR ($CDCl_3$) d 1.38 to 1.58, m (18H); 1.6 to 2.0, m (5H); 2.1 to 2.4, m (10 H); 2.48 to 2.62, m (2H); 2.82 to 3.02, m (1H); 4.3 to 4.5 m (1H).

EXAMPLE 154

S-[(6,7,8,9-tetrahydro-3-oxo-3H,5H-[1,2,4]oxadiazolo[4,3-a]azepin-5-yl)methyl]homocysteine

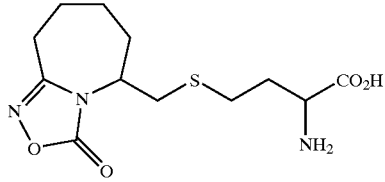

Ex-154a)

To a solution of Boc DL-homocysteine (1.90 g, 8 mmoles) in N-dimethylformamide (25 mL) was added Sodium hydride in 60% mineral oil dispersion (0.73 g, 18.3 mmoles) and stirred under nitrogen for ten minutes. To this solution was added the product from example 7 g (1.8 g, 7.3 mmoles) in N-dimethylformamide (10 mL). The reaction solution was stirred for 12 hours under nitrogen at room temperature. Solution was quenched with Potassium hydrogen sulfate (100 mL) and concentrated under reduced pressure. The product was purified by reverse phase HPLC to yield 2.08 g (71%) of Boc-protected product as a white fluffy, hydroscopic solid. Mass Spectra for $C_{17}H_{27}N_3O_6S_1$: $M+H=402$ Ex-154b)

The product from Ex-154a is dissolved in 2N HCl and allowed to stir for 4 hours. The reaction solution is diluted with de-ionized water and purified with reverse phase HPLC to afford the title product.

EXAMPLE 155

S-[2-(6,7,8,9-tetrahydro-3-oxo-3H,5H-[1,2,4]oxadiazolo[4,3-a]azepin-5-yl)ethyl]-L-cysteine

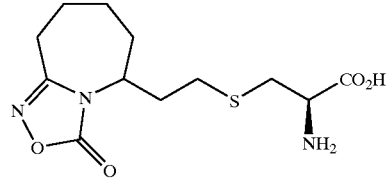

Ex-155a)

To a solution of Boc L-cysteine (1.16 g, 5.25 mmoles) in N-dimethylformamide (15 mL) was added Sodium hydride in 60% mineral oil dispersion (0.42 g, 10.5 mmoles) and stirred under nitrogen for ten minutes. To this solution was added the product from example 1 g (1.8 g, 7.3 mmoles) in N-dimethylformamide (10 mL). The reaction solution was stirred for 12 hours under nitrogen at room temperature. The solution was quenched with Potassium hydrogen sulfate (100 mL) and concentrated under reduced pressure. The product was purified by reverse phase HPLC to yield 1.87 g (89%) of Boc-protected product as a white, hydroscopic compound. Mass Spectra for $C_{17}H_{27}N_3O_6S_1$: $M+Na=424$ Ex-155b)

The product from Ex-155a is dissolved in 2N HCl and allowed to stir for 4 hours. The reaction solution is diluted with de-ionized water and purified with reverse phase HPLC to afford the title product.

EXAMPLE 156

S-[2-(6,7,8,9-tetrahydro-3-oxo-3H,5H-[1,2,4]oxadiazolo[4,3-a]azepin-5-yl)ethyl]homocysteine

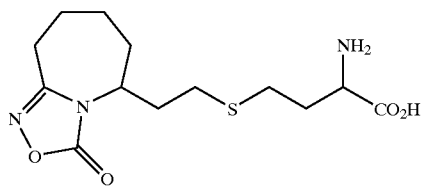

Ex-156a)

To a solution of Boc homocysteine (0.55 g, 2.36 mmoles) in N-dimethylformamide (15 mL) was added Sodium hydride in 60% mineral oil dispersion (0.19 g, 4.68 mmoles) and stirred under nitrogen for ten minutes. To this solution was added the product from Ex-125 g (0.49 g, 1.88 mmoles) in N-dimethylformamide (10 mL). The reaction solution was stirred for 12 hours under nitrogen at room temperature. The reaction solution was quenched with Potassium hydrogen sulfate (50 mL) and concentrated under reduced pressure. The product was purified by reverse phase HPLC to yield 0.50 g (64%) of the Boc-protected product as a white, hydroscopic compound. Mass Spectra for $C_{18}H_{29}N_3O_6S_1$: $M+H=416$ Ex-156b)

The product from ex-156a is dissolved in 2N HCl and is allowed to stir for 4 hours. The reaction solution is diluted with de-ionized water and purified with reverse phase HPLC to afford the title product.

EXAMPLE 157

N-[(1,1-dimethylethoxy)carbonyl]-3-[ethyl[(6,7,8,9-tetrahydro-3-oxo-3H,5H-[1,2,4]oxadiazolo[4,3-a]azepin-5-yl)methyl]amino]-L-alanine

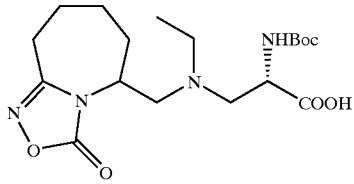

Ex-157)

To a solution of 3.7 g (10 mmol) of the product of Ex-139 was dissolved in 25 mL DMF (containing 0.25 mL acetic acid). This was allowed to react with 0.614 mL (11 mmol) of acetaldehyde with vigorous stirring for 15 minutes. To this mixture was then added 1.25 g (20 mmol) NaCNBH$_3$ and stirring was continued for 18 hours. The DMF was evaporated in vacuo and the residue was dissolved in 200 mL ethyl acetate. This solution was washed with 2×100 mL 10% KHSO$_4$ and brine. The organic phase was dried over MgSO$_4$, filtered and the solvent was evaporated in vacuo to afford the title product as a yellow oil, 2.1 g (52%). Mass spectral analysis for C18H30N4O6: M+H=399.

BIOLOGICAL DATA

The subject compounds of formula (I) have been or are expected to be found to inhibit nitric oxide synthase and posses useful pharmacological properties as demonstrated in one or more of the following assays:

In Vivo Assay

Mice were treated with an intraperitoneal injection of 12.5 mg/kg of endotoxin (LPS) with or without oral administration of the nitric oxide synthase inhibitors. Plasma nitrites were measured 5 hours post-treatment. The results show that the administration of the nitric oxide synthase inhibitor decreases the rise in plasma nitrites, a reliable indicator of the production of nitric oxide, induced by endotoxin.

TABLE 1

| | Low Dose LPS* | | |
|---|---|---|---|
| | in vivo | Effective Dose (p.o., mg/kg) | |
| Compound | 1 | 3 | 10 |
| Example 1 | 23% inh. | | 72% inh. |
| Example 3 | | 33% inh. | 64% inh. |

What is claimed is:
1. A compound having the formula:

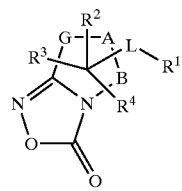

or a pharmaceutically acceptable salt thereof, wherein:
R$^1$ is selected from the group consisting of hydrogen, lower alkyl, lower alkenyl, lower alkynyl, OR$^5$, SR$^5$, S(O)R$^5$, S(O)$_2$R$^5$, C(O)R$^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, P(R$^5$)$_3$, C(O)R$^5$, OR$^5$, SR$^5$, S(O)R$^5$, S(O)$_2$R$^5$, S(O)R$^7$, S(O)$_2$R$^7$, SO$_2$NR$^5$R$^6$, NR$^5$SO$_2$R$^6$, CONR$^5$R$^6$, PO(OR$^5$)(OR$^6$), amidino, and guanidino, wherein all said substituents may be optionally substituted with one or more selected from the group consisting of halogen, lower alkyl, lower alkenyl, lower alkynyl, cycloalkyl, OR$^5$, SR$^5$, S(O)R$^5$, S(O)$_2$R$^5$, S(O)R$^7$, S(O)$_2$R$^7$, SO$_2$NR$^5$R$^6$, PO(OR$^5$)(OR$^6$), C(O)R$^6$, carboalkoxyalkyl, cyano, nitro, amidino, and guanidino, wherein R$^5$ and R$^6$ of SO$_2$NR$^5$R$^6$ and NR$^5$SO$_2$R$^6$ may be taken together to form a N-containing heterocycle, optionally substituted by one or more selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, and carboxyalkyl;

R$^1$ may be

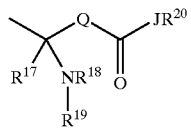

wherein J is selected from the group consisting of O, S and NR;

R is selected from the group consisting of hydrogen, lower alkyl, lower alkenyl, lower alkynyl, cycloalkyl, cycloalkenyl, heterocycle, aromatic hydrocarbon, alkylaryl, alkylheterocycle, all of which may be optionally substituted by one or more of alkyl, hydroxy, alkoxy, halogen, haloalkyl, cyano, amino, and nitro;

NR and R$^{20}$ may optionally form a heterocycle;

R$^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, C(O)R$^6$, carboalkoxyalkyl, CONR$^5$R$^6$, S(O)R$^5$, S(O)$_2$R$^5$, SO$_2$NR$^5$R$^6$, NR$^5$SO$_2$R$^6$, PO(OR$^5$)(OR$^6$), amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O)R$^8$, S(O)$_2$R$^8$, S(O)R$^{10}$, S(O)$_2$R$^{10}$, SO$_2$NR$^8$R$^9$, NR$^8$SO$_2$, PO(OR$^8$)(OR$^9$), amidino, and guanidino;

R$^{17}$ is selected from the group consisting of hydrogen, lower alkyl, hydroxyalkyl, alkoxyalkyl, haloalkyl, cycloalkyl, heterocycle, aromatic hydrocarbon, alkylaryl, and alkylheterocycle, all except hydrogen may be optionally substituted by one or more of alkyl, hydroxy, alkoxy, thiol, alkylthiol, halogen, haloalkyl, carboxyl, cyano, amino, and nitro;

$R^{18}$ is selected from the group consisting of hydrogen, hydroxyl, $R^{12}$, $S(O)R^{11}$, $SO_2R^{11}$, $CH_2OC(O)—R^{11}$, and $C(O)—R^{11}$;

$R^{18}$ and $R^{20}$ may be taken together to form a 5- or 6-membered heterocyclic ring containing two or more heteroatoms which may be optionally substituted by one or more of $R^{16}$;

$R^2$ and L may be taken together to form a 3 to 9 membered alicyclic or heterocyclic ring which may be optionally substituted by one or more of $R^{16}$;

$R^2$ and $R^{17}$ may be taken together to form a 4 to 9 membered alicyclic or heterocyclic ring which may be optionally substituted by one or more of $R^{16}$;

$R^2$ and $R^{18}$ may be taken together to form a 6 to 9 membered heterocyclic ring which may be optionally substituted by one or more of $R^{16}$;

L and $R^{17}$ may be taken together to form a 3 to 9 membered alicyclic or heterocyclic ring which may be optionally substituted by one or more of $R^{16}$;

L and $R^{18}$ may be taken together to form a 4 to 9 membered alicyclic or heterocyclic ring which may be optionally substituted by one or more of $R^{16}$;

$R^{17}$ and $R^{18}$ and may be taken together to form a 4 to 9 membered heterocyclic ring which may be optionally substituted by one or more of $R^{16}$;

$R^{17}$ and Q may be taken together to form a 3 to 9 membered alicyclic or heterocyclic ring which may be optionally substituted by one or more of $R^{16}$;

$R^{18}$ and Q may be taken together to form a 4 to 9 membered heterocyclic ring which may be optionally by one or more of $R^{16}$;

$R^{17}$ and $R^{20}$ and may be taken together to form a 5 to 9 membered heterocyclic ring which may be optionally substituted by one or more of $R^{16}$;

$R^{19}$ is hydrogen, $R^{11}$, or $C(O)—R^{11}$;

$R^{11}$ is selected from the group consisting of hydrogen, hydroxyl, alkenyl, alkynyl, heterocyclyl, aromatic hydrocarbon, cycloalkyl, dihydropyridyl, alkyl, alkylthiol, alkoxy, amino, and cycloalkoxy, which may be optionally substituted with one or more of amino, carboxyl, carboxamide, thioalkyl, aromatic hydrocarbon, alkyl, alkylaryl, hydroxy, alkoxy, halogen, trifluoromethyl, nitro, cyano, amino, heterocyclyl, alkylheterocycle, and alkylthiol, which may be optionally substituted with one or more of hydroxy, amino, guanidino, iminoalkyl;

$R^{12}$ is selected from the group consisting of hydrogen, alkyl, alkenyl, alkynyl, cycloalkyl, heterocycle, and aromatic hydrocarbon, all may be optionally substituted by one or more alkyl, hydroxy, alkoxy, halogen, trifluoromethyl, nitro, cyano, or amino groups;

$R^{20}$ is selected from the group consisting of hydrogen, lower alkyl, lower alkenyl, lower alkynyl, cycloalkyl, cycloalkenyl, aromatic hydrocarbon, heterocycle, alkylaryl, and alkylheterocycle, which may be optionally substituted by one or more of halogen, haloalkyl, cyano, nitro, —$CO_2R$, and —COR;

$R^{20}$ may also be selected from the group consisting of alkylhydroxy, alkylpolyhydroxy, alkyl(poly)oxyalkylcarbonyl, $CH_2C(=O)OR^{12}$, $CH_2C(=O)$ $NHR^{12}$, $CH_2OC(=O)R^{12}$, and $CH_2OC(—O)VR^{12}$, wherein the $CH_2$ may be optionally substituted by one or more of lower alkyl, cycloalkyl, heterocycle, aromatic hydrocarbon, amidino, guanidino, $CO_2H$, amino, hydroxy, thiol, halogen, haloalkyl, cyano, and nitro;

V is selected from the group consisting of O, S, $CH_2$, $CHR^{12}$, $C(R^{12})_2$, NH, and $NR^{12}$;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

G is $(CH_2)_2$ when A is $(CH_2)_2$ and B is $CH_2$; or

G is $CH_2$ when A is $(CH_2)_2$ and B is CH=CH; or

G is $CH_2$ when A is CH=CH and B is $(CH_2)_2$; or

G is $(CH_2)_2$ when A is CH=CH and B is $CH_2$; or

G is CH=CH when A is CH=CH and B is $CH_2$; or

G is CH=CH when A is $(CH_2)_2$ and B is $CH_2$; or

G is CH when A is CH=CH and B is CH=CH; or

G is CH=CH when A is $CH_2$ and B is CH=CH;

$R^1$ and $R^2$ may optionally be taken together to form an alicyclic hydrocarbon, heterocyclyl or aromatic hydrocarbon and said optionally formed ring may be optionally substituted with one or more selected from the group consisting of lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidin;

L and Q are independently selected from the group consisting of lower alkylene, lower alkenylene, lower alkynylene, heterocyclyl, cycloalkyl, aromatic hydrocarbon, and $—(CH_2)_m—M—(CH_2)_n—$, $—(CH_2)_k—$, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 8;

m is 0 to 7;

n is 0 to 5;

M is selected from the group consisting of cycloalkyl, heterocyclyl, aromatic hydrocarbon, O, S, SO, $SO_2$, $SO_2NR^5$, $NR^5SO_2$, $NR^5$, $POOR^5$, $PON(R^5)_2$, $POOR^5NR^5$, $NR^5POOR^5$, $C(O)$, $C(O)O$, Se, SeO, $SeO_2$, $C(O)NR^{13}$, and $SiE_2$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

E is lower alkyl or aryl;

L and $R^2$ may be taken together to form a lower alkylidene;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxyl;

with the proviso that when G is $(CH_2)_2$, A is $(CH_2)_2$, B is $CH_2$, and L is $(CH_2)_k$ and k is 0, then $R^1$, $R^2$, $R^3$ and $R^4$ cannot be simultaneously H.

2. A compound as recited in claim 1 or a pharmaceutically acceptable salt thereof, wherein: $R^1$ is selected from the group consisting of hydrogen, lower alkyl, lower alkenyl, lower alkynyl, $OR^5$, $SR^5$, $S(O)R^5$, $S(O)_2R^5$, $C(O)R^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $P(R^5)_3$, $C(O)R^5$, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, amidino, and guanidino, wherein all said substituents may be optionally substituted with one or more selected from the group consisting of halogen, lower alkyl, lower alkenyl, lower alkynyl, cycloalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, $C(O)R^6$, carboalkoxyalkyl, cyano, nitro, amidino, and guanidino, wherein $R^5$ and $R^6$ of $SO_2NR^5R^6$ and $NR^5SO_2R^6$ may be taken together to form a N-containing heterocycle, optionally substituted by one or more selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, and carboxyalkyl;

$R^2$ and L may be taken together to form a 3 to 9 membered alicyclic or heterocyclic ring which may be optionally substituted by one or more of $R^{16}$;

$R^{11}$ is selected from the group consisting of hydrogen, hydroxyl, alkenyl, alkynyl, heterocyclyl, aromatic hydrocarbon, cycloalkyl, dihydropyridyl, alkyl, alkylthiol, alkoxy, amino, and cycloalkoxy, which may be optionally substituted with one or more of amino, carboxyl, carboxamide, thioalkyl, aromatic hydrocarbon, alkyl, alkylaryl, hydroxy, alkoxy, halogen, trifluoromethyl, nitro, cyano, amino, heterocyclyl, alkylheterocycle, and alkylthiol, which may be optionally substituted with one or more of hydroxy, amino, guanidino, iminoalkyl;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

$R^1$ and $R^2$ may optionally be taken together to form an alicyclic hydrocarbon, heterocyclyl or aromatic hydrocarbon and said optionally formed ring may be optionally substituted with one or more selected from the group consisting of lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

L is selected from the group consisting of lower alkylene, lower alkenylene, lower alkynylene, heterocyclyl, cycloalkyl, aromatic hydrocarbon, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 8;

m is 0 to 7;

n is 0 to 5;

M is selected from the group consisting of cycloalkyl, heterocyclyl, aromatic hydrocarbon, O, S, SO, $SO_2$, $SO_2NR^5$, $NR^5SO_2$, $NR^5$, $POOR^5$, $PON(R^5)_2$, $POOR^5NR^5$, $NR^5POOR^5$, $C(O)$, $C(O)O$, Se, SeO, $SeO_2$, $C(O)NR^{13}$, and $SiE_2$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

E is lower alkyl or aryl;

L and $R^2$ may be taken together to form a lower alkylidene;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxyl.

3. A compound recited in claim 2 or a pharmaceutically acceptable salt thereof, wherein: $R^1$ is selected from the group consisting of hydrogen, lower alkyl, lower alkenyl, lower alkynyl, $OR^5$, $SR^5$, $S(O)R^5$, $S(O)_2R^5$, $C(O)R^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $P(R^5)_3$, $C(O)R^5$, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, amidino, and guanidino, wherein all said substituents may be optionally substituted with one or more selected from the group consisting of halogen, lower alkyl, lower alkenyl, lower alkynyl, cycloalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, $C(O)R^6$, carboalkoxyalkyl, cyano, nitro, amidino, and guanidino, wherein $R^5$ and $R^6$ of $SO_2NR^5R^6$ and $NR^5SO_2R^6$ may be taken together to form a N-containing heterocycle, optionally substituted by one or more selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, and carboxyalkyl;

$R^2$ and L may be taken together to form a 3 to 9 membered alicyclic or heterocyclic ring which may be optionally substituted by one or more of $R^{16}$;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O)R$^5$, S(O)$_2$R$^5$, S(O)R$^7$, S(O)$_2$R$^7$, SO$_2$NR$^5$R$^6$, NR$^5$SO$_2$, PO(OR$^5$)(OR$^6$), amidino, and guanidino;

R$^2$ and R$^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, CONR$^5$R$^6$, NR$^5$SO$_2$R$^6$, lower alkyl, lower alkenyl, lower alkynyl, cycloalkyl, heterocyclyl, aromatic hydrocarbon, halogen, cyano, nitro, C(O)R$^6$, carboalkoxyalkyl, OR$^5$, SR$^5$, S(O)R$^5$, S(O)$_2$R$^5$, S(O)R$^7$, S(O)$_2$R$^7$, SO$_2$NR$^5$R$^6$, PO(OR$^5$)(OR$^6$), amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O)R$^5$, S(O)$_2$R$^5$, S(O)R$^7$, S(O)$_2$R$^7$, SO$_2$NR$^5$R$^6$, NR$^5$SO$_2$, PO(OR$^5$)(OR$^6$), amidino, and guanidino;

L is selected from the group consisting of lower alkylene, lower alkenylene, lower alkynylene, heterocyclyl, cycloalkyl, aromatic hydrocarbon, and —(CH$_2$)$_m$—M—(CH$_2$)$_n$—, —(CH$_2$)$_k$—, wherein all said substituents may optionally be substituted by one or more lower alkyl, lower alkenyl, lower alkynyl, C(O)R$^6$, carboalkoxyalkyl, OR$^5$, SR$^5$, S(O)R$^5$, S(O)$_2$R$^5$, SO$_2$NR$^5$R$^6$, NR$^5$SO$_2$R$^6$, C(O)R$^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 8;

m is 0 to 7;

n is 0 to 5;

M is selected from the group consisting of cycloalkyl, heterocyclyl, aromatic hydrocarbon, O, S, SO, SO$_2$, SO$_2$NR$^5$, NR$^5$SO$_2$, NR$^5$, POOR$^5$, PON(R$^5$)$_2$, POOR$^5$NR$^5$, NR$^5$POOR$^5$, C(O), C(O)O, Se, SeO, SeO$_2$, and C(O)NR$^{13}$, wherein R$^{13}$ is selected from the group consisting of hydrogen, lower alkyl, alkaryl, heterocyclyl, COR$^{14}$, and CO$_2$R$^{14}$ wherein R$^{14}$ is lower alkyl or aromatic hydrocarbon;

L and R$^2$ may be taken together to form a lower alkylidene;

R$^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

R$^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

R$^7$ is selected from the group consisting of hydroxy, alkoxy, and aryloxyl.

4. A compound recited in claim 3 or a pharmaceutically acceptable salt thereof, wherein:

R$^1$ is selected from the group consisting of hydrogen, lower alkyl, lower alkenyl, lower alkynyl, OR$^5$, SR$^5$, S(O)R$^5$, S(O)$_2$R$^5$, C(O)R$^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, P(R$^5$)$_3$, C(O)R$^5$, OR$^5$, SR$^5$, S(O)R$^5$, S(O)$_2$R$^5$, S(O)R$^7$, S(O)$_2$R$^7$, SO$_2$NR$^5$R$^6$, NR$^5$SO$_2$R$^6$, CONR$^5$R$^6$, PO(OR$^5$)(OR$^6$), amidino, and guanidino, wherein all said substituents may be optionally substituted with one or more selected from the group consisting of halogen, lower alkyl, lower alkenyl, lower alkynyl, cycloalkyl, OR$^5$, SR$^5$, S(O)R$^5$, S(O)$_2$R$^5$, S(O)R$^7$, S(O)$_2$R$^7$, SO$_2$NR$^5$R$^6$, PO(OR$^5$)(OR$^6$), C(O)R$^6$, carboalkoxyalkyl, cyano, nitro, amidino, and guanidino, wherein R$^5$ and R$^6$ of SO$_2$NR$^5$R$^6$ and NR$^5$SO$_2$R$^6$ may be taken together to form a N-containing heterocycle, optionally substituted by one or more selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, and carboxyalkyl;

R$^2$, R$^3$, R$^4$ are independently selected from the group consisting of hydrogen, lower alkyl, lower alkenyl, lower alkynyl, aromatic hydrocarbon, heterocyclyl, C(O)R$^6$, carboalkoxyalkyl, OR$^5$, SR$^5$, S(O)R$^5$, S(O)$_2$R$^5$, S(O)R$^7$, S(O)$_2$R$^7$, SO$_2$NR$^5$R$^6$, NR$^5$SO$_2$R$^6$, CONR$^5$R$^6$, PO(OR$^5$)(OR$^6$), halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, C(O)R$^6$, carboalkoxyalkyl, CONR$^5$R$^6$, NR$^5$SO$_2$R$^6$, lower alkyl, lower alkenyl, lower alkynyl, cycloalkyl, heterocyclyl, aromatic hydrocarbon, halogen, cyano, nitro, C(O)NR$^5$OR$^5$, OR$^5$, SR$^5$, S(O)R$^5$, S(O)$_2$R$^5$, S(O)R$^7$, S(O)$_2$R$^7$, SO$_2$NR$^5$R$^6$, PO(OR$^5$)(OR$^6$), amidino, and guanidino;

R$^2$ and R$^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, CONR$^5$R$^6$, NR$^5$SO$_2$R$^6$, lower alkyl, lower alkenyl, lower alkynyl, cycloalkyl, heterocyclyl, aromatic hydrocarbon, halogen, cyano, nitro, C(O)R$^6$, carboalkoxyalkyl, OR$^5$, SR$^5$, S(O)R$^5$, S(O)$_2$R$^5$, S(O)

$R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

L is selected from the group consisting of lower alkylene, lower alkenylene, lower alkynylene, heterocyclyl, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 6;

m is 0 to 7;

n is 0 to 5;

M is selected from the group consisting of cycloalkyl, aromatic hydrocarbon, $POOR^5$, $PON(R^5)_2$, $POOR^5NR^5$, $NR^5POOR^5$, $C(O)$, $C(O)O$, Se, SeO, $SeO_2$, and $C(O)NR^{13}$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

L and $R^2$ may be taken together to form a lower alkylidene;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxyl.

5. A compound recited in claim 4 or a pharmaceutically acceptable salt thereof, wherein:

$R^1$ is selected from the group consisting of hydrogen, lower alkyl, lower alkenyl, lower alkynyl, $OR^5$, $SR^5$, $S(O)R^5$, $S(O)_2R^5$, $C(O)R^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^5$, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, amidino, and guanidino, wherein all said substituents may be optionally substituted with one or more selected from the group consisting of halogen, lower alkyl, lower alkenyl, lower alkynyl, cycloalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, $C(O)R^6$, carboalkoxyalkyl, cyano, nitro, amidino, and guanidino, wherein $R^5$ and $R^6$ of $SO_2NR^5R^6$ and $NR^5SO_2R^6$ may be taken together to form a N-containing heterocycle, optionally substituted by one or more selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, and carboxyalkyl;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

L is selected from the group consisting of lower alkylene, lower alkenylene, lower alkynylene, heterocyclyl, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 6;

m is 0 to 7;

n is 0 to 5;

M is selected from the group consisting of cycloalkyl, aromatic hydrocarbon, $POOR^5$, $PON(R^5)_2$, $POOR^5NR^5$, $NR^5POOR^5$, $C(O)$, $C(O)O$, Se, SeO, $SeO_2$, and $C(O)NR^{13}$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxyl.

6. A compound recited in claim 5 or a pharmaceutically acceptable salt thereof, wherein:

$R^1$ is selected from the group consisting of hydrogen, lower alkyl, lower alkenyl, lower alkynyl, $OR^5$, $SR^5$, $S(O)R^5$, $S(O)_2R^5$, $C(O)R^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^5$, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, amidino, and guanidino, wherein all said substituents may be optionally substituted with one or more selected from the group consisting of halogen, lower alkyl;

$R^2$, $R^3$, $R^4$ are independently selected from the group consisting of hydrogen, lower alkyl, lower alkenyl, lower alkynyl, $C(O)R^6$, carboalkoxyalkyl, $OR^5$, $SR^5$, $S(O)R^5$, halogen, nitro, amino, alkylamino, dialkylamino, aminoalkyl, dialkylaminoalkyl, alkylcarbonylamino, carboxyl, carboalkoxy, cyano, aminocarbonylamino, aminocarbonylaminoalkyl, and haloalkyl, wherein all said substituents may be optionally substituted by one or more selected from the group consisting of hydroxy, lower alkoxy, thiol, HS-alkyl-O—, amino, lower alkyl;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

L is selected from the group consisting of lower alkylene, lower alkenylene, lower alkynylene, heterocyclyl, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 6;

m is 0 to 7;

n is 0 to 5;

M is selected from the group consisting of cycloalkyl, aromatic hydrocarbon, $POOR^5$, $PON(R^5)_2$, $POOR^5NR^5$, $NR^5POOR^5$, $C(O)$, $C(O)O$, Se, SeO, and $SeO_2$;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, and alkoxy.

7. A compound recited in claim 6 or a pharmaceutically acceptable salt thereof, wherein:

$R^1$ is selected from the group consisting of hydrogen, lower alkyl, lower alkenyl, lower alkynyl, $OR^5$, $SR^5$, $S(O)R^5$, $S(O)_2R^5$, $C(O)R^6$, carboalkoxyalkyl, heterocyclyl, aromatic hydrocarbon and cycloalkyl, all of which may be optionally substituted by one or more of the groups selected from lower alkyl, lower alkenyl, lower alkynyl, cycloalkyl, heterocyclyl, aryl, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^5$, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, amidino, and guanidino, wherein all said substituents may be optionally substituted with one or more selected from the group consisting of halogen, lower alkyl;

$R^2$, $R^3$, $R^4$ are independently selected from the group consisting of hydrogen, lower alkyl, $C(O)R^6$, carboalkoxyalkyl, $OR^5$, $SR^5$, $S(O)R^5$, halogen, amino, alkylamino, aminoalkyl, cyano, and haloalkyl;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

L is selected from the group consisting of lower alkylene, lower alkenylene, lower alkynylene, heterocyclyl, and —(CH$_2$)$_m$—M—(CH$_2$)$_n$—, —(CH$_2$)$_k$—, wherein all said substituents may optionally be substituted by one or more lower alkyl, lower alkenyl, lower alkynyl, C(O)R$^6$, carboalkoxyalkyl, OR$^5$, SR$^5$, S(O)R$^5$, heterocyclyl, halogen, nitro, cyano, and haloalkyl;

k is 0 to 6;

m is 0 to 7;

n is 0 to 5;

M is selected from the group consisting of cycloalkyl, aromatic hydrocarbon, POOR$^5$, PON(R$^5$)$_2$, POOR$^5$NR$^5$, NR$^5$POOR$^5$, C(O), C(O)O, Se, SeO, and SeO$_2$;

R$^5$ is selected from the group consisting of hydrogen, halogen lower alkyl, and aromatic hydrocarbon, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

R$^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

R$^7$ is selected from the group consisting of hydroxy, and alkoxy.

8. A compound as recited in claim 1 or a pharmaceutically acceptable salt thereof, wherein, R$^1$ may be

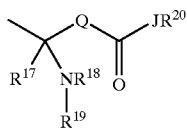

wherein J is selected from the group consisting of O, S and NR;

R is selected from the group consisting of hydrogen, lower alkyl, lower alkenyl, lower alkynyl, cycloalkyl, cycloalkenyl, heterocycle, aromatic hydrocarbon, alkylaryl, alkylheterocycle, all of which may be optionally substituted by one or more of alkyl, hydroxy, alkoxy, halogen, haloalkyl, cyano, amino, and nitro;

NR and R$^{20}$ may optionally form a heterocycle;

R$^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, C(O)R$^6$, carboalkoxyalkyl, CONR$^5$R$^6$, S(O)R$^5$, S(O)$_2$R$^5$, SO$_2$NR$^5$R$^6$, NR$^5$SO$_2$R$^6$, PO(OR$^5$)(OR$^6$), amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O)R$^8$, S(O)$_2$R$^8$, S(O)R$^{10}$, S(O)$_2$R$^{10}$, SO$_2$NR$^8$R$^9$, NR$^8$SO$_2$, PO(OR$^8$)(OR$^9$), amidino, and guanidino;

R$^{17}$ is selected from the group consisting of hydrogen, lower alkyl, hydroxyalkyl, alkoxyalkyl, haloalkyl, cycloalkyl, heterocycle, aromatic hydrocarbon, alkylaryl, and alkylheterocycle, all except hydrogen may be optionally substituted by one or more of alkyl, hydroxy, alkoxy, thiol, alkylthiol, halogen, haloalkyl, carboxyl, cyano, amino, and nitro;

R$^{18}$ is selected from the group consisting of hydrogen, hydroxyl, R$^{12}$, S(O)R$^{11}$, SO$_2$R$^{11}$, CH$_2$OC(O)—R$^{11}$, and C(O)—R$^{11}$;

R$^{18}$ and R$^{20}$ may be taken together to form a 5- or 6-membered heterocyclic ring containing two or more heteroatoms which may be optionally substituted by one or more of R$^{16}$;

R$^2$ and L may be taken together to form a 3 to 9 membered alicyclic or heterocyclic ring which may be optionally substituted by one or more of R$^{16}$;

R$^2$ and R$^{17}$ may be taken together to form a 4 to 9 membered alicyclic or heterocyclic ring which may be optionally substituted by one or more of R$^{16}$;

R$^2$ and R$^{18}$ may be taken together to form a 6 to 9 membered heterocyclic ring which may be optionally substituted by one or more of R$^{16}$;

L and R$^{17}$ may be taken together to form a 3 to 9 membered alicyclic or heterocyclic ring which may be optionally substituted by one or more of R$^{16}$;

L and R$^{18}$ may be taken together to form a 4 to 9 membered alicyclic or heterocyclic ring which may be optionally substituted by one or more of R$^{16}$;

R$^{17}$ and R$^{18}$ and may be taken together to form a 4 to 9 membered heterocyclic ring which may be optionally substituted by one or more of R$^{16}$;

R$^{17}$ and Q may be taken together to form a 3 to 9 membered alicyclic or heterocyclic ring which may be optionally substituted by one or more of R$^{16}$;

R$^{18}$ and Q may be taken together to form a 4 to 9 membered heterocyclic ring which may be optionally by one or more of R$^{16}$;

R$^{17}$ and R$^{20}$ and may be taken together to form a 5 to 9 membered heterocyclic ring which may be optionally substituted by one or more of R$^{16}$;

R$^{19}$ is hydrogen, R$^{11}$, or C(O)—R$^{11}$;

R$^{11}$ is selected from the group consisting of hydrogen, hydroxyl, alkenyl, alkynyl, heterocyclyl, aromatic hydrocarbon, cycloalkyl, dihydropyridyl, alkyl, alkylthiol, alkoxy, amino, and cycloalkoxy, which may be optionally substituted with one or more of amino, carboxyl, carboxamide, thioalkyl, aromatic hydrocarbon, alkyl, alkylaryl, hydroxy, alkoxy, halogen, trifluoromethyl, nitro, cyano, amino, heterocyclyl, alkylheterocycle, and alkylthiol, which may be optionally substituted with one or more of hydroxy, amino, guanidino, iminoalkyl;

R$^{12}$ is selected from the group consisting of hydrogen, alkyl, alkenyl, alkynyl, cycloalkyl, heterocycle, and aromatic hydrocarbon, all may be optionally substituted by one or more alkyl, hydroxy, alkoxy, halogen, trifluoromethyl, nitro, cyano, or amino groups;

R$^{20}$ is selected from the group consisting of hydrogen, lower alkyl, lower alkenyl, lower alkynyl, cycloalkyl, cycloalkenyl, aromatic hydrocarbon, heterocycle, alkylaryl, and alkylheterocycle, which may be optionally substituted by one or more of halogen, haloalkyl, cyano, nitro, —CO$_2$R, and —COR;

R$^{20}$ may also be selected from the group consisting of alkylhydroxy, alkylpolyhydroxy, alkyl(poly) oxyalkylcarbonyl, CH$_2$C(=O)OR$^{12}$, CH$_2$C(=O) NHR$^{12}$, CH$_2$OC(=O)R$^{12}$, and CH$_2$OC(=O)VR$^{12}$, wherein the CH$_2$ may be optionally substituted by one or more of lower alkyl, cycloalkyl, heterocycle, aromatic hydrocarbon, amidino, guanidino, CO$_2$H, amino, hydroxy, thiol, halogen, haloalkyl, cyano, and nitro;

V is selected from the group consisting of O, S, CH$_2$, CHR$^{12}$, C(R$^{12}$)$_2$, NH, and NR$_{12}$;

R$^2$, R$^3$, R$^4$ are independently selected from the group consisting of hydrogen, lower alkyl, lower alkenyl, lower alkynyl, aromatic hydrocarbon, heterocyclyl, C(O)R$^6$, carboalkoxyalkyl, OR$^5$, SR$^5$, S(O)R$^5$, S(O)$_2$R$^5$, S(O)R$^7$, S(O)$_2$R$^7$, SO$_2$NR$^5$R$^6$, NR$^5$SO$_2$R$^6$, CONR$^5$R$^6$, PO(OR$^5$)(OR$^6$), halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, C(O)R$^6$, carboalkoxyalkyl, CONR$^5$R$^6$, NR$^5$SO$_2$R$^6$, lower alkyl, lower alkenyl, lower alkynyl, cycloalkyl, heterocyclyl, aromatic hydrocarbon, halogen, cyano, nitro, C(O)NR$^5$OR$^5$, OR$^5$, SR$^5$, S(O) R$^5$, S(O)$_2$R$^5$, S(O)R$^7$, S(O)$_2$R$^7$, SO$_2$NR$^5$R$^6$, PO(OR$^5$) (OR$^6$), amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O)R$^5$, S(O)$_2$R$^5$, S(O)R$^7$, S(O)$_2$R$^7$, SO$_2$NR$^5$R$^6$, NR$^5$SO$_2$, PO(OR$^5$)(OR$^6$), amidino, and guanidino;

R$^2$ and R$^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, CONR$^5$R$^6$, NR$^5$SO$_2$R$^6$, lower alkyl, lower alkenyl, lower alkynyl, cycloalkyl, heterocyclyl, aromatic hydrocarbon, halogen, cyano, nitro, C(O)R$^6$, carboalkoxyalkyl, OR$^5$, SR$^5$, S(O)R$^5$, S(O)$_2$R$^5$, S(O) R$^7$, S(O)$_2$R$^7$, SO$_2$NR$^5$R$^6$, PO(OR$^5$)(OR$^6$), amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O) R$^5$, S(O)$_2$R$^5$, S(O)R$^7$, S(O)$_2$R$^7$, SO$_2$NR$^5$R$^6$, NR$^5$SO$_2$, PO(OR$^5$)OR$^6$), amidino, and guanidino;

L and Q are independently selected from the group consisting of lower alkylene, lower alkenylene, lower alkynylene, heterocyclyl, cycloalkyl, aromatic hydrocarbon, and —(CH$_2$)$_m$—M—(CH$_2$)$_n$—, —(CH$_2$)$_k$—, wherein all said substituents may optionally be substituted by one or more lower alkyl, lower alkenyl, lower alkynyl, C(O)R$^6$, carboalkoxyalkyl, OR$^5$, SR$^5$, S(O)R$^5$, S(O)$_2$R$^5$, SO$_2$NR$^5$R$^6$, NR$^5$SO$_2$R$^6$, C(O)R$^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 8;

m is 0 to 7;

n is 0 to 5;

M is selected from the group consisting of cycloalkyl, heterocyclyl, aromatic hydrocarbon, O, S, SO, SO$_2$, SO$_2$NR$^5$, NR$^5$SO$_2$, NR$^5$, POOR$^5$, PON(R$^5$)$_2$, POOR$^5$NR$^5$, NR$^5$POOR$^5$, C(O), C(O)O, Se, SeO, SeO$_2$, C(O)NR$^{13}$, and SiE$_2$, wherein R$^{13}$ is selected from the group consisting of hydrogen, lower alkyl, alkaryl, heterocyclyl, COR$^{14}$, and CO$_2$R$^{14}$ wherein R$^{14}$ is lower alkyl or aromatic hydrocarbon;

E is lower alkyl or aryl;

L and R$^2$ may be taken together to form a lower alkylidene;

R$^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

R$^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

R$^7$ is selected from the group consisting of hydroxy, alkoxy, and aryloxyl.

9. A compound as recited in claim 8 or a pharmaceutically acceptable salt thereof, wherein:

R$^1$ is

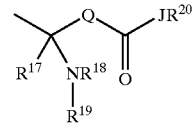

wherein J is selected from the group consisting of O, S and NR;

R is selected from the group consisting of hydrogen, lower alkyl, lower alkenyl, lower alkynyl, cycloalkyl, cycloalkenyl, heterocycle, aromatic hydrocarbon, alkylaryl, alkylheterocycle, all of which may be optionally substituted by one or more of alkyl, hydroxy, alkoxy, halogen, haloalkyl, cyano, amino, and nitro;

NR and R$^{20}$ may optionally form a heterocycle;

R$^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $S(O)R^5$, $S(O)_2R^5$, $SO_2NR^5R^6$, $NR^5SO_2R^6$, $PO(OR^5)(OR^6)$, amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^8$, $S(O)_2R^8$, $S(O)R^{10}$, $S(O)_2R^{10}$, $SO_2NR^8R^9$, $NR^8SO_2$, $PO(OR^8)(OR^9)$, amidino, and guanidino;

$R^{17}$ is selected from the group consisting of hydrogen, lower alkyl, hydroxyalkyl, alkoxyalkyl, haloalkyl, cycloalkyl, heterocycle, aromatic hydrocarbon, alkylaryl, and alkylheterocycle, all except hydrogen may be optionally substituted by one or more of alkyl, hydroxy, alkoxy, thiol, alkylthiol, halogen, haloalkyl, carboxyl, cyano, amino, and nitro;

$R^{18}$ is selected from the group consisting of hydrogen, hydroxyl, and $R^{12}$;

$R^{17}$ and Q may be taken together to form a 3 to 9 membered alicyclic or heterocyclic ring which may be optionally substituted by one or more of $R^{16}$;

$R^{18}$ and Q may be taken together to form a 4 to 9 membered heterocyclic ring which may be optionally by one or more of $R^{16}$;

$R^{19}$ is hydrogen;

$R^{12}$ is selected from the group consisting of hydrogen, alkyl, alkenyl, alkynyl, cycloalkyl, heterocycle, and aromatic hydrocarbon, all may be optionally substituted by one or more alkyl, hydroxy, alkoxy, halogen, trifluoromethyl, nitro, cyano, or amino groups;

$R^{20}$ is selected from the group consisting of hydrogen, lower alkyl, lower alkenyl, lower alkynyl, cycloalkyl, cycloalkenyl, aromatic hydrocarbon, heterocycle, alkylaryl, and alkylheterocycle, which may be optionally substituted by one or more of halogen, haloalkyl, cyano, nitro, —$CO_2R$, and —COR;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$ $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

L and Q are independently selected from the group consisting of lower alkylene, lower alkenylene, lower alkynylene, heterocyclyl, cycloalkyl, aromatic hydrocarbon, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 8;

m is 0 to 7;

n is 0 to 5;

M is selected from the group consisting of cycloalkyl, heterocyclyl, aromatic hydrocarbon, O, S, SO, $SO_2$, $SO_2NR^5$, $NR^5SO_2$, $NR^5$, $POOR^5$, $PON(R^5)_2$, $POOR^5NR^5$, $NR^5POOR^5$, C(O), C(O)O, Se, SeO, $SeO_2$, and $C(O)NR^{13}$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxyl.

10. A compound as recited in claim 9 or a pharmaceutically acceptable salt thereof, wherein:

$R^1$ is

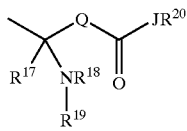

wherein J is selected from the group consisting of O, S and NR;

R is selected from the group consisting of hydrogen, lower alkyl, lower alkenyl, lower alkynyl, cycloalkyl, cycloalkenyl, heterocycle, aromatic hydrocarbon, alkylaryl, alkylheterocycle;

NR and $R^{20}$ may optionally form a heterocycle;

$R^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $S(O)R^5$, $S(O)_2R^5$, $SO_2NR^5R^6$, $NR^5SO_2R^6$, $PO(OR^5)(OR^6)$, amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^8$, $S(O)_2R^8$, $S(O)R^{10}$, $S(O)_2R^{10}$, $SO_2NR^8R^9$, $NR^8SO_2$, $PO(OR^8)(OR^9)$, amidino, and guanidino;

$R^{17}$ is selected from the group consisting of hydrogen, lower alkyl, hydroxyalkyl, alkoxyalkyl, haloalkyl, cycloalkyl, heterocycle, and alkylheterocycle, all except hydrogen may be optionally substituted by one or more of alkyl, hydroxy, alkoxy, thiol, alkylthiol, halogen, haloalkyl, carboxyl, cyano, amino, and nitro;

$R^{18}$ is selected from the group consisting of hydrogen, and hydroxyl;

$R^{18}$ and Q may be taken together to form a 4 to 9 membered heterocyclic ring which may be optionally by one or more of $R^{16}$;

$R^{19}$ is hydrogen;

$R^{20}$ is selected from the group consisting of hydrogen, lower alkyl, lower alkenyl, lower alkynyl, cycloalkyl, cycloalkenyl, aromatic hydrocarbon, heterocycle, alkylaryl, and alkylheterocycle, which may be optionally substituted by one or more of halogen, haloalkyl, cyano, nitro, —$CO_2R$, and —COR;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino, wherein all said substitutions may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^5$, $S(O)_2R^5$, $S(O)R^7$, $S(O)_2R^7$, $SO_2NR^5R^6$, $NR^5SO_2$, $PO(OR^5)(OR^6)$, amidino, and guanidino;

Q is —$(CH_2)_k$—, wherein k is 0;

L is selected from the group consisting of lower alkylene, lower alkenylene, lower alkynylene, heterocyclyl, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 6;

m is 0 to 5;

n is 0 to 3;

M is selected from the group consisting of cycloalkyl, heterocyclyl, aromatic hydrocarbon, O, S, SO, $SO_2$, $SO_2NR^5$, $NR^5SO_2$, $NR^5$, $POOR^5$, $PON(R^5)_2$, $POOR^5NR^5$, $NR^5POOR^5$, $C(O)$, $C(O)O$, Se, SeO, $SeO_2$, and $C(O)NR^{13}$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxy.

11. A compound as recited in claim 10 or a pharmaceutically acceptable salt thereof, wherein:

$R^1$ is

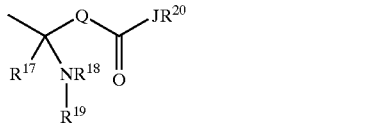

wherein J is O;

$R^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $S(O)R^5$, $S(O)_2R^5$, $SO_2NR^5R^6$, $NR^5SO_2R^6$, $PO(OR^5)(OR^6)$, amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, $C(O)R^6$, carboalkoxyalkyl, $S(O)R^8$, $S(O)_2R^8$, $S(O)R^{10}$, $S(O)_2R^{10}$, $SO_2NR^8R^9$, $NR^8SO_2$, $PO(OR^8)(OR^9)$, amidino, and guanidino;

$R^{17}$ is selected from the group consisting of hydrogen, lower alkyl, hydroxyalkyl, alkoxyalkyl, haloalkyl, cycloalkyl, and heterocycle, all except hydrogen may be optionally substituted by one or more of alkyl, hydroxy, alkoxy, thiol, alkylthiol, halogen, haloalkyl, carboxyl, cyano, amino, and nitro;

$R^{18}$ is hydrogen;

$R^{19}$ is hydrogen;

$R^{20}$ is selected from the group consisting of hydrogen, and lower alkyl;

$R^2$, $R^3$, $R^4$ are independently selected from the group consisting of hydrogen, lower alkyl, lower alkenyl, lower alkynyl, aromatic hydrocarbon, heterocyclyl, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $NR^5SO_2R^6$, $CONR^5R^6$, $PO(OR^5)(OR^6)$, halogen, nitro, amino, alkylamino, dialkylamino, aminoalkyl, dialkylaminoalkyl, arylamino, alkylaminoaryl, alkylcarbonylamino, carboxyl, carboalkoxy, carboaryloxy, carboarylalkyloxy, cyano, aminocarbonylalkoxy, aminocarbonylamino, aminocarbonylaminoalkyl, carboxyaldehyde, and haloalkyl, wherein all said substituents may be optionally substituted by one or more selected from the group consisting of hydroxy, lower alkoxy, aryloxy, thiol, HS-alkyl-O—, amino, alkylamino, dialkylamino, aminoalkyl, dialkylaminoalkyl, arylamino, aminoaryl, alkylaminoaryl, alkylcarbonylamino, carboxy, carboxyalkyl, $C(O)R^6$, carboalkoxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)NR^5OR^5$, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

$R^2$ and $R^3$ may optionally be taken together to form an alicyclic hydrocarbon, heterocyclyl or aromatic hydrocarbon and said optionally formed ring may be optionally substituted with one or more selected from the group consisting of, amino, alkylamino, dialkylamino, aminoalkyl, dialkylaminoalkyl, arylamino, aminoaryl, alkylaminoaryl, alkylcarbonylamino, carboxy, carboxyalkyl, $CONR^5R^6$, $NR^5SO_2R^6$, lower alkyl, lower alkenyl, lower alkynyl, cycloalkyl, heterocyclyl, aromatic hydrocarbon, halogen, cyano, nitro, $C(O)R^6$, carboalkoxyalkyl, $OR^5$, $SR^5$, $S(O)R^5$, $S(O)_2R^5$, $S(O)R^7$, $S(O)_2R^7$, $SO_2NR^5R^6$, $PO(OR^5)(OR^6)$, amidino, and guanidino;

Q is —$(CH_2)_k$—, wherein k is 0;

L is selected from the group consisting of lower alkylene, lower alkenylene, lower alkynylene, heterocyclyl, and —$(CH_2)_m$—M—$(CH_2)_n$—, —$(CH_2)_k$—, wherein all said substituents may optionally be substituted by one or more lower alkyl, lower alkenyl, lower alkynyl, $C(O)R^6$, carboalkoxyalkyl, $OR^5$, $SR^5$, $S(O)R^5$, $S(O)_2R^5$, $SO_2NR^5R^6$, $NR^5SO_2R^6$, $C(O)R^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 6;

m is 0 to 5;

n is 0 to 3;

M is selected from the group consisting of cycloalkyl, heterocyclyl, aromatic hydrocarbon, O, S, SO, $SO_2$, $SO_2NR^5$, $NR^5SO_2$, $NR^5$, $C(O)$, $C(O)O$, and $C(O)NR^{13}$, wherein $R^{13}$ is selected from the group consisting of hydrogen, lower alkyl, alkaryl, heterocyclyl, $COR^{14}$, and $CO_2R^{14}$ wherein $R^{14}$ is lower alkyl or aromatic hydrocarbon;

$R^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^6$ is selected from the group consisting of hydrogen, lower alkyl, aromatic hydrocarbon and alkylaryl wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates;

$R^7$ is selected from the group consisting of hydroxy, alkoxy, and aryloxy.

12. A compound as recited in claim 11 or a pharmaceutically acceptable salt thereof, wherein:

$R^1$ is

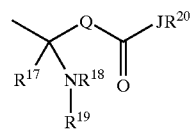

wherein J is O;

$R^{16}$ is selected from the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, amino, alkylamino, dialkylamino, aminoalkyl, dialkylaminoalkyl, arylamino, aminoaryl, alkylaminoaryl, alkylcarbonylamino, carboxy, carboxyalkyl, C(O)R$^6$, carboalkoxyalkyl, CONR$^5$R$^6$, S(O)R$^5$, S(O)$_2$R$^5$, SO$_2$NR$^5$R$^6$, NR$^5$SO$_2$R$^6$, PO(OR$^5$)(OR$^6$), amidino, and guanidino, wherein all said substituents may be optionally substituted with one or more of the group consisting of lower alkyl, lower alkenyl, lower alkynyl, cycloalkyl, heterocyclyl, aromatic hydrocarbon, hydroxy, lower alkoxy, aryloxy, thiol, HS-alkyl-O—, halogen, cyano, nitro, C(O)R$^6$, carboalkoxyalkyl, S(O)R$^8$, S(O)$_2$R$^8$, S(O)R$^{10}$, S(O)$_2$R$^{10}$, SO$_2$NR$^8$R$^9$, NR$^8$SO$_2$, PO(OR$^8$)(OR$^9$), amidino, and guanidino;

R$^{17}$ is selected from the group consisting of hydrogen, lower alkyl, hydroxyalkyl, alkoxyalkyl, haloalkyl, cycloalkyl, and heterocycle, all except hydrogen may be optionally substituted by one or more of alkyl, hydroxy, alkoxy, thiol, alkylthiol, halogen, haloalkyl, carboxyl, cyano, amino, and nitro;

R$^{18}$ is hydrogen;

R$^{19}$ is hydrogen;

R$^{20}$ is selected from the group consisting of hydrogen, and lower alkyl;

R$^2$, R$^3$, R$^4$ are independently selected from the group consisting of hydrogen, lower alkyl, lower alkenyl, lower alkynyl, C(O)R$^6$, carboalkoxyalkyl, OR$^5$, SR$^5$, halogen, nitro, amino, alkylamino, dialkylamino, aminoalkyl, dialkylaminoalkyl, alkylcarbonylamino, carboxyl, carboalkoxy, cyano, aminocarbonylamino, aminocarbonylaminoalkyl, and haloalkyl, wherein all said substituents may optionally be substituted by one or more selected from the group consisting of hydroxy, lower alkoxy, thiol, HS-alkyl-O—, amino;

Q is —(CH$_2$)$_k$—, wherein k is 0;

L is selected from the group consisting of lower alkylene, lower alkenylene, lower alkynylene, heterocyclyl, and —(CH$_2$)$_m$—M—(CH$_2$)$_n$—, —(CH$_2$)$_k$—, wherein all said substituents may optionally be substituted by one or more lower alkyl, lower alkenyl, lower alkynyl, C(O)R$^6$, carboalkoxyalkyl, OR$^5$, SR$^5$, S(O)R$^5$, S(O)$_2$R$^5$, heterocyclyl, halogen, nitro, cyano, haloalkyl, cycloalkyl, heterocyclyl, aromatic hydrocarbon, lactonyl, lactamyl, amidino, isourea, isothiourea, guanidino, and substituted guanidino;

k is 0 to 6;

m is 0 to 5;

n is 0 to 3;

M is selected from the group consisting of cycloalkyl, heterocyclyl, aromatic hydrocarbon, O, S, SO, SO$_2$, SO$_2$NR$^5$, NR$^5$SO$_2$, NR$^5$, C(O), and C(O)O;

R$^5$ is selected from the group consisting of hydrogen, halogen lower alkyl, aromatic hydrocarbon, and alkylaryl, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates.

13. A compound as recited in claim 12 or a pharmaceutically acceptable salt thereof, wherein:

R$^1$ is

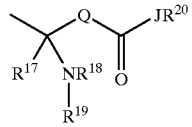

wherein J is O;

R$^{17}$ is selected from the group consisting of hydrogen, lower alkyl, and hydroxyalkyl;

R$^{18}$ is hydrogen;

R$^{19}$ is hydrogen;

R$^{20}$ is selected from the group consisting of hydrogen, and lower alkyl;

R$^2$, R$^3$, R$^4$ are independently selected from the group consisting of hydrogen, lower alkyl, C(O)R$^6$, carboalkoxyalkyl, OR$^5$, SR$^5$, halogen, amino, alkylamino, and aminoalkyl;

Q is —(CH$_2$)$_k$—, wherein k is 0;

L is selected from the group consisting of lower alkylene, lower alkenylene, lower alkynylene, heterocyclyl, and —(CH$_2$)$_m$—M—(CH$_2$)$_n$—, —(CH$_2$)$_k$—, wherein all said substituents may optionally be substituted by one or more lower alkyl, lower alkenyl, lower alkynyl, C(O)R$^6$, carboalkoxyalkyl, OR$^5$, SR$^5$, S(O)R$^5$, S(O)$_2$R$^5$, heterocyclyl, halogen, cyano, and haloalkyl;

k is 0 to 6;

m is 0 to 5;

n is 0 to 3;

M is selected from the group consisting of heterocyclyl, O, S, SO, SO$_2$, SO$_2$NR$^5$, NR$^5$SO$_2$, and NR$^5$;

R$^5$ is selected from the group consisting of hydrogen, halogen lower alkyl, and aromatic hydrocarbon, wherein all said substituents may be optionally substituted by one or more carboalkoxy, thiol, amino, hydroxyl, carboxyl, lower alkyl, lower alkenyl, lower alkynyl, halo, cyano, nitro, carboxyalkyl, carboxamides, phosphonates, and sulfonates.

14. A compound selected from the group consisting of:

1,1-dimethylethyl[2-(6,7,8,9-tetrahydro-3-oxo-3H,5H-[1,2,4]oxadiazolo[4,3-a]azepin-5-yl)ethyl]carbamate;

5-(2-aminoethyl)-6,7,8,9-tetrahydro-3H,5H-[1,2,4]oxadiazolo[4,3-a]azepin-3-one, mono(trifluoroacetate);

Methyl 6,7,8,9-tetrahydro-3-oxo-3H,5H-[1,2,4]oxadiazolo[4,3-a]azepine-5-carboxylate;

6,7,8,9-tetrahydro-5-(hydroxymethyl)-3H,5H-[1,2,4]oxadiazolo[4,3-a]azepin-3-one;

6,7,8,9-tetrahydro-5-(2-propenyl)-3H,5H-[1,2,4]oxadiazolo[4,3-a]azepin-3-one;

5-ethyl-6,7,8,9-tetrahydro-3H,5H-[1,2,4]oxadiazolo[4,3-a]azepin-3-one;

6,7,8,9-tetrahydro-3-oxo-3H,5H-[1,2,4]oxadiazolo[4,3-a]azepine-5-acetaldehyde;

6,7,8,9-tetrahydro-5-(2-hydroxyethyl)-3H,5H-[1,2,4]oxadiazolo[4,3-a]azepin-3-one;

Ethyl 4,5-dihydro-5-[(6,7,8,9-tetrahydro-3-oxo-3H,5H-[1,2,4]oxadiazolo[4,3-a]azepin-5-yl)methyl]-3-isoxazolecarboxylate;

6,7,8,9-tetrahydro-5-(3-hydroxypropyl)-3H,5H-[1,2,4]oxadiazolo[4,3-a]azepin-3-one;

5-(3-bromopropyl)-6,7,8,9-tetrahydro-3H,5H-[1,2,4] oxadiazolo[4,3-a]azepin-3-one;
9-ethyl-6,7,8,9-tetrahydro-3H,5H-[1,2,4]oxadiazolo[4,3-a] azepin-3-one;
5-(bromomethyl)-6,7,8,9-tetrahydro-3H,5H-[1,2,4] oxadiazolo[4,3-a]azepin-3-one;
6,7,8,9-tetrahydro-5-(2-nitroethyl)-3H,5H-[1,2,4] oxadiazolo[4,3-a]azepin-3-one;
4,5-dihydro-5-[(6,7,8,9-tetrahydro-3-oxo-3H,5H-[1,2,4] oxadiazolo[4,3-a]azepin-5-yl)methyl]-3-isoxazolecarboxylic acid;
5-(3-butenyl)-6,7,8,9-tetrahydro-3H,5H-[1,2,4]oxadiazolo [4,3-a]azepin-3-one;
6,7,8,9-tetrahydro-3-oxo-3H,5H-[1,2,4]oxadiazolo[4,3-a] azepine-5-propanal;
5-(2-bromoethyl)-6,7,8,9-tetrahydro-3H,5H-[1,2,4] oxadiazolo[4,3-a]azepin-3-one;
Bis(1,1-dimethylethyl)4-nitro-4-[(6,7,8,9-tetrahydro-3-oxo-3H,5H-[1,2,4]oxadiazolo[4,3-a]azepin-5-yl)methyl] heptanedioate;
8,9-dihydro-5-[(phenylmethoxy)methyl]-3H,5H-[1,2,4] oxadiazolo[4,3-a]azepin-3-one;
5-ethyl-6,7,8,9-tetrahydro-3H,5H-[1,2,4]oxadiazolo[4,3-a] azepine-3-thione;
6-ethyl-7,8,9,10-tetrahydro-6H-[1,2,4]oxadiazino[4,3-a] azepine-3,4-dione;
5-[(4-amino-1H-imidazol-2-yl)methyl]-6,7,8,9-tetrahydro-3H,5H-[1,2,4]oxadiazolo[4,3-a]azepin-3-one, monohydrochloride;
5-(ethoxymethyl)-6,7,8,9-tetrahydro-3H,5H-[1,2,4] oxadiazolo[4,3-a]azepin-3-one;
5-[(ethylthio)methyl]-6,7,8,9-tetrahydro-3H,5H-[1,2,4] oxadiazolo[4,3-a]azepin-3-one;
5-[(ethylsulfinyl)methyl]-6,7,8,9-tetrahydro-3H,5H-[1,2,4] oxadiazolo[4,3-a]azepin-3-one;
5-[(ethylsulfonyl)methyl]-6,7,8,9-tetrahydro-3H,5H-[1,2,4] oxadiazolo[4,3-a]azepin-3-one;
6,7,8,9-tetrahydro-5-(1-oxo-3-butenyl)-3H,5H-[1,2,4] oxadiazolo[4,3-a]azepin-3-one;
N-[2-(6,7,8,9-tetrahydro-3-oxo-3H,5H-[1,2,4]oxadiazolo[4, 3-a]azepin-5-yl]ethyl]methanesulfonamide;
5-(2-aminomethyl)-6,7,8,9-tetrahydro-3H,5H-[1,2,4] oxadiazolo-[4,3-a]azepin-3-one;
N-[2-(6,7,8,9-tetrahydro-3-oxo-3H,5H-[1,2,4]oxadiazolo-[4,3-a]azepin-5-yl]methyl]methanesulfonamide;
N-Methyl-N-[2-(6,7,8,9-tetrahydro-3-oxo-3H,5H-[1,2,4]-oxadiazolo-[4,3-a]azepin-5-yl]methyl] methanesulfonamide;
6,7,8,9-tetrahydro-3-oxo-3H,5H-[1,2,4]oxadiazolo[4,3-a] azepine-5-carboxylic acid;
6,7,8,9-tetrahydro-3-oxo-3H,5H-[1,2,4]oxadiazolo[4,3-a] azepine-5-carboxylic acid chloride;
6,7,8,9-tetrahydro-3-oxo-3H,5H-[1,2,4]oxadiazolo[4,3-a] azepine-5-methoxymethycarboxylic acid amide;
(2S,3Z)-2-amino-5-(6,7,8,9-tetrahydro-3-oxo-3H,5H-[1,2, 4]oxadiazolo[4,3-a]azepin-5-yl)-3-pentenoic acid;
N-[(1,1-dimethylethoxy)carbonyl]-3-[[2-(6,7,8,9-tetrahydro-3-oxo-3H,5H-[1,2,4]oxadiazolo[4,3-a]azepin-5-yl]ethyl]amino]-L-alanine;
N-[(1,1-dimethylethoxy)carbonyl]-3-[ethyl[2-(6,7,8,9-tetrahydro-3-oxo-3H,5H-[1,2,4]oxadiazolo[4,3-a]azepin-5-yl]ethyl]amino]-L-alanine;
Phenylmethyl(2S,4Z)-2-[[(1,1-dimethylethoxy)carbonyl] amino]-5-(6,7,8,9-tetrahydro-3-oxo-3H,5H-[1,2,4] oxadiazolo[4,3-a]azepin-5-yl)-4-pentenoate;
a-amino-5-fluoro-6,7,8,9-tetrahydro-3-oxo-3H,5H-[1,2,4] oxadiazolo[4,3-a]azepine-5-hexanoic acid;
N-[(1,1-dimethylethoxy)carbonyl]-S-[(6,7,8,9-tetrahydro-3-oxo-3H,5H-[1,2,4]oxadiazolo[4,3-a]azepin-5-yl)methyl]-L-cysteine;
S-[(6,7,8,9-tetrahydro-3-oxo-3H,5H-[1,2,4]oxadiazolo[4,3-a]azepin-5-yl)methyl]-L-cysteine, monohydrochloride;
3-[[(6,7,8,9-tetrahydro-3-oxo-3H,5H-[1,2,4]oxadiazolo[4, 3-a]azepin-5-yl)methyl]sulfinyl]-L-alanine, monohydrochloride;
3-[[(6,7,8,9-tetrahydro-3-oxo-3H,5H-[1,2,4]oxadiazolo[4, 3-a]azepin-5-yl)methyl]sulfonyl]-L-alanine, monohydrochloride;
Methyl a-(acetylamino)-6,7,8,9-tetrahydro-g,3-dioxo-3H, 5H-[1,2,4]oxadiazolo[4,3-a]azepine-5-pentanoate;
Methyl a-(acetylamino)-g,g-difluoro-6,7,8,9-tetrahydro-3-oxo-3H,5H-[1,2,4]oxadiazolo[4,3-a]azepine-5-pentanoate;
Methyl a-(acetylamino)-6,7,8,9-tetrahydro-g-nitro-3-oxo-3H,5H-[1,2,4]oxadiazolo[4,3-a]azepine-5-pentanoate;
Methyl a-(acetylamino)-6,7,8,9-tetrahydro-g-methylene-3-oxo-3H,5H-[1,2,4]oxadiazolo[4,3-a]azepine-5-pentanoate;
N-[(1,1-dimethylethoxy)carbonyl]-3-[[(6,7,8,9-tetrahydro-3-oxo-3H,5H-[1,2,4]oxadiazolo[4,3-a]azepin-5-yl) methyl]amino]-L-alanine;
Methyl(2S,4Z)-2-[[(1,1-dimethylethoxy)carbonyl]amino]-6-(6,7,8,9-tetrahydro-3-oxo-3H,5H-[1,2,4]oxadiazolo[4, 3-a]azepin-5-yl)-4-hexenoate;
(3Z)-2-amino-6-(6,7,8,9-tetrahydro-3-oxo-3H,5H-[1,2,4] oxadiazolo[4,3-a]azepin-5-yl)-4-hexenoic acid;
5-amino-2-[(6,7,8,9-tetrahydro-3-oxo-3H,5H-[1,2,4] oxadiazolo[4,3-a]azepin-5-yl)methyl]-1H-imidazole-4-carboxylic acid, monohydrochloride;
a-amino-6,7,8,9-tetrahydro-e-1H-imidazol-2-yl-3-oxo-3H, 5H-[1,2,4]-oxadiazolo[4,3-a]azepine-5-hexanoic acid;
phenylmethyl(2S,4Z)-2-[[(1,1-dimethylethoxy)carbonyl] amino]-6-(6,7,8,9-tetrahydro-3-oxo-3H,5H-[1,2,4] oxadiazolo[4,3-a]azepin-5-yl)-4-hexenoate;
3-[ethyl[(6,7,8,9-tetrahydro-3-oxo-3H,5H-[1,2,4] oxadiazolo[4,3-a]azepin-5-yl)methyl]amino]-L-alanine;
(2S)-2-[[(phenylmethoxy)carbonyl]amino]-4-[[(6,7,8,9-tetrahydro-3-oxo-3H,5H-[1,2,4]oxadiazolo[4,3-a]azepin-5-yl)carbonyl]amino]butanoic acid;
N-[(phenylmethoxy)carbonyl]-O-[(6,7,8,9-tetrahydro-3-oxo-3H,5H-[1,2,4]oxadiazolo[4,3-a]azepin-5-yl)methyl]-L-serine;
Bis(1,1-dimethylethyl)4-nitro-4-[(6,7,8,9-tetrahydro-3-oxo-3H,5H-[1,2,4]oxadiazolo[4,3-a]azepin-5-yl)methyl] heptanedioate;
S-[(6,7,8,9-tetrahydro-3-oxo-3H,5H-[1,2,4]oxadiazolo[4,3-a]azepin-5-yl)methyl]homocysteine;
S-[2-(6,7,8,9-tetrahydro-3-oxo-3H,5H-[1,2,4]oxadiazolo[4, 3-a]azepin-5-yl)ethyl]-L-cysteine;
S-[2-(6,7,8,9-tetrahydro-3-oxo-3H,5H-[1,2,4]oxadiazolo[4, 3-a]azepin-5-yl)ethyl]homocysteine; and
N-[(1,1-dimethylethoxy)carbonyl]-3-[ethyl[(6,7,8,9-tetrahydro-3-oxo-3H,5H-[1,2,4]oxadiazolo[4,3-a]azepin-5-yl)methyl]amino]-L-alanine.

15. A compound represented by a structural formula selected from the group consisting of

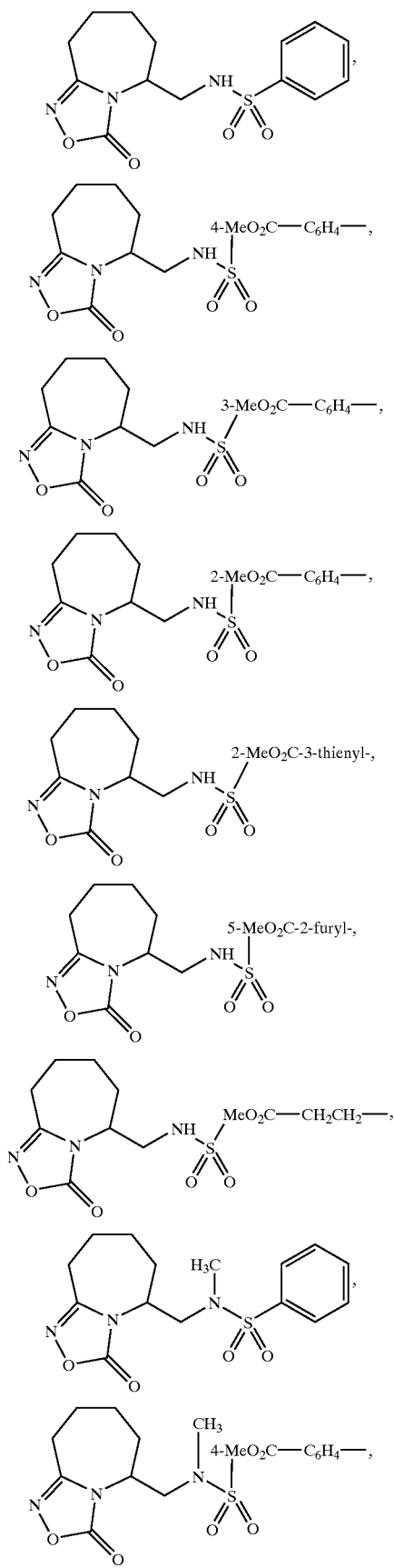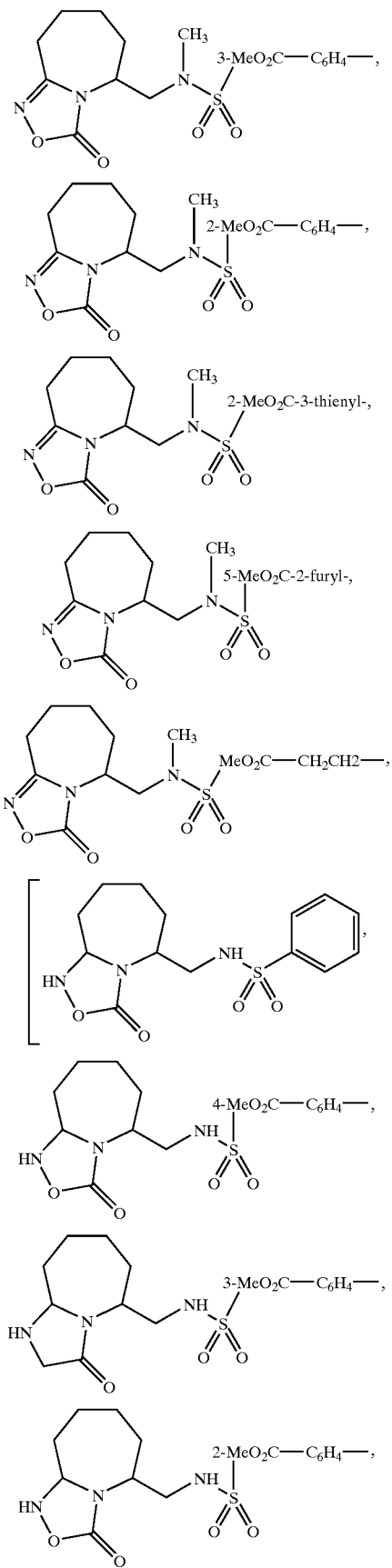

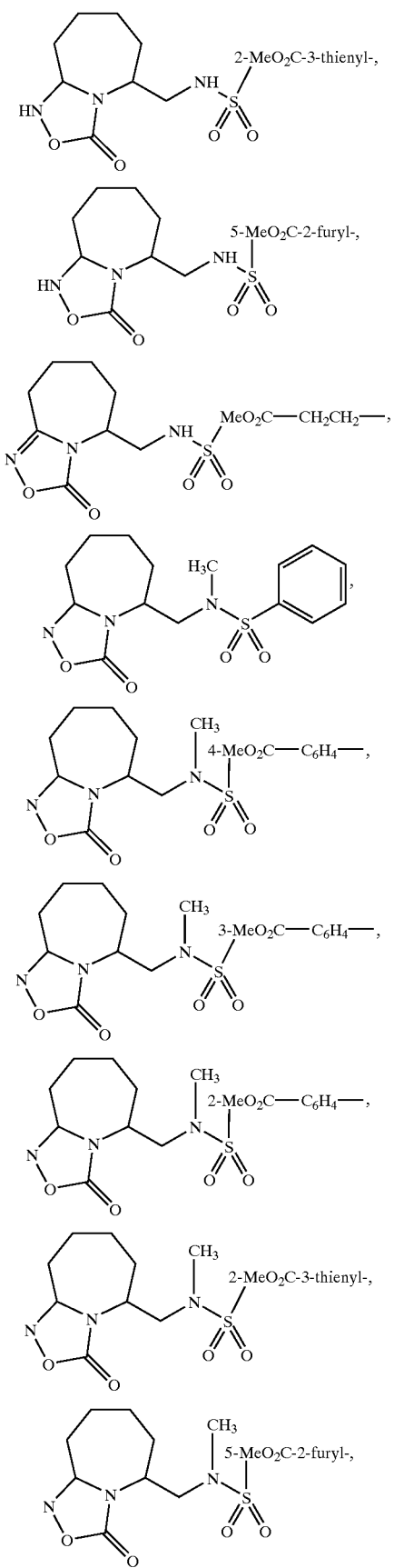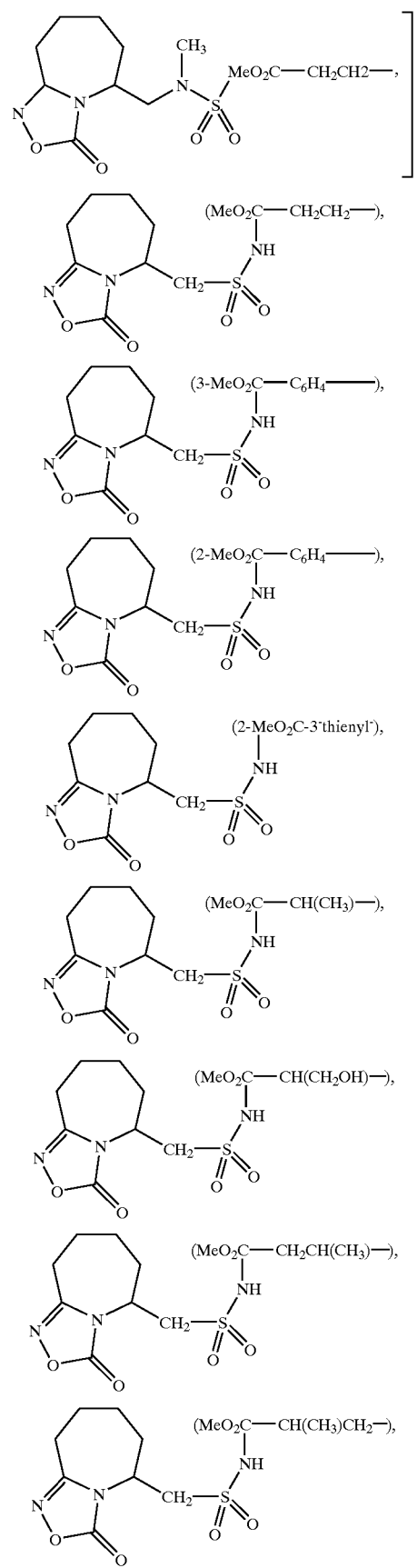

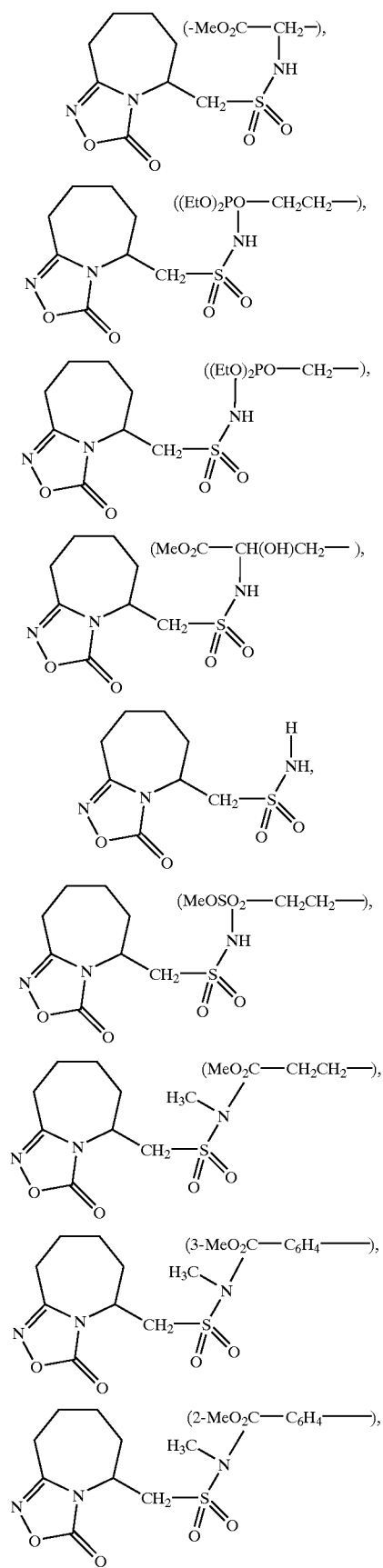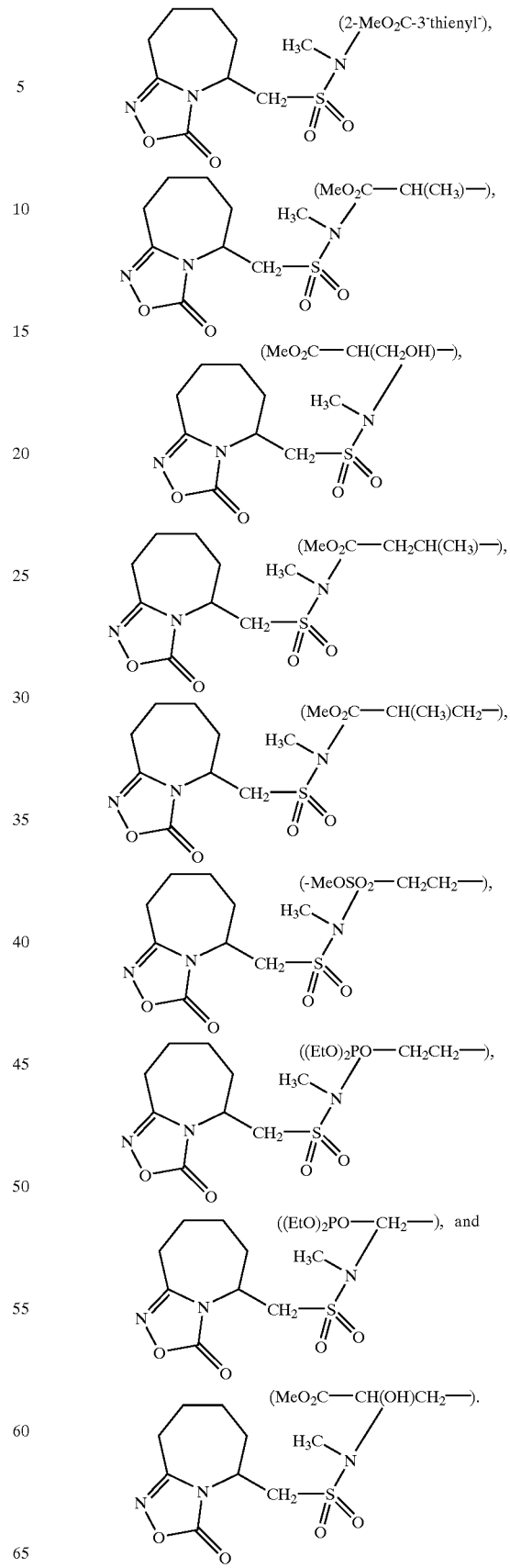

16. A compound as recited in claim 1 wherein the compound is selected from the group consisting of
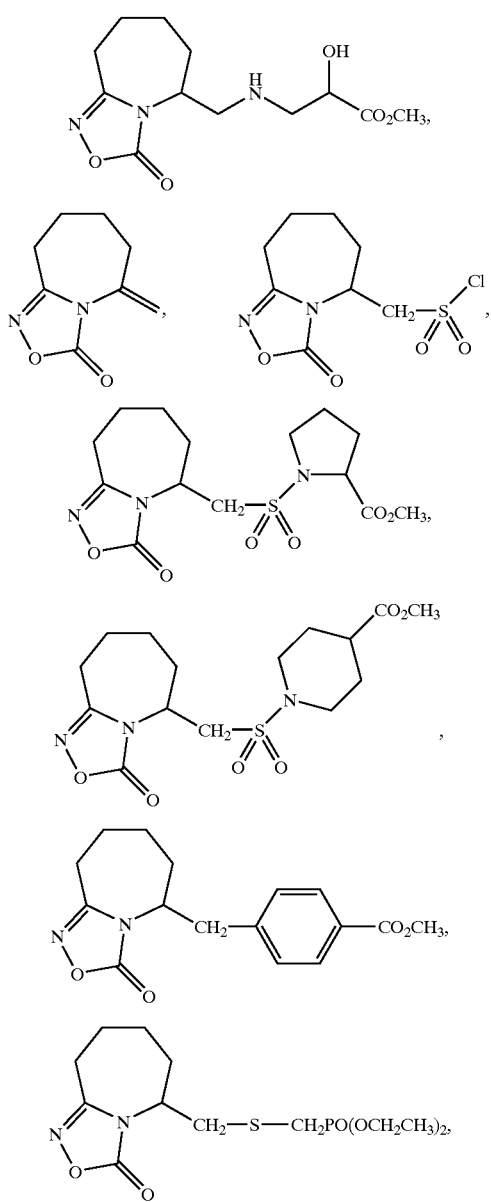
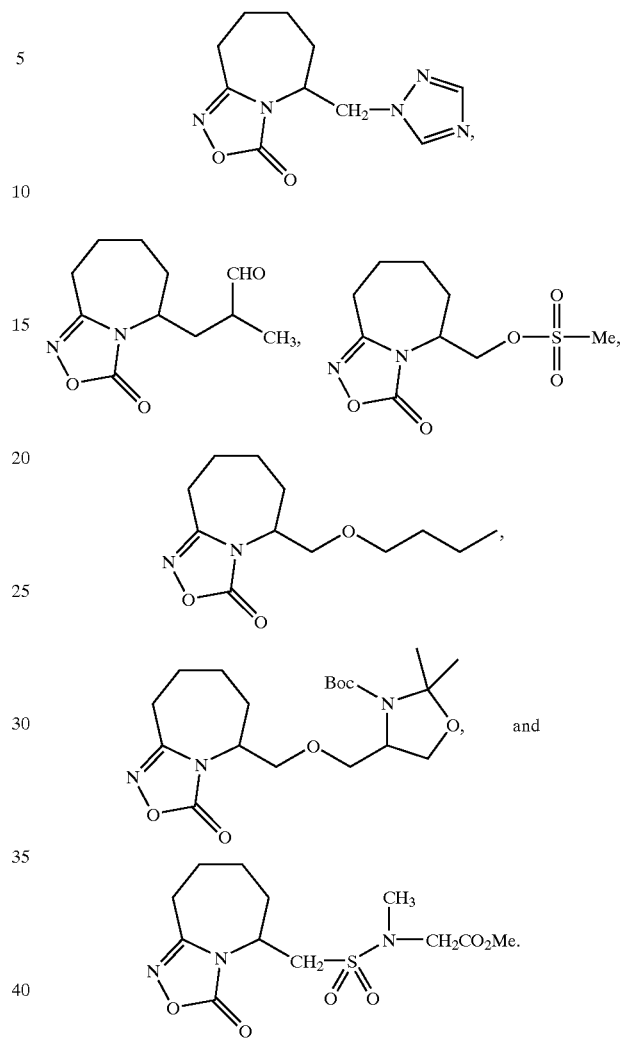
17. A pharmaceutical composition comprising a compound of claim 1, 2, 3, 4, 5, 6, 7, 8, 9, 10, 11, 12, 13, 14, 15 or 16 and together with at least one non-toxic pharmaceutical acceptable carrier.
* * * * *